US011311465B2

(12) United States Patent
Bouarfa et al.

(10) Patent No.: US 11,311,465 B2
(45) Date of Patent: *Apr. 26, 2022

(54) GEL-TYPE COSMETIC COMPOSITION WITH IMPROVED STAYING POWER

(71) Applicant: L'OREAL, Paris (FR)

(72) Inventors: Bouchra Bouarfa, Paris (FR); Véronique Ferrari, Maisons-Alfort (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/507,440

(22) PCT Filed: Aug. 26, 2015

(86) PCT No.: PCT/IB2015/056474
§ 371 (c)(1),
(2) Date: Feb. 28, 2017

(87) PCT Pub. No.: WO2016/030842
PCT Pub. Date: Mar. 3, 2016

(65) Prior Publication Data
US 2017/0290747 A1    Oct. 12, 2017

(30) Foreign Application Priority Data

Aug. 28, 2014 (FR) ...................... 1458064

(51) Int. Cl.
| | | |
|---|---|---|
| *A61K 8/04* | (2006.01) | |
| *A61K 8/26* | (2006.01) | |
| *A61Q 1/02* | (2006.01) | |
| *A61K 8/891* | (2006.01) | |
| *A61K 8/81* | (2006.01) | |
| *A61Q 1/10* | (2006.01) | |
| *A61K 8/92* | (2006.01) | |

(52) U.S. Cl.
CPC ............ *A61K 8/042* (2013.01); *A61K 8/8158* (2013.01); *A61K 8/891* (2013.01); *A61K 8/92* (2013.01); *A61Q 1/02* (2013.01); *A61Q 1/10* (2013.01)

(58) Field of Classification Search
None
See application file for complete search history.

(56) References Cited

U.S. PATENT DOCUMENTS

| | | | |
|---|---|---|---|
| 5,266,321 A * | 11/1993 | Shukuzaki | A61K 8/375 424/401 |
| 5,470,884 A | 11/1995 | Corless et al. | |
| 6,120,780 A | 9/2000 | Dupuis et al. | |
| 6,187,323 B1 | 2/2001 | Aiache et al. | |
| 6,287,543 B1 * | 9/2001 | Terren | A61K 8/03 424/401 |
| 6,497,861 B1 | 12/2002 | Wang et al. | |
| 6,916,464 B2 | 7/2005 | Hansenne et al. | |
| 7,942,937 B2 * | 5/2011 | Brun | A61K 8/731 8/405 |
| 8,216,554 B2 | 7/2012 | Shah et al. | |
| 8,333,956 B2 | 12/2012 | Brieva et al. | |
| 8,449,870 B2 | 5/2013 | Wang et al. | |
| 8,858,967 B2 | 10/2014 | Astruc et al. | |
| 10,238,584 B2 * | 3/2019 | Valverde | A61K 8/732 |
| 2003/0026772 A1 | 2/2003 | Jager-Lezer et al. | |
| 2003/0223943 A1 | 12/2003 | Uang et al. | |
| 2005/0048016 A1 | 3/2005 | Lebreton et al. | |
| 2005/0163730 A1 | 7/2005 | Rosevear et al. | |
| 2005/0196364 A1 * | 9/2005 | Josso | A61K 8/8158 424/59 |
| 2007/0231354 A1 | 10/2007 | Sogabe et al. | |
| 2008/0064761 A1 | 3/2008 | Gondek et al. | |
| 2010/0086502 A1 | 4/2010 | Lucet-Levannier et al. | |
| 2010/0221296 A1 | 9/2010 | Moneuze et al. | |
| 2010/0310481 A1 | 12/2010 | Chevalier et al. | |
| 2010/0322983 A1 * | 12/2010 | Griffiths-Brophy | A61K 8/894 424/401 |
| 2011/0014139 A1 | 1/2011 | Viala et al. | |
| 2011/0158920 A1 * | 6/2011 | Morley | A61P 17/04 424/59 |
| 2011/0286947 A1 * | 11/2011 | Luukas | A61K 8/86 424/61 |
| 2012/0138078 A1 | 6/2012 | Ricard | |

(Continued)

FOREIGN PATENT DOCUMENTS

| | | |
|---|---|---|
| BR | PI0405758-9 A | 9/2006 |
| CN | 101272823 A | 9/2008 |
| CN | 102026682 A | 4/2011 |

(Continued)

OTHER PUBLICATIONS

Seppinov EMT 10, Seppic, Apr. 2006, pp. 1-10 (Year: 2006).*
Jan. 19, 2018 Office Action issued in U.S. Appl. No. 15/314,221.
Oct. 20, 2017 Third Party Observation issued in Japanese Patent Application No. 2015-558600.
Dow Corning VM-2270 (Aerogel Fine Particles (2012) accessed at http://www.dowcorning.com/content/publishedlit/27-1235.pdf accessed Jan. 10, 2018 (Year: 2012)).
Jan. 9, 2018 Office Action issued in Japanese Application No. 2015-558599.
Elizabeth Arden, "Moister Lotion SPF 15," Mintel, pp. 1-3, Record ID: 639186, Jan. 2007.

(Continued)

*Primary Examiner* — Lakshmi S Channavajjala
(74) *Attorney, Agent, or Firm* — Oliff PLC

(57) ABSTRACT

A composition, especially a cosmetic composition, for making up and/or caring for keratin materials, in particular the skin and/or the lips, and keratin fibres, especially the eyebrows, comprising at least one aqueous phase gelled with at least one hydrophilic gelling agent, and at least one oily phase gelled with at least one lipophilic gelling agent, said phases forming therein a macroscopically homogeneous mixture and said composition also comprising at least one hydrophobic film-forming polymer.

20 Claims, No Drawings

(56) References Cited

U.S. PATENT DOCUMENTS

2017/0189278 A1* 7/2017 Bchir .................. A61K 8/25

FOREIGN PATENT DOCUMENTS

| | | | |
|---|---|---|---|
| EP | 0 388 582 A2 | 9/1990 | |
| EP | 0 963 751 A2 | 12/1999 | |
| EP | 1 495 750 A1 | 1/2005 | |
| EP | 1 818 042 A2 | 8/2007 | |
| EP | 2 135 525 A2 | 12/2009 | |
| EP | 2 492 333 A1 | 8/2012 | |
| FR | 2 986 422 A1 | 8/2013 | |
| FR | 2 986 424 A1 | 8/2013 | |
| FR | 2 992 203 A1 | 12/2013 | |
| JP | S60-6607 A | 1/1985 | |
| JP | 2005-029575 A | 2/2005 | |
| JP | 2005-112834 A | 4/2005 | |
| JP | 2005-232107 A | 9/2005 | |
| JP | 2005-314391 A | 11/2005 | |
| JP | 2007-217411 A | 8/2007 | |
| JP | 2007-527452 A | 9/2007 | |
| JP | 2007-262032 A | 10/2007 | |
| JP | 2009-502852 A | 1/2009 | |
| JP | 2010-006708 A | 1/2010 | |
| JP | 2010-111674 A | 5/2010 | |
| JP | 2011-088850 A | 5/2011 | |
| JP | 2011-213652 A | 10/2011 | |
| WO | 99/22696 A1 | 5/1999 | |
| WO | 99/62497 A1 | 12/1999 | |
| WO | 99/65455 A1 | 12/1999 | |
| WO | 01/89470 A1 | 11/2001 | |
| WO | 2008/081175 A2 | 7/2008 | |
| WO | 2008/114732 A1 | 9/2008 | |
| WO | 2011/143254 A2 | 11/2011 | |
| WO | 2013/087927 A1 | 6/2013 | |
| WO | 2013/093869 A2 | 6/2013 | |
| WO | 2013/107000 A1 | 7/2013 | |
| WO | WO2013107000 * | 7/2013 | .............. A61K 8/11 |
| WO | 2014/128678 A1 | 8/2014 | |
| WO | 2014/128680 A1 | 8/2014 | |
| WO | WO 2014128680 A1 * | 8/2014 | .............. A61K 8/26 |

OTHER PUBLICATIONS

Marks & Spencer, "Daly Protect Everyday Moisturiser SPF 12," Mintel, pp. 1-3, Record ID: 1448926, Dec. 2010.
Jul. 4, 2017 Third Party Observation issued in European Application No. 14710991.2.
Jul. 13, 2017 Third Party Observation issued in European Application No. 14708695.3.
Scrubs, "Instant Lifting Cream," Mintel, Record ID: 1912786, pp. 1-3, Nov. 2012.
Almeida, et al., "Moisturizing Effect of Oleogel/Hydrogel Mixtures", Pharmaceutical Development and Technology, vol. 13, Jan. 2, 2008, pp. 487-494, XP009174126.
May 9, 2014 Written Opinion of the International Searching Authority issued in PCT Patent Application No. PCT/IB2014/059238.
May 9, 2014 International Search Report issued in Patent Application No. PCT/IB2014/059238.
U.S. Appl. No. 14/770,292, filed Aug. 25, 2015 in the name of Valverde et al.
U.S. Appl. No. 14/770,154, filed Aug. 25, 2015 in the name of Ferrari et al.
U.S. Appl. No. 14/770,182, filed Aug. 25, 2015 in the name of Valverde et al.
Almeida, et al., "Evaluation of the Physical Stability of Two Oleogels", International Journal of Pharmaceutics, vol. 327, No. 1-2, Dec. 11, 2006, pp. 73-77.
May 15, 2014 Written Opinion of the International Searching Authority issued in PCT Patent Application No. PCT/IB2014/059239.
May 15, 2014 International Search Report issued in Patent Application No. PCT/IB2014/059239.
May 27, 2014 Written Opinion of the International Searching Authority issued in PCT Patent Application No. PCT/IB2014/059240.
May 27, 2014 International Search Report issued in Patent Application No. PCT/IB2014/059240.
Feb. 23, 2016 Office Action issued in U.S. Appl. No. 14/770,154.
Jul. 15, 2016 Office Action issued in U.S. Appl. No. 14/770,154.
Technical data sheet. Viscosity of Carbpool Polymers in Aqueous Systems. Lubrizol. 2009. 10p.
Aug. 1, 2016 Office Action issued in U.S. Appl. No. 14/770,292.
Aug. 3, 2016 Office Action issued in U.S. Appl. No. 14/770,182.
Jan. 19, 2017 Office Action Issued In U.S. Appl. No. 14/770,292.
Seppic, "Sepinov EMT 10," Apr. 2006, pp. 1-19.
Jan. 19, 2017 Office Action issued in U.S. Appl. No. 14/770,182.
Jul. 31, 2015 International Search Report issued in International Patent Application No. PCT/IB2015/053953.
Kobayashi. "Oil Up Cosmetic Material Consist Disperse System Silicone Gel Composition Polysiloxane Powder Base Agent". Sep. 14, 1989. XP002735135.
U.S. Appl. No. 15/507,318, filed Feb. 28, 2017 in the name of Roudot et al.
U.S. Appl. No. 15/314,221, filed Nov. 28, 2016 in the name of Bchir et al.
Jan. 13, 2016 International Search Report issued in International Patent Application No. PCT/IB2015/056474.
Jan. 19, 2016 International Search Report issued in International Patent Application No. PCT/IB2015/056471.
Degussa. "Versatile and Effective", Aerosil. Mar. 3, 2003, p. 1-21. XP003026229.
Apr. 7, 2017 Office Action issued in U.S. Appl. No. 14/770,154.
Jan. 13, 2016 Written Opinion issued in International Patent Application No. PCT/IB2015/056474.
Jan. 19, 2016 Written Opinion issued in International Patent Application No. PCT/IB2015/056471.
May 20, 2015 Written Opinion issued in French Patent Application No. 1458034.
Jul. 31, 2015 Written Opinion issued in International Patent Application No. PCT/IB2015/053953.
May 22, 2017 Office Action issued in U.S. Appl. No. 14/770,292.
Jul. 12, 2017 Office Action issued in U.S. Appl. No. 15/314,221.
Jul. 28, 2017 Office Action issued in U.S. Appl. No. 14/770,182.
May 23, 2018 Office Action issued in U.S. Appl. No. 15/507,318.
Oct. 4, 2018 Office Action issued in U.S. Appl. No. 15/314,221.
Nov. 30, 2018 Office Action issued in U.S. Appl. No. 14/770,292.
Elementis Specialties, "Bentonite Gel ISD V," pp. 1-11, 2008.
Dec. 10, 2018 Office Action issued in U.S. Appl. No. 14/770,154.
Dec. 20, 2018 Office Action issued in U.S. Appl. No. 15/507,318.
Annamarya Scaccia, "What Are the Benefits of Using Avocado Oil on My Skin?," Health Line News Letter, downloaded from https://www.healthline.com/health /beauty-skin-care/ avocado-oil-for-skin on Dec. 14, 2018, (Year 2018).
Unknown Author, "Safety Assessment of Alkoxy Polysiloxane as Used in Cosmetics," released Feb. 21, 2014 (only pertinent portion is provided), (Year 2014).
Sep. 13, 2019 Office Action issued in U.S. Appl. No. 15/507,318.
Oct. 1, 2019 Office Action issued in U.S. Appl. No. 14/770,154.
Zasypkin et al., "Multicomponent Biopolymer Gels," Food Hydrocolloids, vol. 11, No. 2, pp. 159-170, 1997.
Levy et al., "The Effect of Certain Additives on the Gel Point of Methylcellulose," J. American Pharmaceutical Association, vol. XLVII, No. 1, pp. 44-46, 1958.
Stokes et al., "Measuring the Yield Behaviour of Structured Fluids," J. Non-Newtonian Fluid Mech., vol. 124, pp. 137-146, 2004.
Jan. 8, 2020 Office Action issued in U.S. Appl. No. 15/314,221.
Feb. 26, 2020 Office Action issued in U.S. Appl. No. 16/729,918.
Apr. 1, 2020 U.S. Office Action issued U.S. Appl. No. 15/507,318.
Oct. 9, 2020 Office Action issued in U.S. Appl. No. 15/507,318.
Jul. 2, 2020 Office Action issued in U.S. Appl. No. 16/729,918.
Jul. 15, 2020 Office Action issued in U.S. Appl. No. 15/314,221.
Jul. 23, 2021 Office Action Issued in U.S. Appl. No. 15/507,318.
Mar. 15, 2021 Office Action issued in U.S. Appl. No. 15/507,318.

(56) References Cited

OTHER PUBLICATIONS

May 2, 2019 Office Action issued in U.S. Appl. No. 15/314,221.
May 3, 2019 Office Action issued in U.S. Appl. No. 15/507,318.
Dec. 15, 2021 Office Action issued in U.S. Appl. No. 15/507,318.
Apr. 19, 2018 Office Action issued in U.S. Appl. No. 14/770,154.
May 4, 2018 Office Action issue in U.S. Appl. No. 14/770,292.
May 4, 2018 Office Action issue in U.S. Appl. No. 14/770,182.

* cited by examiner

GEL-TYPE COSMETIC COMPOSITION WITH IMPROVED STAYING POWER

The present invention is directed towards proposing for the field of caring for and/or making up keratin materials, especially the skin and/or the lips, and in particular the skin and keratin fibres, especially the eyebrows, a novel galenical form that is most particularly advantageous with regard to its technical performance and the sensations it affords the user during its application thereto, in particular to the skin.

The term "keratin materials" especially means the skin, the lips, the eyebrows and/or the eyelashes, in particular the skin and/or the eyebrows, and preferably the skin.

Cosmetic compositions, for example foundations, are commonly used to give the skin an aesthetic colour, but also to hide and/or unify imperfections of the skin relief such as wrinkles and/or scars. In this regard, many solid or fluid, anhydrous or non-anhydrous formulations have been developed to date.

Multi-phase compositions exist at the present time, which are advantageous as regards the makeup properties they impart, especially a matt effect and coverage. However, the corresponding compositions that are currently available do not prove to be entirely satisfactory. Specifically, they do not always ensure staying power over time of the matt effect, which tends to degrade in the course of the day.

Consequently, it would be advantageous to optimize multi-phase compositions for their cosmetic uses in terms of the staying power of the resulting makeup, including the staying power of the matt effect over time and the homogeneity of the makeup, without, however, impairing their other performance qualities.

Specifically, users with combination to greasy skin expect these formulations to be persistent. They especially want these products to give them a matt effect, while at the same time avoiding making the skin shiny in the course of the day, and also giving a uniform makeup result.

Other cosmetic compositions, for example for fixing the eyebrows, are also known to those skilled in the art. They are usually of anhydrous architecture, in particular in pencil form. These pencils, which are applied to the skin and the eyebrows, are intended to redraw the eyebrows.

However, these formulations have the drawback of colouring the skin more than the eyebrows and of migrating or even running, which makes the makeup result non-uniform over time.

Consequently, it would also be advantageous to have available cosmetic compositions, intended for making up the eyebrows, which are capable, firstly, of depositing dyestuff onto the surface of the eyebrows, i.e. onto the keratin fibre and not essentially onto the skin, and, secondly, of ensuring satisfactory staying power of this deposit over time.

The present invention is specifically directed towards meeting these needs.

Thus, according to one of its aspects, the present invention relates to a composition, especially a cosmetic composition, for making up and/or caring for keratin materials, in particular the skin and/or the lips, and keratin fibres, especially the eyebrows, comprising:
at least one aqueous phase gelled with at least one hydrophilic gelling agent; and
at least one oily phase gelled with at least one lipophilic gelling agent;
said phases forming therein a macroscopically homogeneous mixture;
said composition also comprising at least one hydrophobic film-forming polymer.

According to a preferred embodiment, a composition according to the invention comprises pigments in combination with a polar additive.

For the purposes of the invention, the term "polar additive" means a polar compound characterized by a polarity parameter $\delta a$ equal to or greater than 3.0 $(J/cm^3)^{1/2}$.

For the purposes of the invention, the term "polarity parameter" means the mean parameter $\delta a$ reflecting the polarity of a molecule: the higher the value of $\delta a$, the higher the polarity of the molecule.

The mean parameter $\delta a$ is defined as a function of the Hansen solubility parameters $\delta p$ and $\delta h$, according to the following relationship: $\delta a = \sqrt{(\delta p^2 + \delta h^2)}$.

The parameters $\delta p$ and $\delta h$ characterize, respectively, the Debye interaction forces between permanent dipoles and the capacity of a compound to give hydrogen bonds. These parameters are defined according to the Hansen solubility parameter space in the document J. Paint Technology 39, 195 (1967) "The Three Dimensional Solubility Parameter—Key to Paint Component Affinities".

Contrary to all expectation, and as emerges from the examples given below, the inventors have found that the formulation of a hydrophobic film-forming polymer in a gel-gel architecture as defined above makes it possible to boost the staying power over time of the matt effect, and to significantly improve the staying power of the makeup deposit.

Furthermore, these compositions make it possible to afford freshness and lightness while at the same time masking the areas of imperfection of the skin relief or the areas free of hairs in the eyebrow fringe.

"Gel-gel" compositions have already been proposed in the cosmetics field. Formulations of this type combine a gelled aqueous phase with a gelled oily phase. Thus, gel/gel formulations are described in Almeida et al., Pharmaceutical Development and Technology, 2008, 13:487, tables 1 and 2, page 488; WO 99/65455; PI 0405758-9; WO 99/62497; JP 2005-112834 and WO 2008/081175. However, to the inventors' knowledge, this type of composition does not at the present time make it possible to ensure all the essential properties expected in the cosmetic field, such as a pleasant texture when handling the product, a non-tacky, comfortable and uniform deposit of makeup, or stability over time of the formulation.

As stated above, the inventors have found that the use of hydrophobic film-forming polymers in a multi-phase composition according to the invention makes it possible to ensure the staying power over time of the matt effect, as illustrated in the examples.

Thus, a composition according to the invention shows very good staying power of the matt effect over time, while at the same time affording the user a sensation of freshness and lightness. Finally, the composition proves to be easy to apply to the surface of the targeted keratin material.

According to another of its aspects, a subject of the invention is also a process for preparing a composition, especially a cosmetic composition for making up and/or caring for keratin materials, in particular the skin and/or the lips, and keratin fibres, especially the eyebrows, comprising at least one step of mixing:
an aqueous phase gelled with at least one hydrophilic gelling agent; and
at least one oily phase gelled with at least one lipophilic gelling agent;
under conditions suitable for obtaining a macroscopically homogeneous mixture;

said composition also comprising at least one hydrophobic film-forming polymer.

According to one embodiment variant, this process may advantageously comprise a step of mixing at least three or even more gelled phases.

For obvious reasons, the number of gelled aqueous phases and of gelled oily phases to be considered for forming a composition according to the invention may range for each of the two types of phase beyond two.

Advantageously, the mixing of the phases may be performed at room temperature.

However, the process of the invention may comprise, if necessary, a step of heating the mixture.

According to one embodiment variant, the final formulation may be manufactured without following a particular order of introduction of the various constituents and, in certain cases, a "one-pot" manufacture may be performed.

According to a particular embodiment, the representative gelled phases of the same type of architecture are gelled with a different gelling agent.

Multi-phase formulas may thus be developed.

According to another of its aspects, a subject of the invention is also a process, especially a cosmetic process, for making up and/or caring for a keratin material, in particular the skin and/or the lips, and keratin fibres, especially the eyebrows, comprising at least one step which consists in applying to said keratin material a composition in accordance with the invention.

According to yet another of its aspects, the present invention relates to a cosmetic process for making up and/or caring for a keratin material, in particular the skin and/or the lips, and keratin fibres, especially the eyebrows, comprising at least the application to said material of a macroscopically homogeneous composition obtained by extemporaneous mixing, before application or at the time of application to said keratin material, of at least one aqueous phase gelled with at least one hydrophilic gelling agent, and at least one oily phase gelled with at least one lipophilic gelling agent; and said composition also comprising at least one hydrophobic film-forming polymer.

Cosmetic Composition

To begin with, it is important to note that a composition according to the invention is different from an emulsion.

An emulsion generally consists of an oily liquid phase and an aqueous liquid phase. It is a dispersion of droplets of one of the two liquid phases in the other. The size of the droplets forming the dispersed phase of the emulsion is typically about a micrometre (0.1 to 100 μm). Furthermore, an emulsion requires the presence of a surfactant or of an emulsifier to ensure its stability over time.

In contrast, a composition according to the invention consists of a macroscopically homogeneous mixture of two immiscible gelled phases. These two phases both have a gel-type texture. This texture is especially reflected visually by a consistent and/or creamy appearance.

The term "macroscopically homogeneous mixture" means a mixture in which each of the gelled phases cannot be individualized by the naked eye. More precisely, in a composition according to the invention, the gelled aqueous phase and the gelled oily phase interpenetrate and thus form a stable, consistent product. This consistency is achieved by mixing interpenetrated macrodomains. These interpenetrated macrodomains are not measurable objects. Thus, by microscope, the composition according to the invention is very different from an emulsion. A composition according to the invention cannot be characterized either as having a "sense", i.e. an O/W or W/O sense, this means that a continuous phase and a dispersed phase cannot be defined.

Thus, a composition according to the invention has a consistency of gel type. The stability of the composition is long-lasting without surfactant. Consequently, a composition, especially a cosmetic composition according to the invention, does not require any surfactant or silicone emulsifier to ensure its stability over time.

A composition according to the invention is distinguishable from an emulsion by mean of at least one of the following tests: test using a dyestuff, drop test and dilution test.

Test Using a Dyestuff

It is known practice from the prior art to observe the intrinsic nature of a mixture of aqueous and oily gels in a gel-type composition, for example, by introducing a dyestuff either into the aqueous gelled phase or into the lipophilic gelled phase, before the formation of the gel-type composition. During visual inspection, in a gel-type composition, the dyestuff appears uniformly dispersed, even if the dye is present solely in the gelled aqueous phase or in the gelled oily phase. Specifically, if two different dyes of different colours are introduced, respectively, into the oily phase and into the aqueous phase, before formation of the gel-type composition, the two colours may be observed as being uniformly dispersed throughout the gel-type composition. This is different from an emulsion in which, if a dye, which is soluble in water or soluble in oil, is introduced, respectively, into the aqueous and oily phases, before forming the emulsion, the colour of the dye present will only be observed in the outer phase (Remington: The Science and Practice of Pharmacy, 19th Edition (1995), Chapter 21, page 282).

Drop Test

It is also known practice to distinguish a gel-type composition from an emulsion by performing a "drop test". This test consists in demonstrating the bi-continuous nature of a gel-type composition. Specifically, as mentioned previously, the consistency of a composition is obtained by means of the interpenetration of the aqueous and oily gelled domains. Consequently, the bi-continuous nature of a gel-type composition may be demonstrated by means of a simple test with, respectively, hydrophilic and hydrophobic solvents. This test consists in depositing, firstly, one drop of a hydrophilic solvent on a first sample of the test composition, and, secondly, one drop of a hydrophobic solvent on a second sample of the same test composition, and in analysing the behaviour of the two drops of solvents. In the case of an O/W emulsion, the drop of hydrophilic solvent diffuses into the sample and the drop of hydrophobic solvent remains at the surface of the sample. In the case of a W/O emulsion, the drop of hydrophilic solvent remains at the surface of the sample and the drop of hydrophobic solvent diffuses throughout the sample. Finally, in the case of a gel-type composition (bi-continuous system), the hydrophilic and hydrophobic drops diffuse throughout the sample.

Dilution Test

In the case of the present invention, the test that will be preferred for distinguishing a gel-type composition from an emulsion is a dilution test. Specifically, in a gel-type composition, the aqueous and oily gelled domains interpenetrate and form a consistent and stable composition, in which the behaviour in water and in oil is different from the behaviour of an emulsion. Consequently, the behaviour during dilution of a gel-type composition (bi-continuous system) may be compared to that of an emulsion, obviously the behaviour during dilution of a gel/gel-type composition and the one of a emulsion will be different.

More specifically, the dilution test consists in placing 40 g of product and 160 g of dilution solvent (water or oil) in a 500 mL plastic beaker. The dilution is performed with controlled stirring to avoid any emulsification. In particular, this is performed using a planetary mixer: Speed Mixer™ DAC400FVZ. The speed of the mixer is set at 1500 rpm for 4 minutes. Finally, observation of the resulting sample is performed using an optical microscope at a magnification of ×100 (×10×10). It may be noted that oils such as Parleam® and Xiameter PMX-200 Silicone Fluid 5CS® sold by Dow Corning are suitable as dilution solvent, in the same respect as one of the oils contained in the composition.

In the case of a gel-type composition (bi-continuous system), when it is diluted in oil or in water, a heterogeneous appearance is always observed. When a gel-type composition (bi-continuous system) is diluted in water, pieces of oily gel in suspension are observed, and when a gel-type composition (bi-continuous system) is diluted in oil, pieces of aqueous gel in suspension are observed.

In contrast, during dilution, emulsions have a different behaviour. When an O/W emulsion is diluted in an aqueous solvent, it gradually reduces without having a heterogeneous and lumpy appearance. This same O/W emulsion, on dilution with oil, has a heterogeneous appearance (pieces of O/W emulsion suspended in the oil). When a W/O emulsion is diluted with an aqueous solvent, it has a heterogeneous appearance (pieces of W/O emulsion suspended in the water). This same W/O emulsion, when diluted in oil, gradually reduces without having a heterogeneous and lumpy appearance.

According to the present invention, the aqueous gelled phase and the oily gelled phase forming a composition according to the invention are present therein in a weight ratio ranging from 95/5 to 5/95. More preferentially, the aqueous phase and the oily phase are present in a weight ratio ranging from 30/70 to 80/20.

The ratio between the two gelled phases is adjusted according to the desired cosmetic properties.

Thus, in the case of a makeup composition, in particular for the face, it will be advantageous to favour an aqueous gelled phase/oily gelled phase weight ratio of greater than 1, especially ranging from 60/40 to 90/10, preferably ranging from 60/40 to 80/20, preferentially from 60/40 to 70/30 and even more preferentially to favour an aqueous gelled phase/oily gelled phase weight ratio of 60/40 or 70/30.

These preferred ratios are particularly advantageous for obtaining fresh and light compositions.

Advantageously, a composition according to the invention may thus be in the form of a creamy gel with a minimum stress below which it does not flow unless it has been subjected to an external mechanical stress.

As emerges from the text hereinbelow, a composition according to the invention may have a minimum threshold stress of 1.5 Pa and in particular greater than 10 Pa.

The composition according to the invention may have a maximum threshold stress of 10 000 Pa preferably of 5 000 Pa.

It also advantageously has a stiffness modulus G* at least equal to 400 Pa and preferably greater than 1000 Pa. The composition according to the invention may have a stiffness modulus G* preferably lower than 50 000 Pa, more preferably lower than 5 000 Pa.

The ratio of the hydrophilic phase viscosity/lipophilic phase viscosity (measured at 25° C. and 100 s$^{-1}$) preferably ranges from 0.2 and 3.

According to an advantageous embodiment variant, the gelled phases under consideration to form a composition according to the invention have, respectively, a threshold stress of greater than 1.5 Pa and preferably greater than 10 Pa.

The gelled phases under consideration to form a composition according to the invention may have a threshold stress lower than 10 000 Pa preferably lower than 5 000 Pa.

Characterization of the threshold stresses is performed by oscillating rheology measurements. Methodology is proposed in the illustrative chapter of the present text.

In general, the corresponding measurements are taken at 25° C. using a Haake RS600 imposed-stress rheometer equipped with a plate-plate measuring body (60 mm diameter) fitted with an anti-evaporation device (bell jar). For each measurement, the sample is placed delicately in position and the measurements start 5 minutes after placing the sample in the jaws (2 mm). The test composition is then subjected to a stress ramp from $10^{-2}$ to $10^3$ Pa at a set frequency of 1 Hz.

A composition according to the invention may also have a certain elasticity. This elasticity may be characterized by a stiffness modulus G* which, under this minimum stress threshold, may be at least equal to 400 Pa and preferably greater than 1000 Pa. The value G* of a composition may be obtained by subjecting the composition under consideration to a stress ramp from $10^{-2}$ to $10^3$ Pa at a set frequency of 1 Hz.

Hydrophilic Gelling Agent

For the purposes of the present invention, the term "hydrophilic gelling agent" means a compound that is capable of gelling the aqueous phase of the compositions according to the invention.

The gelling agent is hydrophilic and is thus present in the aqueous phase of the composition.

The gelling agent may be water-soluble or water-dispersible.

As stated above, the aqueous phase of a composition according to the invention is gelled with at least one hydrophilic gelling agent.

The hydrophilic gelling agent may be chosen from synthetic polymeric gelling agents, polymeric gelling agents that are natural or of natural origin, mixed silicates and fumed silicas, and mixtures thereof.

Preferably, the hydrophilic gelling agent may be chosen from synthetic polymeric gelling agents.

I. Polymeric Gelling Agents that are Natural or of Natural Origin

The polymeric hydrophilic gelling agents that are suitable for use in the invention may be natural or of natural origin.

For the purposes of the invention, the term "of natural origin" is intended to denote polymeric gelling agents obtained by modification of natural polymeric gelling agents.

These gelling agents may be particulate or non-particulate.

More specifically, these gelling agents fall within the category of polysaccharides.

In general, polysaccharides may be divided into several categories.

Thus, polysaccharides that are suitable for use in the invention may be homopolysaccharides such as fructans, glucans, galactans and mannans or heteropolysaccharides such as hemicellulose.

Similarly, they may be linear polysaccharides such as pullulan or branched polysaccharides such as gum arabic and amylopectin, or mixed polysaccharides such as starch.

More particularly, the polysaccharides that are suitable for use in the invention may be distinguished according to whether or not they are starchy.

I.A. Starchy Polysaccharides

As representatives of this category, mention may be made most particularly of native starches, modified starches and particulate starches.

Native Starches

The starches that may be used in the present invention are more particularly macromolecules in the form of polymers consisting of elementary moieties which are anhydroglucose units (dextrose), linked via α(1,4) bonds of chemical formula $(C_6H_{10}O_5)_n$. The number of these moieties and their assembly make it possible to distinguish amylose, a molecule formed from about 600 to 1000 linearly linked glucose molecules, and amylopectin, a polymer branched approximately every 25 glucose residues (α(1,6) bond). The total chain may include between 10 000 and 100 000 glucose residues.

Starch is described in particular in *Kirk-Othmer's Encyclopaedia of Chemical Technology*, 3rd edition, volume 21, pages 492-507, Wiley Interscience, 1983.

The relative proportions of amylose and of amylopectin, and their degree of polymerization, vary as a function of the botanical origin of the starches. On average, a sample of native starch consists of about 25% amylose and 75% amylopectin.

Occasionally, phytoglycogen is present (between 0% and 20% of the starch), which is an analogue of amylopectin but branched every 10 to 15 glucose residues.

Starch may be in the form of semi-crystalline granules: amylopectin is organized in leaflets, amylose forms a less well organized amorphous zone between the various leaflets.

Amylose is organized in a straight helix with six glucoses per turn. It dissociates into assimilable glucose under the action of enzymes, amylases, all the more easily when it is in amylopectin form. Specifically, the helical formation does not promote the accessibility of starch to the enzymes.

Starches are generally in the form of a white powder, which is insoluble in cold water, whose elemental particle size ranges from 3 to 100 microns.

By treating it with hot water, starch paste is obtained. It is exploited in industry for its thickening and gelling properties.

The botanical origin of the starch molecules used in the present invention may be cereals or tubers. Thus, the starches are chosen, for example, from corn starch, rice starch, cassava starch, tapioca starch, barley starch, potato starch, wheat starch, sorghum starch and pea starch.

The native starches are represented, for example, by the products sold under the names C*Amilogel™, Cargill Gel™, C* Gel™, Cargill Gum™, DryGel™ and C*Pharm Gel™ by the company Cargill, under the name Corn Starch by the company Roquette, and under the name Tapioca Pure by the company National Starch.

Modified Starches

The modified starches used in the composition of the invention may be modified via one or more of the following reactions: pregelatinization, degradation (acid hydrolysis, oxidation, dextrinization), substitution (esterification, etherification), crosslinking (esterification), bleaching.

More particularly, these reactions may be performed in the following manner:
  pregelatinization by splitting the starch granules (for example drying and cooking in a drying drum);
  acid hydrolysis giving rise to very rapid retrogradation on cooling;
  oxidation with strong oxidizing agents (alkaline medium, in the presence of sodium hypochlorite NaOCl for example) leading to depolymerization of the starch molecule and to the introduction of carboxyl groups into the starch molecule (mainly oxidation of the hydroxyl group at $C_6$);
  dextrinization in acid medium at high temperature (hydrolysis followed by repolymerization);
  crosslinking with functional agents capable of reacting with the hydroxyl groups of the starch molecules, which will thus bond together (for example with glyceryl and/or phosphate groups);
  esterification in alkaline medium for the grafting of functional groups, especially $C_1$-$C_6$ acyl (acetyl), $C_1$-$C_6$ hydroxyalkyl (hydroxyethyl or hydroxypropyl), carboxymethyl or octenylsuccinic.

Monostarch phosphates (of the type St-O—PO—(OX)$_2$), distarch phosphates (of the type St-O—PO—(OX)—O-St) or even tristarch phosphates (of the type St-O—PO—(O-St)$_2$) or mixtures thereof may especially be obtained by crosslinking with phosphorus compounds.

X in particular denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

According to the invention, it is also possible to use amphoteric starches, these amphoteric starches containing one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The amphoteric starches are especially chosen from the compounds having the following formulae:

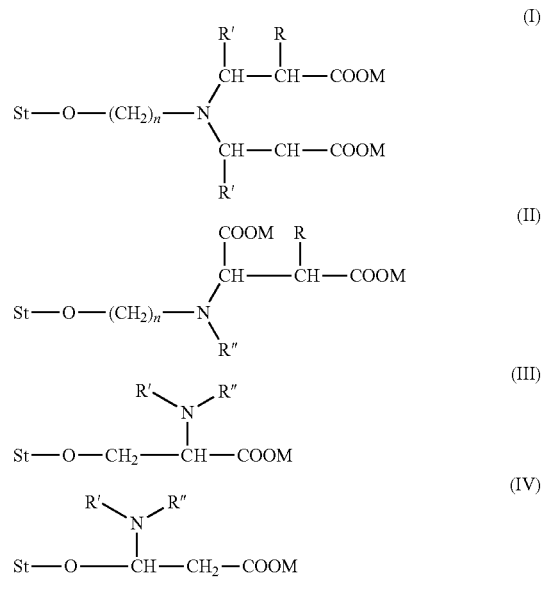

in which:
St-O represents a starch molecule;
R, which may be identical or different, represents a hydrogen atom or a methyl radical;
R', which may be identical or different, represents a hydrogen atom, a methyl radical or a —COOH group;
n is an integer equal to 2 or 3;
M, which may be identical or different, denotes a hydrogen atom, an alkali metal or alkaline-earth metal such as Na, K, Li or $NH_4$, a quaternary ammonium or an organic amine,
R" represents a hydrogen atom or an alkyl radical containing from 1 to 18 carbon atoms.

These compounds are especially described in U.S. Pat. Nos. 5,455,340 and 4,017,460.

The starch molecules may be derived from any plant source of starch, especially such as corn, potato, oat, rice, tapioca, sorghum, barley or wheat. It is also possible to use the starch hydrolysates mentioned above.

The modified starches are represented, for example, by the products sold under the names C*Tex-Instant (pregelatinized adipate), C*StabiTex-Instant (pregelatinized phosphate), C*PolarTex-Instant (pregelatinized hydroxypropyl), C*Set (acid hydrolysis, oxidation), C*size (oxidation), C*BatterCrisp (oxidation), C*DrySet (dextrinization), C*Tex™ (acetyl distarch adipate), C*PolarTex™ (hydroxypropyl distarch phosphate), C* StabiTex™ (distarch phosphate, acetyl distarch phosphate) by the company Cargill, by distarch phosphates or compounds rich in distarch phosphate such as the product sold under the references Prejel VA-70-T AGGL (gelatinized hydroxypropyl cassava distarch phosphate) or Prejel TK1 (gelatinized cassava distarch phosphate) or Prejel 200 (gelatinized acetyl cassava distarch phosphate) by the company Avebe or Structure Zea from National Starch (gelatinized corn distarch phosphate).

As examples of oxidized starches, use will be made especially of those sold under the name C*size from the company Cargill.

The native or modified starches described above may be advantageously used in a proportion of from 0.1% to 8% by weight of solids and preferably at about 1% by weight, relative to the total weight of the aqueous phase.

Particulate Starches

Particulate starches that may be mentioned in particular include:
starches grafted with an acrylic polymer (homopolymer or copolymer) and especially with sodium polyacrylate, for instance those sold under the names Sanfresh ST-100MC by the company Sanyo Chemical Industries or Makimousse 25, Makimousse 12 by the company Daito Kasei (INCI name: Sodium polyacrylate starch),
hydrolysed starches grafted with an acrylic polymer (homopolymer or copolymer) and especially acryloacrylamide/sodium acrylate copolymer, for instance those sold under the names Water Lock A-240, A-180, B-204, D-223, A-100, C-200 and D-223 by the company Grain Processing (INCI name: Starch/acrylamide/sodium acrylate copolymer);
polymers based on starch, gum and cellulose derivative, such as the product containing starch, and sodium carboxymethylcellulose, for instance the product sold under the name Lysorb 220 by the company Lysac.

Mention may be made most particularly of $C_1$-$C_4$ carboxyalkyl starches, also referred to hereinbelow as carboxyalkyl starch. These compounds are obtained by grafting carboxyalkyl groups onto one or more alcohol functions of starch, especially by reaction of starch and of sodium monochloroacetate in alkaline medium.

The carboxyalkyl groups are generally attached via an ether function, more particularly to carbon 1. The degree of substitution with carboxyalkyl units of the $C_1$-$C_4$ carboxyalkyl starch preferably ranges from 0.1 to 1 and more particularly from 0.15 to 0.5. The degree of substitution is defined according to the present invention as being the mean number of hydroxyl groups substituted with an ester or ether group per monosaccharide unit of the polysaccharide.

The carboxyalkyl starches are advantageously used in the form of salts and especially of salts of alkali metals or alkaline-earth metals such as Na, K, Li, $NH_4$, or salts of a quaternary ammonium or of an organic amine such as monoethanolamine, diethanolamine or triethanolamine. The $C_1$-$C_4$ carboxyalkyl starches are advantageously, in the context of the present invention, carboxymethyl starches. The carboxymethyl starches preferably comprise units having the following formula:

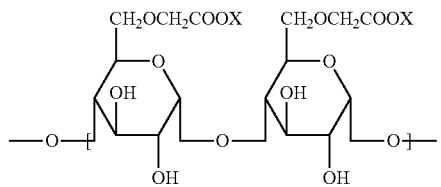

in which X, optionally covalently bonded to the carboxylic unit, denotes a hydrogen atom, an alkali metal or alkaline-earth metal such as Na, K, Li, $NH_4$, a quaternary ammonium or an organic amine, for instance monoethanolamine, diethanolamine or triethanolamine.

Preferably, X denotes a cation $Na^+$. The carboxyalkyl starches that may be used according to the present invention are preferably non-pregelatinized carboxyalkyl starches. The carboxyalkyl starches that may be used according to the present invention are preferably partially or totally cross-linked carboxyalkyl starches.

In general, a crosslinked carboxyalkyl starch has, in contrast with a non-crosslinked carboxyalkyl starch, an increased, controllable viscosity and increased stability. The crosslinking thus makes it possible to reduce the syneresis phenomena and to increase the resistance of the gel to shear effects.

The carboxyalkyl starches under consideration according to the invention are more particularly potato carboxyalkyl starches. Thus, the carboxyalkyl starches that may be used according to the present invention are preferably sodium salts of carboxyalkyl starches, in particular a sodium salt of potato carboxymethyl starch, sold especially under the name Primojel® by the company DMV International or Glycolys® and Glycolys® LV by the company Roquette.

According to a particular mode, use will be made of the potato carboxymethyl starches sold especially under the name Glycolys® by the company Roquette. As stated previously, the $C_1$-$C_4$ carboxyalkyl starch particles are present in the compositions according to the invention in a swollen and non-split form. This swelling may be characterized by a swelling power Q which may advantageously be between 10 and 30 ml/g and preferably between 15 and 25 ml (volume of absorbed liquid)/g of dry particulate material.

Thus, the size of the swollen carboxyalkyl starch particles used according to the present invention generally ranges from 25 to 300 μm. For example, the gel Primojel® containing 10% by weight of potato carboxyalkyl starch and sodium salt in water contains more than 80% of swollen particles of this starch with a diameter of greater than 50 microns and more particularly greater than 100 microns.

According to a preferred embodiment variant of the invention, these particles are used for the preparation of the compositions according to the invention, in this swollen particulate state. To do so, these particles are advantageously used in the form of an aqueous gel either prepared beforehand or already commercially available. The gels under consideration according to the invention are advantageously translucent.

For example, a carboxymethyl starch gel such as Primojel® which is at a concentration of 10% by weight may be adjusted to the required concentration before being used for preparing the expected composition.

Such a particulate starch may be used in a proportion of from 0.1% to 5% by weight of solids relative to the total weight of the aqueous phase, preferably between 0.5% and 2.5% by weight and in particular in a proportion of about 1.5% by weight, relative to the total weight of the aqueous phase.

According to one embodiment variant, the hydrophilic gelling agent is non-starchy.

I.B. Non-Starchy Polysaccharides

In general, the non-starchy polysaccharides may be chosen from polysaccharides produced by microorganisms; polysaccharides isolated from algae, and higher plant polysaccharides, such as homogeneous polysaccharides, in particular celluloses and derivatives thereof or fructosans, heterogeneous polysaccharides such as gum arabics, galactomannans, glucomannans and pectins, and derivatives thereof and mixtures thereof.

In particular, the polysaccharides may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglucans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

These polysaccharides may be chemically modified, especially with urea or urethane groups or by hydrolysis, oxidation, esterification, etherification, sulfatation, phosphatation, amination, amidation or alkylation reaction, or by several of these modifications.

The derivatives obtained may be anionic, cationic, amphoteric or nonionic.

Advantageously, the polysaccharides may be chosen from carrageenans, in particular kappa carrageenan, gellan gum, agar-agar, xanthan gum, alginate-based compounds, in particular sodium alginate, scleroglucan gum, guar gum, inulin and pullulan, and mixtures thereof.

In general, the compounds of this type that may be used in the present invention are chosen from those described especially in Kirk-Othmer's *Encyclopaedia of Chemical Technology*, Third Edition, 1982, volume 3, pp. 896-900, and volume 15, pp. 439-458, in *Polymers in Nature* by E. A. MacGregor and C. T. Greenwood, published by John Wiley & Sons, Chapter 6, pp. 240-328, 1980, in the book by Robert L. Davidson entitled *Handbook of Water-Soluble Gums and Resins* published by McGraw Hill Book Company (1980) and in *Industrial Gums—Polysaccharides and their Derivatives*, edited by Roy L. Whistler, Second Edition, published by Academic Press Inc.

Such a gelling agent may be used in a proportion of from 0.1% to 8% by weight of solids relative to the total weight of the aqueous phase, especially from 0.1% to 6% by weight, preferably between 0.5% and 2.5% by weight and in particular in a proportion of about 1%, or alternatively in a proportion of about 1.5% by weight, relative to the total weight of the aqueous phase.

More precisely, these polysaccharides that are suitable for use in the invention may be distinguished according to whether they are derived from microorganisms, from algae or from higher plants, and are detailed below.

Polysaccharides Produced by Microorganisms

Xanthan

Xanthan is a heteropolysaccharide produced at the industrial scale by the aerobic fermentation of the bacterium *Xanthomonas campestris*. Its structure consists of a main chain of $\beta(1,4)$-linked $\beta$-D-glucoses, similar to cellulose. One glucose molecule in two bears a trisaccharide side chain composed of an $\alpha$-D-mannose, a $\beta$-D-glucuronic acid and a terminal $\beta$-D-mannose. The internal mannose residue is generally acetylated on carbon 6. About 30% of the terminal mannose residues bear a pyruvate group linked in chelated form between carbons 4 and 6. The charged pyruvic acids and glucuronic acids are ionizable, and are thus responsible for the anionic nature of xanthan (negative charge down to a pH equal to 1). The content of pyruvate and acetate residues varies according to the bacterial strain, the fermentation process, the conditions after fermentation and the purification steps. These groups may be neutralized in commercial products with $Na^+$, $K^+$ or $Ca^{2+}$ ions (Satia company, 1986). The neutralized form may be converted into the acid form by ion exchange or by dialysis of an acidic solution.

Xanthan gums have a molecular weight of between 1 000 000 and 50 000 000 and a viscosity of between 0.6 and 1.65 Pa·s for an aqueous composition containing 1% of xanthan gum (measured at 25° C. on a Brookfield viscometer of LVT type at 60 rpm).

Xanthan gums are represented, for example, by the products sold under the names Rhodicare by the company Rhodia Chimie, under the name Satiaxane™ by the company Cargill Texturizing Solutions (for the food, cosmetic and pharmaceutical industries), under the name Novaxan™ by the company ADM, and under the names Kelzan® and Keltrol® by the company CP-Kelco.

Pullulan

Pullulan is a polysaccharide consisting of maltotriose units, known under the name $\alpha(1,4)$-$\alpha(1,6)$-glucan. Three glucose units in maltotriose are connected via an $\alpha(1,4)$ glycoside bond, whereas the consecutive maltotriose units are connected to each other via an $\alpha(1,6)$ glycoside bond.

Pullulan is produced, for example, under the reference Pullulan PF 20 by the group Hayashibara in Japan.

Dextran and Dextran Sulfate

Dextran is a neutral polysaccharide not bearing any charged groups, which is biologically inert, prepared by fermentation of beet sugar containing solely hydroxyl groups.

It is possible to obtain dextran fractions of different molecular weights from native dextran by hydrolysis and purification. Dextran may in particular be in the form of dextran sulfate.

Dextran is represented, for example, by the products sold under the name Dextran or Dextran T by the company Pharmacosmos, or under the name Dextran 40 Powder or Dextran 70 Powder by the company Meito Sangyo Co. Dextran sulfate is sold by the company PK Chemical A/S under the name Dextran sulfate.

Succinoglycan

Succinoglycan is an extracellular polymer of high molecular weight produced by bacterial fermentation, consisting of octasaccharide repeating units (repetition of 8 sugars). Succinoglycans are sold, for example, under the name Rheozan by the company Rhodia.

Scleroglucan

Scleroglucan is a nonionic branched homopolysaccharide consisting of β-D-glucan units. The molecules consist of a linear main chain formed from D-glucose units linked via β(1,3) bonds and of which one in three is linked to a side D-glucose unit via a β(1,6) bond.

A more complete description of scleroglucans and of their preparation may be found in U.S. Pat. No. 3,301,848.

Scleroglucan is sold, for example, under the name Amigel by the company Alban Müller, or under the name Actigum™ CS by the company Cargill.

Gellan Gum

Gellan gum is an anionic linear heteropolyoside based on oligoside units composed of 4 saccharides (tetra-oside). D-Glucose, L-rhamnose and D-glucuronic acid in 2:1:1 proportions are present in gellan gum in the form of monomer elements.

It is sold, for example, under the name Kelcogel CG LA by the company CP Kelco.

Polysaccharides Isolated from Algae

Galactans

The polysaccharide according to the invention may be a galactan chosen especially from agar and carrageenans.

Carrageenans are anionic polysaccharides constituting the cell walls of various red algae (Rhodophyceae) belonging to the Gigartinacae, Hypneaceae, Furcellariaceae and Polyideaceae families. They are generally obtained by hot aqueous extraction from natural strains of said algae. These linear polymers, formed by disaccharide units, are composed of two D-galactopyranose units linked alternately by α(1,3) and β(1,4) bonds. They are highly sulfated polysaccharides (20-50%) and the α-D-galactopyranosyl residues may be in 3,6-anhydro form. Depending on the number and position of sulfate-ester groups on the repeating disaccharide of the molecule, several types of carrageenans are distinguished, namely: kappa-carrageenans, which bear one sulfate-ester group, iota-carrageenans, which bear two sulfate-ester groups, and lambda-carrageenans, which bear three sulfate-ester groups.

Carrageenans are composed essentially of potassium, sodium, magnesium, triethanolamine and/or calcium salts of polysaccharide sulfate esters.

Carrageenans are sold especially by the company SEPPIC under the name Solagum®, by the company Gelymar under the names Carragel®, Carralact® and Carrasol®, by the company Cargill, under the names Satiagel™ and Satiagum™, and by the company CP-Kelco under the names Genulacta®, Genugel® and Genuvisco®.

Galactans of agar type are galactose polysaccharides contained in the cell wall of some of these species of red algae (rhodophyceae). They are formed from a polymer group whose base backbone is a β(1,3) D-galactopyranose and α(1,4) L 3-6 anhydrogalactose chain, these units repeating regularly and alternately. The differences within the agar family are due to the presence or absence of solvated methyl or carboxyethyl groups. These hybrid structures are generally present in variable percentage, depending on the species of algae and the harvest season.

Agar-agar is a mixture of polysaccharides (agarose and agaropectin) of high molecular mass, between 40 000 and 300 000 g·mol$^{-1}$. It is obtained by manufacturing algal extraction liquors, generally by autoclaving, and by treating these liquors which comprise about 2% of agar-agar, so as to extract the latter.

Agar is produced, for example, by the group B&V Agar Producers under the names Gold Agar, Agarite and Grand Agar by the company Hispanagar, and under the names Agar-Agar, QSA (Quick Soluble Agar), and Puragar by the company Setexam.

Furcellaran

Furcellaran is obtained commercially from red algae *Furcellaria fasztigiata*. Furcellaran is produced, for example, by the company Est-Agar.

Alginate-Based Compound

For the purposes of the invention, the term "alginate-based compound" means alginic acid, alginic acid derivatives and salts of alginic acid (alginates) or of said derivatives.

Preferably, the alginate-based compound is water-soluble.

Alginic acid, a natural substance resulting from brown algae or certain bacteria, is a polyuronic acid composed of 2 uronic acids linked by 1,4-glycosidic bonds: β-D-mannuronic (M) acid and α-L-glucuronic (G) acid.

Alginic acid is capable of forming water-soluble salts (alginates) with alkali metals such as sodium, potassium or lithium, substituted cations of lower amines and of substituted ammonium such as methylamine, ethanolamine, diethanolamine or triethanolamine. These alginates are water-soluble in aqueous medium at a pH equal to 4, but dissociate into alginic acid at a pH below 4.

This (these) alginate-based compound(s) is/are capable of crosslinking in the presence of at least one crosslinking agent, by formation of ionic bonds between said alginate-based compound(s) and said crosslinking agent(s). The formation of multiple crosslinking between several molecules of said alginate-based compound(s) leads to the formation of a water-insoluble gel.

Use is preferably made of alginate-based compounds with a weight-average molecular mass ranging from 10 000 to 1 000 000, preferably from 15 000 to 500 000 and better still from 20 000 to 250 000.

According to a preferred embodiment, the alginate-based compound is alginic acid and/or a salt thereof.

Advantageously, the alginate-based compound is an alginate salt, and preferably sodium alginate.

The alginate-based compound may be chemically modified, especially with urea or urethane groups or by hydrolysis, oxidation, esterification, etherification, sulfatation, phosphatation, amination, amidation or alkylation reaction, or by several of these modifications.

The derivatives obtained may be anionic, cationic, amphoteric or nonionic.

The alginate-based compounds that are suitable for use in the invention may be represented, for example, by the products sold under the names Kelcosol, Satialgine™ Cecalgum™ or Algogel™ by the company Cargill Products, under the name Protanal™ by the company FMC Biopolymer, under the name Grindsted® Alginate by the company Danisco, under the name Kimica Algin by the company Kimica, and under the names Manucol® and Manugel® by the company ISP.

Polysaccharides of Higher Plants

This category of polysaccharides may be divided into homogeneous polysaccharides (only one saccharide species) and heterogeneous polysaccharides composed of several types of saccharides.

a) Homogeneous Polysaccharides and Derivatives Thereof

The polysaccharide according to the invention may be chosen from celluloses and derivatives or fructosans.

Cellulose and Derivatives

The polysaccharide according to the invention may also be a cellulose or a derivative thereof, especially cellulose ethers or esters (e.g.: methylcellulose, carboxymethylcellulose, hydroxymethylcellulose, hydroxyethylcellulose, hydroxypropylcellulose, hydroxymethylpropylcellulose, cellulose acetate, cellulose nitrate, nitrocellulose).

The invention may also contain a cellulose-based associative polymer. According to the invention, the term "cellulose-based compound" means any polysaccharide compound bearing in its structure linear sequences of anhydroglucopyranose residues (AGU) linked together via β(1,4) bonds. The repeating unit is the cellobiose dimer. The AGUs are in chair conformation and bear 3 hydroxyl functions: 2 secondary alcohols (in position 2 and 3) and a primary alcohol (in position 6). The polymers thus formed combine together via intermolecular bonds of hydrogen bond type, thus giving the cellulose a fibrillar structure (about 1500 molecules per fibre).

The degree of polymerization differs enormously depending on the origin of the cellulose; its value may range from a few hundred to several tens of thousands.

Cellulose has the following chemical structure:

example, mention may be made of carboxymethylcelluloses, carboxymethylmethylcelluloses and carboxymethylhydroxyethylcelluloses and sodium salts thereof.

Among the cationic cellulose ethers, mention may be made of crosslinked or non-crosslinked, quaternized hydroxyethylcelluloses.

The quaternizing agent may in particular be glycidyltrimethylammonium chloride or a fatty amine such as laurylamine or stearylamine. Another cationic cellulose ether that may be mentioned is hydroxyethylcellulosehydroxypropyltrimethylammonium.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Among the cellulose derivatives, mention may also be made of:
celluloses modified with groups comprising at least one fatty chain, for instance hydroxyethylcelluloses modi-

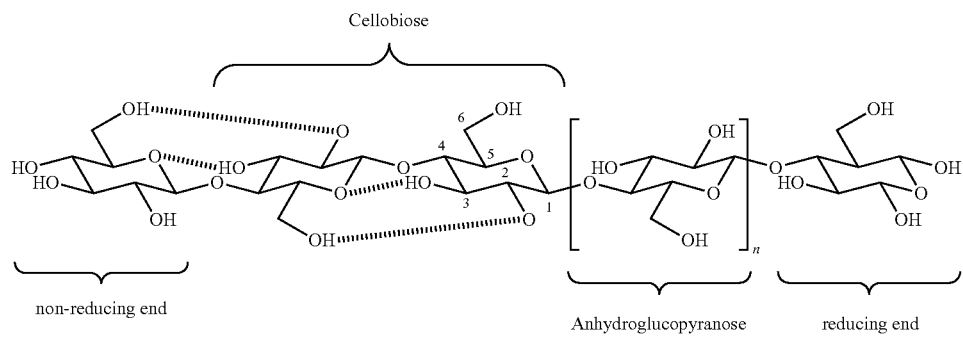

fied with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon, and
celluloses modified with polyalkylene glycol alkylphenyl ether groups, such as the product Amercell Polymer HM-1500 (nonylphenyl polyethylene glycol (15) ether) sold by the company Amerchol.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, The hydroxyl groups of cellulose may react partially or totally with various chemical reagents to give cellulose derivatives having intrinsic properties. The cellulose derivatives may be anionic, cationic, amphoteric or nonionic. Among these derivatives, cellulose ethers, cellulose esters and cellulose ester ethers are distinguished.

Among the nonionic cellulose ethers, mention may be made of alkylcelluloses such as methylcelluloses and ethylcelluloses; hydroxyalkylcelluloses such as hydroxymethylcelluloses, hydroxyethylcelluloses and hydroxypropylcelluloses; and mixed hydroxyalkylalkylcelluloses such as hydroxypropylmethylcelluloses, hydroxyethylmethylcelluloses, hydroxyethyl ethylcelluloses and hydroxybutylmethylcelluloses.

Among the anionic cellulose ethers, mention may be made of carboxyalkylcelluloses and salts thereof. By way of mention may be made of hydroxypropylmethylcellulose phthalates and ethylcellulose sulfates.

The cellulose-based compounds of the invention may be chosen from unsubstituted celluloses and substituted celluloses.

The celluloses and derivatives are represented, for example, by the products sold under the names Avicel® (microcrystalline cellulose, MCC) by the company FMC Biopolymers, under the name Cekol (carboxymethylcellulose) by the company Noviant (CP-Kelco), under the name Akucell AF (sodium carboxymethylcellulose) by the company Akzo Nobel, under the name Methocel™ (cellulose ethers) and Ethocel™ (ethylcellulose) by the company Dow, and under the names Aqualon® (carboxymethylcellulose and sodium carboxymethylcellulose), Benecel® (methylcellulose), Blanose™ (carboxymethylcellulose), Culminal® (methylcellulose, hydroxypropylmethylcellulose), Klucel® (hydroxypropylcellulose), Polysurf® (cetylhydroxyethylcellulose) and Natrosol® CS (hydroxyethylcellulose) by the company Hercules Aqualon.

Fructosans

The polysaccharide according to the invention may especially be a fructosan chosen from inulin and derivatives thereof (especially dicarboxy and carboxymethyl inulins).

Fructans or fructosans are oligosaccharides or polysaccharides comprising a sequence of anhydrofructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatic. Fructans generally have a degree of polymerization from 2 to about 1000 and preferably from 2 to about 60.

Three groups of fructans are distinguished. The first group corresponds to products whose fructose units are for the most part linked via β(2,1) bonds. These are essentially linear fructans such as inulins.

The second group also corresponds to linear fructoses, but the fructose units are essentially linked via β(2,6) bonds. These products are levans.

The third group corresponds to mixed fructans, i.e. containing β(2,6) and β(2,1) sequences. These are essentially branched fructans, such as graminans.

The preferred fructans in the compositions according to the invention are inulins. Inulin may be obtained, for example, from chicory, dahlia or Jerusalem artichoke, preferably from chicory.

In particular, the polysaccharide, especially the inulin, has a degree of polymerization from 2 to about 1000 and preferably from 2 to about 60, and a degree of substitution of less than 2 on the basis of one fructose unit.

The inulin used for this invention is represented, for example, by the products sold under the name Beneo™ inulin by the company Orafti, and under the name Frutafit® by the company Sensus.

b) Heterogeneous Polysaccharides and Derivatives Thereof

The polysaccharides that may be used according to the invention may be gums, for instance *cassia* gum, karaya gum, konjac gum, gum tragacanth, tara gum, acacia gum or gum arabic.

Gum Arabic

Gum arabic is a highly branched acidic polysaccharide which is in the form of mixtures of potassium, magnesium and calcium salts. The monomer elements of the free acid (arabic acid) are D-galactose, L-arabinose, L-rhamnose and D-glucuronic acid.

Galactomannans (Guar, Locust Bean, Fenugreek, Tara Gum) and Derivatives (Guar Phosphate, Hydroxypropyl Guar, Etc.)

Galactomannans are nonionic polyosides extracted from the endosperm of leguminous seeds, of which they constitute the storage carbohydrate.

Galactomannans are macromolecules consisting of a main chain of β(1,4)-linked D-mannopyranose units, bearing side branches consisting of a single D-galactopyranose unit α(1,6)-linked to the main chain. The various galactomannans differ, firstly, by the proportion of α-D-galactopyranose units present in the polymer, and secondly, by significant differences in terms of distribution of galactose units along the mannose chain.

The mannose/galactose (M/G) ratio is about 2 for guar gum, 3 for tara gum and 4 for locust bean gum.

Galactomannans have the following chemical structure:

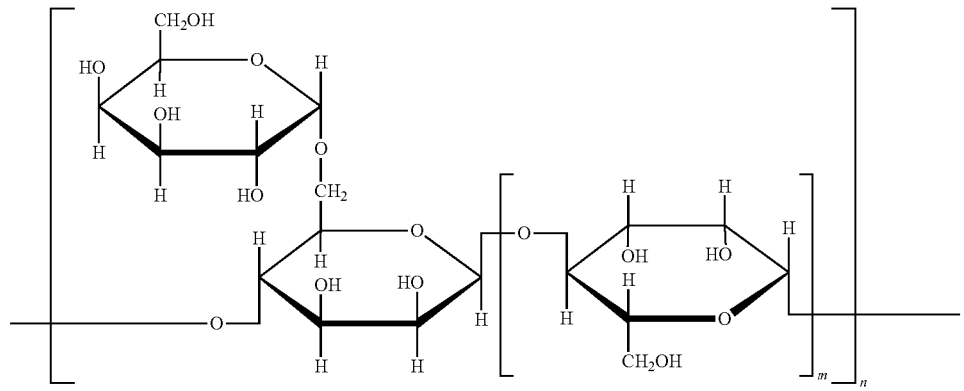

m = 3: Locust beam gum
m = 1: Guar gum
m = 2: Tara gum

Guar

Guar gum is characterized by a mannose/galactose ratio of the order of 2/1. The galactose group is regularly distributed along the mannose chain.

The guar gums that may be used according to the invention may be nonionic, cationic or anionic. According to the invention, use may be made of chemically modified or unmodified nonionic guar gums.

The unmodified nonionic guar gums are, for example, the products sold under the names Vidogum GH, Vidogum G and Vidocrem by the company Unipektin and under the name Jaguar by the company Rhodia, under the name Meypro® Guar by the company Danisco, under the name Viscogum™ by the company Cargill, and under the name Supercol® guar gum by the company Aqualon.

The hydrolysed nonionic guar gums that may be used according to the invention are represented, for example, by the products sold under the name Meyprodor® by the company Danisco.

The modified nonionic guar gums that may be used according to the invention are preferably modified with $C_1$-$C_6$ hydroxyalkyl groups, among which mention may be made, for example, of hydroxymethyl, hydroxyethyl, hydroxypropyl and hydroxybutyl groups.

Such nonionic guar gums optionally modified with hydroxyalkyl groups are sold, for example, under the trade names Jaguar HP 60, Jaguar HP 105 and Jaguar HP 120 (hydroxypropyl guar) by the company Rhodia or under the name N-Hance® HP (hydroxypropyl guar) by the company Aqualon.

The cationic galactomannan gums preferably have a cationic charge density of less than or equal to 1.5 meq./g, more particularly between 0.1 and 1 meq./g. The charge density may be determined by the Kjeldahl method. It generally corresponds to a pH of the order of 3 to 9.

In general, for the purposes of the present invention, the term "cationic galactomannan gum" means any galactomannan gum containing cationic groups and/or groups that can be ionized into cationic groups.

The preferred cationic groups are chosen from those comprising primary, secondary, tertiary and/or quaternary amine groups.

The cationic galactomannan gums used generally have a weight-average molecular mass of between 500 and $5\times10^6$ approximately and preferably between $10^3$ and $3\times10^6$ approximately.

The cationic galactomannan gums that may be used according to the present invention are, for example, gums comprising tri(C1-C4)alkylammonium cationic groups. Preferably, 2% to 30% by number of the hydroxyl functions of these gums bear trialkylammonium cationic groups.

Among these trialkylammonium groups, mention may be made most particularly of trimethylammonium and triethylammonium groups.

Even more preferentially, these groups represent from 5% to 20% by weight relative to the total weight of the modified galactomannan gum.

According to the invention, the cationic galactomannan gum is preferably a guar gum comprising hydroxypropyltrimethylammonium groups, i.e. a guar gum modified, for example, with 2,3-epoxypropyltrimethylammonium chloride.

These galactomannan gums, in particular guar gums modified with cationic groups are products already known per se and are, for example, described in U.S. Pat. Nos. 3,589,578 and 4,031,307. Such products are moreover sold especially under the trade names Jaguar EXCEL, Jaguar C13 S, Jaguar C 15, Jaguar C 17 and Jaguar C162 (Guar Hydroxypropyltrimonium Chloride) by the company Rhodia, under the name Amilan® Guar (Guar Hydroxypropyltrimonium Chloride) by the company Degussa, and under the name N-Hance® 3000 (Guar Hydroxypropyltrimonium Chloride) by the company Aqualon.

The anionic guar gums that may be used according to the invention are polymers comprising groups derived from carboxylic, sulfonic, sulfenic, phosphoric, phosphonic or pyruvic acid. The anionic group is preferably a carboxylic acid group. The anionic group may also be in the form of an acid salt, especially a sodium, calcium, lithium or potassium salt.

The anionic guar gums that may be used according to the invention are preferentially carboxymethyl guar derivatives (carboxymethyl guar or carboxymethyl hydroxypropyl guar).

Locust Bean

Locust bean gum is extracted from the seeds of the locust bean tree (Ceratonia siliqua).

The unmodified locust bean gum that may be used in this invention is sold, for example, under the name Viscogum™ by the company Cargill, under the name Vidogum L by the company Unipektin and under the name Grinsted® LBG by the company Danisco.

The chemically modified locust bean gums that may be used in this invention may be represented, for example, by the cationic locust beans sold under the name Catinal CLB (locust bean hydroxypropyltrimonium chloride) by the company Toho.

Tara Gum

The tara gum that may be used in the context of this invention is sold, for example, under the name Vidogum SP by the company Unipektin.

Glucomannan (Konjac Gum)

Glucomannan is a polysaccharide of high molecular weight (500 000<Mglucomannan<2 000 000) composed of D-mannose and D-glucose units with a branch every 50 or 60 units approximately. It is found in wood, but is also the main constituent of konjac gum. Konjac (Amorphophallus konjac) is a plant of the Araceae family.

The products that may be used according to the invention are sold, for example, under the names Propol® and Rheolex® by the company Shimizu.

LM and HM Pectins, and Derivatives

Pectins are linear polymers of α-D-galacturonic acid (at least 65%) linked in positions 1 and 4 with a certain proportion of carboxylic groups esterified with a methanol group. About 20% of the sugars constituting the pectin molecule are neutral sugars (L-rhamnose, D-glucose, D-galactose, L-arabinose, D-xylose). L-Rhamnose residues are found in all pectins, incorporated into the main chain in positions 1,2.

Uronic acid molecules bear carboxyl functions. This function gives pectins the capacity for exchanging ions, when they are in COO⁻ form. Divalent ions (in particular calcium) have the capacity of forming ionic bridges between two carboxyl groups of two different pectin molecules.

In the natural state, a certain proportion of the carboxylic groups are esterified with a methanol group. The natural degree of esterification of a pectin may range between 70% (apple, lemon) and 10% (strawberry) depending on the source used. Using pectins with a high degree of esterification it is possible to hydrolyse the —$COOCH_3$ groups, so as to obtain weakly esterified pectins. Depending on the proportion of methylated or non-methylated monomers, the chain is thus more or less acidic. HM (high-methoxy)

pectins are thus defined as having a degree of esterification of greater than 50%, and LM (low-methoxy) pectins are defined as having a degree of esterification of less than 50%.

In the case of amidated pectins, the —OCH$_3$ group is substituted with a —NH$_2$ group.

Pectins are especially sold by the company Cargill under the name Unipectine™, by the company CP-Kelco under the name Genu, and by Danisco under the name Grinsted Pectin.

Other Polysaccharides

Among the other polysaccharides that may be used according to the invention, mention may also be made of chitin (poly-N-acetyl-D-glucosamine, β(1,4)-2-acetamido-2-deoxy-D-glucose), chitosan and derivatives (chitosan-beta-glycerophosphate, carboxymethylchitin, etc.) such as those sold by the company France-Chitine; glycosaminoglycans (GAG) such as hyaluronic acid, chondroitin sulfate, dermatan sulfate, keratan sulfate, and preferably hyaluronic acid; xylans (or arabinoxylans) and derivatives.

Arabinoxylans are polymers of xylose and arabinose, all grouped under the name pentosans.

Xylans consist of a main chain of β(1,4)-linked D-xylose units and on which are found three substituents (Rouau & Thibault, 1987): acid units, α-L-arabinofuranose units, side chains which may contain arabinose, xylose, galactose and glucuronic acid.

According to this variant, the polysaccharide is preferably hyaluronic acid, or a salt thereof such as the sodium salt (sodium hyaluronate).

II. Synthetic Polymeric Gelling Agents

For the purposes of the invention, the term "synthetic" means that the polymer is neither naturally existing nor a derivative of a polymer of natural origin.

The synthetic polymeric hydrophilic gelling agent under consideration according to the invention may or may not be particulate.

For the purposes of the invention, the term "particulate" means that the polymer is in the form of particles, preferably spherical particles.

As emerges from the text hereinbelow, the polymeric hydrophilic gelling agent is advantageously chosen from crosslinked acrylic homopolymers or copolymers; associative polymers, in particular associative polymers of polyurethane type; polyacrylamides and crosslinked and/or neutralized 2-acrylamido-2-methylpropanesulfonic acid polymers and copolymers; modified or unmodified carboxyvinyl polymers, and mixtures thereof, especially as defined below.

II.A. Particulate Synthetic Polymeric Gelling Agents

They are preferably chosen from crosslinked polymers.

They may especially be crosslinked acrylic homopolymers or copolymers, which are preferably partially neutralized or neutralized, and which are in particulate form.

According to one embodiment, the particulate gelling agent according to the present invention is chosen from crosslinked sodium polyacrylates. Preferably, it has in the dry or non-hydrated state a mean size of less than or equal to 100 μm and preferably less than or equal to 50 μm. The mean size of the particles corresponds to the mass-average diameter (D50) measured by laser particle size analysis or another equivalent method known to those skilled in the art.

Thus, preferably, the particulate gelling agent according to the present invention is chosen from crosslinked sodium polyacrylates, preferably in the form of particles with a mean size (or mean diameter) of less than or equal to 100 microns, more preferably in the form of spherical particles.

As examples of crosslinked sodium polyacrylates, mention may be made of those sold under the brand names Octacare X100, X110 and RM100 by the company Avecia, those sold under the names Flocare GB300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/Sodium acrylate copolymer) by the company Grain Processing.

Mention may also be made of crosslinked polyacrylate microspheres, for instance those sold under the name Aquakeep® 10 SH NF by the company Sumitomo Seika.

Such gelling agents may be used in a proportion of from 0.1% to 5% by weight of solids relative to the total weight of the aqueous phase, especially from 0.5% to 2% by weight and in particular in a proportion of about from 0.8% to 1.7% by weight, relative to the total weight of the aqueous phase.

II.B. Non Particulate Synthetic Polymeric Gelling Agents

This family of gelling agents may be detailed under the following subfamilies:
1. Associative polymers,
2. Polyacrylamides and crosslinked and/or neutralized 2-acrylamido-2-methylpropanesulfonic acid polymers and copolymers, and
3. Modified or unmodified carboxyvinyl polymers.

II.B.1 Associative Polymers

For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Associative Anionic Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, more particularly by a vinylcarboxylic acid and most particularly by an acrylic acid or a methacrylic acid or mixtures thereof, and whose fatty-chain allyl ether unit corresponds to the monomer of formula (I) below:

$$CH_2=C(R')CH_2OB_nR \qquad (I)$$

in which R' denotes H or CH$_3$, B denotes the ethylenoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably from 10 to 24 and even more particularly from 12 to 18 carbon atoms.

Anionic amphiphilic polymers of this type are described and prepared, according to an emulsion polymerization process, in patent EP 0 216 479.

Among the associative anionic polymers that may also be mentioned are maleic anhydride/C$_{30}$-C$_{38}$-α-olefin/alkyl maleate terpolymers, such as the product maleic anhydride/C$_{30}$-C$_{38}$-α-olefin/isopropyl maleate copolymer sold under the name Performa V 1608 by the company New Phase Technologies.

Among the associative anionic polymers, mention may be made, according to a preferred embodiment, of copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a C$_1$-C$_4$ alcohol.

Examples of compounds of this type that may be mentioned include Aculyn 22® sold by the company Röhm & Haas, which is a methacrylic acid/ethyl acrylate/oxyalkylenated stearyl methacrylate (comprising 20 EO units) terpolymer or Aculyn 28® (methacrylic acid/ethyl acrylate/oxyethylenated behenyl methacrylate (25 EO) terpolymer).

Associative anionic polymers that may also be mentioned include anionic polymers comprising at least one hydrophilic unit of unsaturated olefinic carboxylic acid type, and at least one hydrophobic unit exclusively of the type such as a ($C_{10}$-$C_{30}$) alkyl ester of an unsaturated carboxylic acid. Examples that may be mentioned include the anionic polymers described and prepared according to U.S. Pat. Nos. 3,915,921 and 4,509,949.

Associative anionic polymers that may also be mentioned include anionic terpolymers.

The anionic terpolymer used according to the invention is a linear or branched and/or crosslinked terpolymer, of at least one monomer (1) bearing an acid function in free form, which is partially or totally salified with a nonionic monomer (2) chosen from N,N-dimethylacrylamide and 2-hydroxyethyl acrylate and at least one polyoxyethylenated alkyl acrylate monomer (3) of formula (I) below:

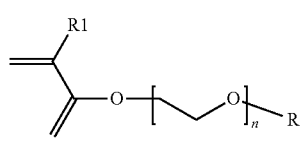

(I)

in which R1 represents a hydrogen atom, R represents a linear or branched $C_2$-$C_5$ alkyl radical and n represents a number ranging from 1 to 10.

The term "branched polymer" denotes a non-linear polymer which bears pendent chains so as to obtain, when this polymer is dissolved in water, a high degree of entanglement leading to very high viscosities, at a low speed gradient.

The term "crosslinked polymer" denotes a non-linear polymer which is in the form of a three-dimensional network that is insoluble in water but swellable in water, leading to the production of a chemical gel.

The acid function of the monomer (1) is especially a sulfonic acid or phosphonic acid function, said functions being in free or partially or totally salified form.

The monomer (1) may be chosen from styrenesulfonic acid, ethylsulfonic acid and 2-methyl-2-[(1-oxo-2-propenyl)amino]-1-propanesulfonic acid (also known as acryloyldimethyl taurate), in free or partially or totally salified form. It is present in the anionic terpolymer preferably in molar proportions of between 5 mol % and 95 mol % and more particularly between 10 mol % and 90 mol %. The monomer (1) will more particularly be 2-methyl-2-[(1-oxo-2-propenyl)amino]-1-propanesulfonic acid in free or partially or totally salified form.

The acid function in partially or totally salified form will preferably be an alkali metal salt such as a sodium or potassium salt, an ammonium salt, an amino alcohol salt such as a monoethanolamine salt, or an amino acid salt such as a lysine salt.

The monomer (2) is preferably present in the anionic terpolymer in molar proportions of between 4.9 mol % and 90 mol %, more particularly between 9.5 mol % and 85 mol % and even more particularly between 19.5 mol % and 75 mol %.

In formula (I), examples of linear $C_8$-$C_{16}$ alkyl radicals that may be mentioned include octyl, decyl, undecyl, tridecyl, tetradecyl, pentadecyl and hexadecyl.

In formula (I), examples of branched $C_8$-$C_{16}$ alkyl radicals that may be mentioned include 2-ethylhexyl, 2-propylheptyl, 2-butyloctyl, 2-pentylnonyl, 2-hexyldecyl, 4-methylpentyl, 5-methylhexyl, 6-methylheptyl, 15-methylpentadecyl, 16-methylheptadecyl and 2-hexyloctyl.

According to a particular form of the invention, in formula (I), R denotes a $C_{12}$-$C_{16}$ alkyl radical.

According to a particular form of the invention, in formula (I), n ranges from 3 to 5.

Tetraethoxylated lauryl acrylate will more particularly be used as monomer of formula (I).

The monomer (3) of formula (I) is preferably present in the anionic terpolymer in molar proportions of between 0.1 mol % and 10 mol % and more particularly between 0.5 mol % and 5 mol %.

According to a particular mode of the invention, the anionic terpolymer is crosslinked and/or branched with a diethylenic or polyethylenic compound in the proportion expressed relative to the total amount of monomers used, from 0.005 mol % to 1 mol %, preferably from 0.01 mol % to 0.5 mol % and more particularly from 0.01 mol % to 0.25 mol %.

The crosslinking agent and/or branching agent is preferably chosen from ethylene glycol dimethacrylate, diallyloxyacetic acid or a salt thereof, such as sodium diallyloxyacetate, tetraallyloxyethane, ethylene glycol diacrylate, diallylurea, triallylamine, trimethylolpropane triacrylate and methylenebis(acrylamide), or mixtures thereof.

The anionic terpolymer may contain additives such as complexing agents, transfer agents or chain-limiting agents.

Use will be made more particularly of an anionic terpolymer of 2-methyl-2-[(1-oxo-2-propenyl)amino]-1-propanesulfonic acid partially or totally salified in the form of the ammonium salt, N,N-dimethylacrylamide and tetraethoxylated lauryl acrylate crosslinked with trimethylolpropane triacrylate, of INCI name Polyacrylate Crosspolymer-6, such as the product sold under the trade name Sepimax Zen® by the company SEPPIC.

Cationic Associative Polymers

Cationic associative polymers that may be mentioned include polyacrylates bearing amine side groups.

The polyacrylates bearing quaternized or non-quaternized amino side groups contain, for example, hydrophobic groups of the type such as steareth-20 (polyoxyethylenated (20) stearyl alcohol).

Examples of polyacrylates bearing amino side chains that may be mentioned are the polymers 8781-121B or 9492-103 from the company National Starch.

Nonionic Associative Polymers

The nonionic associative polymers may be chosen from:
copolymers of vinylpyrrolidone and of fatty-chain hydrophobic monomers;
copolymers of $C_1$-$C_6$ alkyl methacrylates or acrylates and of amphiphilic monomers comprising at least one fatty chain;
copolymers of hydrophilic methacrylates or acrylates and of hydrophobic monomers comprising at least one fatty chain, for instance the polyethylene glycol methacrylate/lauryl methacrylate copolymer;
associative polyurethanes.

Associative polyurethanes are nonionic block copolymers comprising in the chain both hydrophilic blocks usually of polyoxyethylene nature (polyurethanes may also be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisaged. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to one preferred embodiment, a nonionic associative polymer of polyurethane type is used as gelling agent.

As examples of nonionic fatty-chain polyurethane polyethers that may be used in the invention, it is also possible to use Rheolate® FX 1100 (Steareth-100/PEG 136/HDI (hexamethyl diisocyanate) copolymer), Rheolate® 205 containing a urea function, sold by the company Elementis, or Rheolate® 208, 204 or 212, and also Acrysol® RM 184 or Acrysol® RM 2020.

Mention may also be made of the product Elfacos® T210 containing a $C_{12}$-$C_{14}$ alkyl chain, and the product Elfacos® T212 containing a $C_{16-18}$ alkyl chain (PPG-14 Palmeth-60 Hexyl Dicarbamate), from Akzo.

The product DW 1206B® from Röhm & Haas containing a $C_{20}$ alkyl chain and a urethane bond, sold at a solids content of 20% in water, may also be used.

Use may also be made of solutions or dispersions of these polymers, especially in water or in aqueous-alcoholic medium. Examples of such polymers that may be mentioned are Rheolate® 255, Rheolate® 278 and Rheolate® 244 sold by the company Elementis. The products DW 1206F and DW 1206J sold by the company Röhm & Haas may also be used.

The associative polyurethanes that may be used according to the invention are in particular those described in the article by G. Fonnum, J. Bakke and Fk. Hansen, Colloid Polym. Sci., 271, 380-389 (1993).

Even more particularly, according to the invention, use may also be made of an associative polyurethane that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold in particular by the company Röhm & Haas under the names Aculyn® 46 and Aculyn® 44. Aculyn® 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%), and Aculyn® 44 is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%).

Use may also be made of solutions or dispersions of these polymers, especially in water or in aqueous-alcoholic medium. Examples of such polymers that may be mentioned include SER AD FX1010, SER AD FX1035 and SER AD 1070 from the company Elementis, and Rheolate® 255, Rheolate® 278 and Rheolate® 244 sold by the company Elementis. Use may also be made of the products Aculyn® 44, Aculyn® 46, DW 1206F and DW 1206J, and also Acrysol® RM 184 from the company Röhm & Haas, or alternatively Borchigel LW 44 from the company Borchers, and mixtures thereof.

Amphoteric Associative Polymers

Among the associative amphoteric polymers of the invention, mention may be made of crosslinked or non-crosslinked, branched or unbranched amphoteric polymers, which may be obtained by copolymerization:

1) of at least one monomer of formula (IVa) or (IVb):

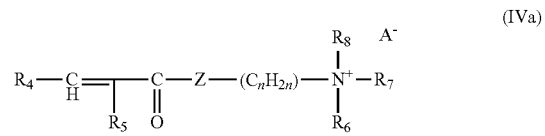

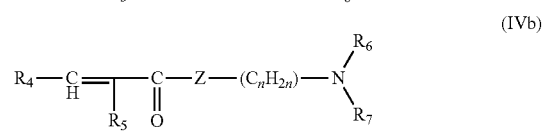

in which $R_4$ and $R_5$, which may be identical or different, represent a hydrogen atom or a methyl radical, $R_6$, $R_7$ and $R_8$, which may be identical or different, represent a linear or branched alkyl radical containing from 1 to 30 carbon atoms;

Z represents an NH group or an oxygen atom;

n is an integer from 2 to 5;

$A^-$ is an anion derived from a mineral or organic acid, such as a methosulfate anion or a halide such as chloride or bromide;

2) of at least one monomer of formula (V):

in which $R_9$ and $R_{10}$, which may be identical or different, represent a hydrogen atom or a methyl radical;

$Z_1$ represents a group OH or a group $NHC(CH_3)_2CH_2SO_3H$;

3) of at least one monomer of formula (VI):

in which $R_9$ and $R_{10}$, which may be identical or different, represent a hydrogen atom or a methyl radical, X denotes an oxygen or nitrogen atom and $R_{11}$ denotes a linear or branched alkyl radical containing from 1 to 30 carbon atoms;

4) optionally at least one crosslinking or branching agent;

at least one of the monomers of formula (IVa), (IVb) or (VI)

comprising at least one fatty chain containing from 8 to 30 carbon atoms and said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group consisting of:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide, dimethylaminopropylacrylamide,
which are optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyl-trimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular such as $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers have a weight-average molecular mass of greater than 500, preferably between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

According to a preferred embodiment, the associative polymer is chosen from nonionic associative polymers and more particularly from associative polyurethanes, such as Steareth-100/PEG-136/HDI Copolymer sold under the name Rheolate FX 1100 by Elementis.

Such an associative polymer is advantageously used in a proportion of from 0.1% to 8% by weight of solids and preferably between 0.5% and 4% by weight, relative to the total weight of the aqueous phase.

II.B.2 Polyacrylamides and 2-acrylamido-2-methylpropanesulfonic acid Polymers and Copolymers The polymers used that are suitable as aqueous gelling agent for the invention may be crosslinked or non-crosslinked homopolymers or copolymers comprising at least the 2-acrylamido-2-methylpropanesulfonic acid (AMPS®) monomer, in a form partially or totally neutralized with a mineral base other than aqueous ammonia, such as sodium hydroxide or potassium hydroxide.

They are preferably totally or almost totally neutralized, i.e. at least 90% neutralized.

These AMPS® polymers according to the invention may be crosslinked or non-crosslinked.

When the polymers are crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allylic or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS® polymers that are suitable for use in the invention are water-soluble or water-dispersible. In this case, they are:
either "homopolymers" comprising only AMPS monomers and, if they are crosslinked, one or more crosslinking agents such as those defined above;
or copolymers obtained from AMPS® and from one or more hydrophilic or hydrophobic ethylenically unsaturated monomers and, if they are crosslinked, one or more crosslinking agents such as those defined above. When said copolymers comprise hydrophobic ethylenically unsaturated monomers, these monomers do not comprise a fatty chain and are preferably present in small amounts.

For the purpose of the present invention, the term "fatty chain" is intended to mean any hydrocarbon-based chain comprising at least 7 carbon atoms.

The term "water-soluble or water-dispersible" means polymers which, when introduced into an aqueous phase at 25° C., at a mass concentration equal to 1%, make it possible to obtain a macroscopically homogeneous and transparent solution, i.e. a solution with a maximum light transmittance value, at a wavelength equal to 500 nm, through a sample 1 cm thick, of at least 60% and preferably of at least 70%.

The "homopolymers" according to the invention are preferably crosslinked and neutralized, and they may be obtained according to the preparation process comprising the following steps:

(a) the monomer such as AMPS in free form is dispersed or dissolved in a solution of tert-butanol or of water and tert-butanol;

(b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%;

(c) the crosslinking monomer(s) are added to the solution or dispersion obtained in (b);

(d) a standard free-radical polymerization is performed in the presence of free-radical initiators at a temperature ranging from 10° C. to 150° C.; the polymer precipitates from the tert-butanol-based solution or dispersion.

The water-soluble or water-dispersible AMPS® copolymers according to the invention contain water-soluble ethylenically unsaturated monomers, hydrophobic monomers, or mixtures thereof.

The water-soluble comonomers may be ionic or nonionic.

Among the ionic water-soluble comonomers, examples that may be mentioned include the following compounds, and salts thereof:

(meth)acrylic acid,
styrenesulfonic acid,
vinylsulfonic acid and (meth)allylsulfonic acid,
vinylphosphonic acid,
maleic acid,
itaconic acid,
crotonic acid,
water-soluble vinyl monomers of formula (A) below:

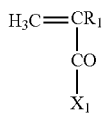
(A)

in which:
$R_1$ is chosen from H, $-CH_3$, $-C_2H_5$ and $-C_3H_7$,
$X_1$ is chosen from:
alkyl oxides of type $-OR_2$ where $R_2$ is a linear or branched, saturated or unsaturated hydrocarbon-based radical containing from 1 to 6 carbon atoms, substituted with at least one sulfonic ($-SO_3-$) and/or sulfate ($-SO_4-$) and/or phosphate ($-PO_4H_2-$) group.

Among the nonionic water-soluble comonomers, examples that may be mentioned include:
(meth)acrylamide,
N-vinylacetamide and N-methyl-N-vinylacetamide,
N-vinylformamide and N-methyl-N-vinylformamide,
maleic anhydride,
vinylamine,
N-vinyllactams comprising a cyclic alkyl group containing from 4 to 9 carbon atoms, such as N-vinylpyrrolidone, N-butyrolactam and N-vinylcaprolactam,
vinyl alcohol of formula $CH_2=CHOH$,
water-soluble vinyl monomers of formula (B) below:

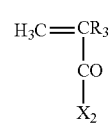
(B)

in which:
$R_3$ is chosen from H, $-CH_3$, $-C_2H_5$ and $-C_3H_7$,
$X_2$ is chosen from alkyl oxides of the type $-OR_4$ where $R_4$ is a linear or branched, saturated or unsaturated hydrocarbon-based radical containing from 1 to 6 carbon atoms, optionally substituted with a halogen (iodine, bromine, chlorine or fluorine) atom; a hydroxyl ($-OH$) group; ether.

Mention is made, for example, of glycidyl (meth)acrylate, hydroxyethyl methacrylate, and (meth)acrylates of ethylene glycol, of diethylene glycol or of polyalkylene glycol.

Among the hydrophobic co-monomers without a fatty chain, mention may be made, for example, of:
styrene and derivatives thereof, such as 4-butylstyrene, α-methylstyrene and vinyltoluene;
vinyl acetate of formula $CH_2=CH-OCOCH_3$;
vinyl ethers of formula $CH_2=CHOR$ in which R is a linear or branched, saturated or unsaturated hydrocarbon-based radical containing from 1 to 6 carbons;
acrylonitrile;
caprolactone;
vinyl chloride and vinylidene chloride;
silicone derivatives, which, after polymerization, result in silicone polymers such as methacryloxypropyltris(trimethylsiloxy)silane and silicone methacrylamides;
hydrophobic vinyl monomers of formula (C) below:

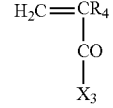
(C)

in which:
$R_4$ is chosen from H, $-CH_3$, $-C_2H_5$ and $-C_3H_7$;
$X_3$ is chosen from:
alkyl oxides of the type $-OR_5$ where $R_5$ is a linear or branched, saturated or unsaturated hydrocarbon-based radical containing from 1 to 6 carbon atoms.

Mention is made, for example, of methyl methacrylate, ethyl methacrylate, n-butyl (meth)acrylate, tert-butyl (meth)acrylate, cyclohexyl acrylate, isobornyl acrylate and 2-ethylhexyl acrylate.

The water-soluble or water-dispersible AMPS® polymers of the invention preferably have a molar mass ranging from 50 000 g/mol to 10 000 000 g/mol, preferably from 80 000 g/mol to 8 000 000 g/mol, and even more preferably from 100 000 g/mol to 7 000 000 g/mol.

As water-soluble or water-dispersible AMPS homopolymers suitable for use in the invention, mention may be made, for example, of crosslinked or non-crosslinked polymers of sodium acrylamido-2-methylpropanesulfonate, such as that used in the commercial product Simulgel 800 (CTFA name: Sodium Polyacryloyldimethyl Taurate), crosslinked ammonium acrylamido-2-methylpropanesulfonate polymers (INCI name: Ammonium Polyacryldimethyltauramide) such as those described in patent EP 0 815 928 B1 and such as the product sold under the trade name Hostacerin AMPS® by the company Clariant.

As water-soluble or water-dispersible AMPS copolymers in accordance with the invention, examples that may be mentioned include:

- crosslinked acrylamide/sodium acrylamido-2-methylpropanesulfonate copolymers, such as that used in the commercial product Sepigel 305® (CTFA name: Polyacrylamide/$C_{13}$-$C_{14}$ Isoparaffin/Laureth-7) or that used in the commercial product sold under the name Simulgel 600 (CTFA name: Acrylamide/Sodium acryloyldimethyltaurate/Isohexadecane/Polysorbate-80) by the company SEPPIC;
- copolymers of AMPS® and of vinylpyrrolidone or vinylformamide, such as that used in the commercial product sold under the name Aristoflex AVC® by the company Clariant (CTFA name: Ammonium Acryloyldimethyltaurate/VP copolymer) but neutralized with sodium hydroxide or potassium hydroxide;
- copolymers of AMPS® and of sodium acrylate, for instance the AMPS/sodium acrylate copolymer, such as that used in the commercial product sold under the name Simulgel EG® by the company SEPPIC;
- copolymers of AMPS® and of hydroxyethyl acrylate, for instance the AMPS®/hydroxyethyl acrylate copolymer, such as that used in the commercial product sold under the name Simulgel NS® by the company SEPPIC (CTFA name: Hydroxyethyl acrylate/Sodium acryloyldimethyltaurate copolymer (and) Squalane (and) Polysorbate 60), or such as the product sold under the name Sodium acrylamido-2-methylpropanesulfonate/ Hydroxyethyl acrylate copolymer, such as the commercial product Sepinov EMT 10 or under the trade name Sepinov EM (INCI name: Hydroxyethyl acrylate/Sodium acryloyldimethyltaurate copolymer).

As preferred water-soluble or water-dispersible AMPS copolymers in accordance with the invention, mention may be made of copolymers of AMPS® and of hydroxyethyl acrylate.

In general, an aqueous phase according to the invention may comprise from 0.1% to 8% by weight, preferably from 0.2% to 5% by weight and more preferentially from 0.7% to 5% by weight of solids of polyacrylamide(s) and/or of crosslinked and/or neutralized 2-acrylamido-2-methylpropanesulfonic acid polymer(s) and copolymer(s) relative to its total weight.

II.B. 3 Modified or Unmodified Carboxyvinyl Polymers

The modified or unmodified carboxyvinyl polymers may be copolymers derived from the polymerization of at least one monomer (a) chosen from α,β-ethylenically unsaturated carboxylic acids or esters thereof, with at least one ethylenically unsaturated monomer (b) comprising a hydrophobic group.

The term "copolymers" means both copolymers obtained from two types of monomer and those obtained from more than two types of monomer, such as terpolymers obtained from three types of monomer.

Their chemical structure more particularly comprises at least one hydrophilic unit and at least one hydrophobic unit. The term "hydrophobic group or unit" means a radical with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferably, these copolymers are chosen from copolymers derived from the polymerization:

of at least one monomer of formula (1) below:

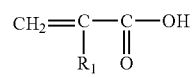

(1)

in which $R_1$ denotes H or $CH_3$ or $C_2H_5$, i.e. acrylic acid, methacrylic acid or ethacrylic acid monomers, and of at least one monomer of unsaturated carboxylic acid ($C_{10}$-$C_{30}$)alkyl ester type corresponding to the monomer of formula (2) below:

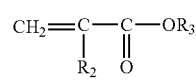

(2)

in which $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_{10}$-$C_{30}$ and preferably $C_{12}$-$C_{22}$ alkyl radical.

The unsaturated carboxylic acid ($C_{10}$-$C_{30}$)alkyl esters are preferably chosen from lauryl acrylate, stearyl acrylate, decyl acrylate, isodecyl acrylate and dodecyl acrylate, and the corresponding methacrylates, such as lauryl methacrylate, stearyl methacrylate, decyl methacrylate, isodecyl methacrylate and dodecyl methacrylate, and mixtures thereof.

According to a preferred embodiment, these polymers are crosslinked.

Among the copolymers of this type that will be used more particularly are polymers derived from the polymerization of a monomer mixture comprising:

essentially acrylic acid, an ester of formula (2) described above in which $R_2$ denotes H or $CH_3$, $R_3$ denoting an alkyl radical containing from 12 to 22 carbon atoms, and a crosslinking agent, which is a well-known copolymerizable unsaturated polyethylenic monomer, such as diallyl phthalate, allyl (meth)acrylate, divinylbenzene, (poly)ethylene glycol dimethacrylate and methylenebisacrylamide.

Among the copolymers of this type, use will more particularly be made of those consisting of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among the abovementioned polymers, the ones that are most particularly preferred according to the present invention are acrylate/$C_{10}$-$C_{30}$-alkyl acrylate copolymers (INCI name: Acrylates/$C_{10\text{-}30}$ Alkyl acrylate Crosspolymer) such as the products sold by the company Lubrizol under the trade names Pemulen TR-1, Pemulen TR-2, Carbopol 1382, Carbopol EDT 2020 and Carbopol Ultrez 20 Polymer, and even more preferentially Pemulen TR-2.

Among the modified or unmodified carboxyvinyl polymers, mention may also be made of sodium polyacrylates such as those sold under the name Cosmedia SP® containing 90% solids and 10% water, or Cosmedia SPL® as an inverse emulsion containing about 60% solids, an oil (hydrogenated polydecene) and a surfactant (PPG-5 Laureth-5), both sold by the company Cognis.

Mention may also be made of partially neutralized sodium polyacrylates that are in the form of an inverse emulsion comprising at least one polar oil, for example the product sold under the name Luvigel® EM sold by the company BASF.

The modified or unmodified carboxyvinyl polymers may also be chosen from crosslinked (meth)acrylic acid homopolymers.

For the purposes of the present patent application, the term "(meth)acrylic" means "acrylic or methacrylic".

Examples that may be mentioned include the products sold by Lubrizol under the names Carbopol 910, 934, 940, 941, 934 P, 980, 981, 2984, 5984 and Carbopol Ultrez 10 Polymer, or by 3V-Sigma under the name Synthalen® K, Synthalen® L or Synthalen® M.

Among the modified or unmodified carboxyvinyl polymers, mention may be made in particular of Carbopol (INCI name: carbomer) and Pemulen (CTFA name: Acrylates/$C_{10-30}$ alkyl acrylate crosspolymer) sold by the company Lubrizol.

The modified or unmodified carboxyvinyl polymers may be present in a proportion of from 0.1% to 5% by weight of solids relative to the weight of the aqueous phase, in particular from 0.3% to 1% by weight and preferably between 0.4% and 1% by weight, relative to the weight of the aqueous phase.

Advantageously, a composition according to the invention comprises a synthetic polymeric hydrophilic gelling agent chosen from 2-acrylamido-2-methylpropanesulfonic acid polymers and copolymers.

According to a preferred variant, the synthetic polymeric hydrophilic gelling agent is a crosslinked sodium polyacrylate or, preferably, a copolymer of 2-acrylamido-2-methylpropanesulfonic acid and of hydroxyethyl acrylate.

According to another preferred variant, the synthetic polymeric hydrophilic gelling agent is at least one ammonium 2-acrylamido-2-methylpropanesulfonate polymer.

III. Other Hydrophilic Gelling Agents

These gelling agents are more particularly chosen from mixed silicates and fumed silicas.

III.A. Mixed Silicate

For the purposes of the present invention, the term "mixed silicate" means all silicates of natural or synthetic origin containing several (two or more) types of cations chosen from alkali metals (for example Na, Li, K) or alkaline-earth metals (for example Be, Mg, Ca), transition metals and aluminium.

According to a particular embodiment, the mixed silicate(s) are in the form of solid particles containing at least 10% by weight of at least one silicate relative to the total weight of the particles. In the rest of the present description, these particles are referred to as "silicate particles".

Preferably, the silicate particles contain less than 1% by weight of aluminium relative to the total weight of the particles. Even more preferably, they contain from 0 to 1% by weight of aluminium relative to the total weight of the particles.

Preferably, the silicate particles contain at least 50% by weight of silicate and better still at least 70% by weight relative to the total weight of the particles. Particles containing at least 90% by weight of silicates, relative to the total weight of the particles, are particularly preferred.

In particular, it is an alkali metal or alkaline-earth metal, aluminium or iron silicate or mixture of silicates.

Preferably, it is sodium, magnesium and/or lithium silicate.

To ensure good cosmetic properties, these silicates are generally in a finely divided form, and in particular in the form of particles with a mean size ranging from 2 nm to 1 μm (from 2 nm to 1000 nm), preferably from 5 nm to 600 nm and even more preferentially from 20 to 250 nm.

The silicate particles may have any form, for example the form of spheres, flakes, needles, platelets, discs, leaflets, or totally random forms. Preferably, the silicate particles are in the form of discs or leaflets.

Thus, the term "mean size" of the particles means the numerical mean size of the largest dimension (length) that it is possible to measure between two diametrically opposite points on an individual particle. The size may be determined, for example, by transmission electron microscopy or by measuring the specific surface area via the BET method or by laser particle size analysis.

When the particles are in the form of discs or leaflets, they generally have a thickness ranging from about 0.5 nm to 5 nm.

The silicate particles may consist of an alloy with metal or metalloid oxides, obtained, for example, by thermal melting of the various constituents thereof. When the particles also comprise such a metal or metalloid oxide, this oxide is preferably chosen from silicon, boron or aluminium oxide.

According to a particular embodiment of the invention, the silicates are phyllosilicates, namely silicates having a structure in which the $SiO_4$ tetrahedra are organized in leaflets between which the metal cations are enclosed.

The mixed silicates that are suitable for use in the invention may be chosen, for example, from montmorillonites, hectorites, bentonites, beidellite and saponites. According to a preferred embodiment of the invention, the mixed silicates used are more particularly chosen from hectorites and bentonites, and better still from laponites.

A family of silicates that is particularly preferred in the compositions of the present invention is thus the laponite family. Laponites are sodium magnesium silicates also possibly containing lithium, which have a layer structure similar to that of montmorillonites. Laponite is the synthetic form of the natural mineral known as hectorite. The synthetic origin of this family of silicates is of considerable advantage over the natural form, since it allows good control of the composition of the product. In addition, laponites have the advantage of having a particle size that is much smaller than that of the natural minerals hectorite and bentonite.

Laponites that may especially be mentioned include the products sold under the following names: Laponite® XLS, Laponite® XLG, Laponite® RD, Laponite® RDS, Laponite® XL21 (these products are sodium magnesium silicates and sodium lithium magnesium silicates) by the company Rockwood Additives Limited.

Such gelling agents may be used in a proportion of from 0.1% to 8% by weight of solids relative to the total weight of the aqueous phase, especially from 0.1% to 5% by weight and in particular from 0.5% to 3% by weight, relative to the total weight of the aqueous phase.

III.B. Hydrophilic Fumed Silica

The fumed silicas according to the present invention are hydrophilic.

The hydrophilic fumed silicas are obtained by pyrolysis of silicon tetrachloride ($SiCl_4$) in a continuous flame at 1000° C. in the presence of hydrogen and oxygen. Among the fumed silicas of hydrophilic nature that may be used according to the present invention, mention may be made in particular of those sold by the company Degussa or Evonik Degussa under the trade names Aerosil® 90, 130, 150, 200, 300 and 380 or alternatively by the company Cabot under the name Carbosil H5.

Such gelling agents may be used in a proportion of from 0.1% to 10% by weight of solids relative to the total weight of the aqueous phase, especially from 0.1% to 5% by weight and in particular from 0.5% to 3% by weight, relative to the total weight of the aqueous phase.

Lipophilic Gelling Agent

For the purposes of the present invention, the term "lipophilic gelling agent" means a compound that is capable of gelling the oily phase of the compositions according to the invention.

The gelling agent is lipophilic and is thus present in the oily phase of the composition.

The gelling agent is liposoluble or lipodispersible.

As emerges from the text hereinbelow, the lipophilic gelling agent is advantageously chosen from particulate gelling agents, organopolysiloxane elastomers, semi-crystalline polymers, dextrin esters and hydrogen bonding polymers, and mixtures thereof.

I. Particulate Gelling Agents

The particulate gelling agent used in the composition according to the invention is in the form of particles, preferably spherical particles.

As representative lipophilic particulate gelling agents that are suitable for use in the invention, mention may be made most particularly of polar and apolar waxes, modified clays, and silicas such as fumed silicas and hydrophobic silica aerogels.

Waxes

The term "wax" under consideration in the context of the present invention generally means a lipophilic compound that is solid at room temperature (25° C.), with a solid/liquid reversible change of state, having a melting point of greater than or equal to 30° C., which may be up to 200° C. and in particular up to 120° C.

For the purposes of the invention, the melting point corresponds to the temperature of the most endothermic peak observed in thermal analysis (DSC) as described in the standard ISO 11357-3; 1999. The melting point of the wax may be measured using a differential scanning calorimeter (DSC), for example the calorimeter sold under the name MDSC 2920 by the company TA Instruments.

The measuring protocol is as follows:

A 5 mg sample of wax placed in a crucible is subjected to a first temperature increase from −20° C. to 100° C., at a heating rate of 10° C./minute, and then is cooled from 100° C. to −20° C. at a cooling rate of 10° C./minute and is finally subjected to a second temperature rise from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature of animal, plant, mineral or synthetic origin, and mixtures thereof.

The waxes, for the purposes of the invention, may be those used generally in the cosmetic or dermatological fields. They may in particular be polar or apolar, and hydrocarbon-based, silicone and/or fluoro waxes, optionally comprising ester or hydroxyl functions. They may also be of natural or synthetic origin.

a) Apolar Waxes

For the purposes of the present invention, the term "apolar wax" means a wax whose solubility parameter at 25° C. as defined below, $\delta_a$, is equal to 0 $(J/cm^3)^{1/2}$.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The apolar waxes are in particular hydrocarbon-based waxes constituted solely of carbon and hydrogen atoms, and free of heteroatoms such as N, O, Si and P.

The apolar waxes are chosen from microcrystalline waxes, paraffin waxes, ozokerite and polyethylene waxes, and mixtures thereof.

An ozokerite that may be mentioned is Ozokerite Wax SP 1020 P.

As microcrystalline waxes that may be used, mention may be made of Multiwax W 445® sold by the company Sonneborn, and Microwax HW® and Base Wax 30540® sold by the company Paramelt, and Cerewax® No. 3 sold by the company Baerlocher.

As microwaxes that may be used in the compositions according to the invention as apolar wax, mention may be made in particular of polyethylene microwaxes such as those sold under the names Micropoly 200®, 220®, 220L® and 250S® by the company Micro Powders.

Polyethylene waxes that may be mentioned include Performalene 500-L Polyethylene and Performalene 400 Polyethylene sold by New Phase Technologies, and Asensa® SC 211 sold by the company Honeywell.

b) Polar Wax

For the purposes of the present invention, the term "polar wax" means a wax whose solubility parameter at 25° C., δa, is other than 0 $(J/cm^3)^{1/2}$.

In particular, the term "polar wax" means a wax whose chemical structure is formed essentially from, or even consists of, carbon and hydrogen atoms, and comprising at least one highly electronegative heteroatom such as an oxygen, nitrogen, silicon or phosphorus atom.

The polar waxes may in particular be hydrocarbon-based, fluoro or silicone waxes.

Preferentially, the polar waxes may be hydrocarbon-based waxes.

The term "hydrocarbon-based wax" is intended to mean a wax formed essentially from, or even constituted of, carbon and hydrogen atoms, and optionally oxygen and nitrogen atoms, and that does not contain any silicon or fluorine atoms. It may also contain alcohol, ester, ether, carboxylic acid, amine and/or amide groups.

According to the invention, the term "ester wax" is intended to mean a wax comprising at least one ester function. According to the invention, the term "alcohol wax" is intended to mean a wax comprising at least one alcohol function, i.e. comprising at least one free hydroxyl (OH) group.

The following may especially be used as ester wax:
ester waxes such as those chosen from:
i) waxes of formula $R_1COOR_2$ in which $R_1$ and $R_2$ represent linear, branched or cyclic aliphatic chains in which the number of atoms ranges from 10 to 50, which may contain a heteroatom such as O, N or P and whose melting point ranges from 25 to 120° C.;
ii) bis(1,1,1-trimethylolpropane) tetrastearate, sold under the name Hest 2T-4S® by the company Heterene;
iii) diester waxes of a dicarboxylic acid of general formula $R^3$—(—OCO—$R^4$—COO—$R^5$), in which $R^3$ and $R^5$ are identical or different, preferably identical, and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not comprise one or more unsaturations and which is preferably linear and unsaturated;
iv) mention may also be made of the waxes obtained by catalytic hydrogenation of animal or vegetable oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol;
v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumac wax, montan wax, orange wax, laurel wax, hydrogenated jojoba wax, sunflower wax, lemon wax, olive wax or berry wax.

According to another embodiment, the polar wax may be an alcohol wax. According to the invention, the term "alcohol wax" means a wax comprising at least one alcohol function, i.e. comprising at least one free hydroxyl (OH) group. Alcohol waxes that may be mentioned include for example the $C_{30-50}$ alcohol wax Performacol® 550 Alcohol sold by the company New Phase Technologies, stearyl alcohol and cetyl alcohol.

It is also possible to use silicone waxes, which may advantageously be substituted polysiloxanes, preferably of low melting point.

The term "silicone wax" is intended to mean an oil comprising at least one silicon atom, and in particular comprising Si—O groups.

Among the commercial silicone waxes of this type, mention may be made in particular of those sold under the names Abilwax 9800, 9801 or 9810 (Goldschmidt), KF910 and KF7002 (Shin-Etsu), or 176-1118-3 and 176-11481 (General Electric).

The silicone waxes that may be used may also be alkyl or alkoxy dimethicones, and also ($C_{20}$-$C_{60}$)alkyl dimethicones, in particular ($C_{30}$-$C_{45}$)alkyl dimethicones, such as the silicone wax sold under the name SF-1642 by the company GE-Bayer Silicones or $C_{30-45}$ alkyl dimethylsilyl polypropylsilsesquioxane under the name SW-8005® C30 Resin Wax sold by the company Dow Corning.

In the context of the present invention, particularly advantageous waxes that may be mentioned include polyethylene waxes, jojoba wax, candelilla wax and silicone waxes, in particular candelilla wax.

They may be present in the oily phase in a proportion of from 0.5% to 30% by weight relative to the weight of the oily phase, for example between 5% and 20% of the oily phase and more particularly from 2% to 15% by weight relative to the weight of the oily phase.

Modified Clays

The composition according to the invention may comprise at least one lipophilic clay.

The clays may be natural or synthetic, and they are made lipophilic by treatment with an alkylammonium salt such as a $C_{10}$ to $C_{22}$ ammonium chloride, for example distearyldimethylammonium chloride.

They may be chosen from bentonites, in particular hectorites and montmorillonites, beidellites, saponites, nontronites, sepiolites, biotites, attapulgites, vermiculites and zeolites.

They are preferably chosen from hectorites.

Hectorites modified with a $C_{10}$ to $C_{22}$ ammonium chloride, such as hectorite modified with distearyldimethylammonium chloride, for instance the product sold under the name Bentone 38V® by the company Elementis or bentone gel in isododecane sold under the name Bentone Gel ISD V® (87% isododecane/10% disteardimonium hectorite/3% propylene carbonate) by the company Elementis, are preferably used as lipophilic clays.

Lipophilic clay may especially be present in a content ranging from 0.1% to 15% by weight, in particular from 0.5% to 10% and more particularly from 1% to 10% by weight relative to the total weight of the oily phase.

Silicas

The oily phase of a composition according to the invention may also comprise, as gelling agent, a fumed silica or silica aerogel particles.

a) Fumed Silica

Fumed silica which has undergone a hydrophobic surface treatment is most particularly suitable for use in the invention. Specifically, it is possible to chemically modify the surface of the silica, by chemical reaction generating a reduced number of silanol groups present at the surface of the silica. It is possible in particular to replace silanol groups with hydrophobic groups: a hydrophobic silica is then obtained.

The hydrophobic groups may be:
trimethylsiloxyl groups, which are obtained in particular by treating fumed silica in the presence of hexamethyldisilazane. Silicas thus treated are known as Silica Silylate according to the CTFA ($8^{th}$ edition, 2000). They are sold, for example, under the references Aerosil R812® by the company Degussa and Cab-O-Sil TS-530® by the company Cabot.
dimethylsilyloxyl or polydimethylsiloxane groups, which are obtained in particular by treating fumed silica in the presence of polydimethylsiloxane or dimethyldichlorosilane. Silicas thus treated are known as Silica dimethyl silylate according to the CTFA (8th edition, 2000). They are sold, for example, under the references Aerosil R972® and Aerosil R974® by the company Degussa, and Cab-O-Sil TS-610® and Cab-O-Sil TS-720® by the company Cabot.

The fumed silicas may be present in a composition according to the present invention in a content of between 0.1% and 40% by weight, more particularly between 1% and 15% by weight and even more particularly between 2% and 10% by weight relative to the total weight of the oily phase.

b) Hydrophobic Silica Aerogels

The oily phase of a composition according to the invention may also comprise, as gelling agent, at least silica aerogel particles.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., *Sol-Gel Science*, New York: Academic Press, 1990.

The hydrophobic silica aerogel particles used in the present invention have a specific surface area per unit mass (SM) ranging from 500 to 1500 $m^2/g$, preferably from 600 to 1200 $m^2/g$ and better still from 600 to 800 $m^2/g$, and a size expressed as the volume-mean diameter (D[0.5]) ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size expressed as volume-mean diameter (D[0.5]) ranging from 1 to 30 µm, preferably from 5 to 25 µm, better still from 5 to 20 µm and even better still from 5 to 15 µm.

The specific surface area per unit mass may be determined by the nitrogen absorption method, known as the BET (Brunauer-Emmett-Teller) method, described in the *Journal of the American Chemical Society*, vol. 60, page 309, February 1938, which corresponds to International Standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., *Light Scattering by Small Particles*, Chapters 9 and 10, Wiley, New York, 1957.

According to an advantageous embodiment, the hydrophobic silica aerogel particles used in the present invention have a specific surface area per unit of mass (SM) ranging from 600 to 800 $m^2/g$.

The silica aerogel particles used in the present invention may advantageously have a tapped density p ranging from 0.02 $g/cm^3$ to 0.10 $g/cm^3$, preferably from 0.03 $g/cm^3$ to 0.08 $g/cm^3$ and in particular ranging from 0.05 $g/cm^3$ to 0.08 $g/cm^3$.

In the context of the present invention, this density, known as the tapped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 tapping actions (this operation is repeated until the difference in volume between two consecutive tests is less than 2%); the final volume Vf of tapped powder is then measured directly on the measuring cylinder. The tapped density is determined by the ratio m/Vf, in this instance 40/Vf (Vf being expressed in $cm^3$ and m in g).

According to one preferred embodiment, the hydrophobic silica aerogel particles used in the present invention have a specific surface area per unit of volume SV ranging from 5 to 60 $m^2/cm^3$, preferably from 10 to 50 $m^2/cm^3$ and better still from 15 to 40 $m^2/cm^3$.

The specific surface area per unit of volume is given by the relationship: $S_V = S_M \times \rho$; where $\rho$ is the tapped density, expressed in $g/cm^3$, and $S_M$ is the specific surface area per unit of mass, expressed in $m^2/g$, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorbing capacity measured at the wet point, noted Wp, corresponds to the amount of oil that needs to be added to 100 g of particles in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The aerogels used according to the present invention are aerogels of hydrophobic silica, preferably of silylated silica (INCI name: silica silylate).

The term "hydrophobic silica" means any silica whose surface is treated with silylating agents, for example with halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will preferably be made of hydrophobic silica aerogel particles surface-modified with trimethylsilyl groups, preferably of the INCI name Silica silylate.

As hydrophobic silica aerogels that may be used in the invention, an example that may be mentioned is the aerogel sold under the name VM-2260 or VM-2270 (INCI name: Silica silylate) by the company Dow Corning, the particles of which have a mean size of about 1000 microns and a specific surface area per unit of mass ranging from 600 to 800 $m^2/g$.

Mention may also be made of the aerogels sold by the company Cabot under the references Aerogel TLD 201, Aerogel OGD 201 and Aerogel TLD 203, Enova® Aerogel MT 1100 and Enova Aerogel MT 1200.

Use will preferably be made of the aerogel sold under the name VM-2270 (INCI name: Silica silylate) by the company Dow Corning, the particles of which have an average size ranging from 5-15 microns and a specific surface area per unit of mass ranging from 600 to 800 m²/g.

Such an aerogel advantageously makes it possible to promote the resistance of the deposit to sebum and to sweat.

Preferably, the hydrophobic silica aerogel particles are present in the composition according to the invention in a solids content ranging from 0.1% to 8% by weight, preferably from 0.2% to 5% by weight and preferably from 0.2% to 1.5% by weight relative to the total weight of the oily phase.

II. Organopolysiloxane Elastomer

The organopolysiloxane elastomer that may be used as lipophilic gelling agent has the advantage of giving the composition according to the invention good application properties. It affords a very soft feel and a matt effect after application, which is advantageous especially for application to the skin. It may also allow efficient filling of the hollows present on keratin materials.

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has a limited ability to extend and to contract. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane comprising hydroxyl end groups and a diorganopolysiloxane containing at least one hydrogen bonded to silicon, especially in the presence of an organotin; or by crosslinking condensation reaction of a diorganopolysiloxane comprising hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of dimethylpolysiloxane comprising dimethylvinyl siloxy end groups and of methylhydrogenopolysiloxane comprising trimethylsiloxy end groups, in the presence of a platinum catalyst.

Compound (A) is the base reagent for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, in particular a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) can thus be chosen from methylhydrogenopolysiloxanes comprising trimethylsiloxy end groups, dimethylsiloxane-methylhydrosiloxane copolymers comprising trimethylsiloxy end groups, and dimethylsiloxane-methylhydrosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located at any position on the organopolysiloxane molecule but are preferably located at the ends of the organopolysiloxane molecule. The organopolysiloxane (B) may have a branched-chain, linear-chain, cyclic or network structure but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinylsiloxy end groups, dimethylsiloxane-diphenylsiloxane-methylvinyl siloxane copolymers comprising dimethylvinylsiloxy end groups, dimethylsiloxane-methylvinylsiloxane copolymers comprising trimethylsiloxy end groups, dimethylsiloxane-methylphenyl siloxane-methylvinyl siloxane copolymers comprising trimethylsiloxy end groups, methyl(3,3,3-trifluoropropyl)polysiloxanes comprising dimethylvinylsiloxy end groups, and dimethylsiloxane-methyl(3,3,3-trifluoropropyl)siloxane copolymers comprising dimethylvinylsiloxy end groups.

In particular, the organopolysiloxane elastomer can be obtained by reaction of dimethylpolysiloxane comprising dimethylvinylsiloxy end groups and of methylhydrogenopolysiloxane comprising trimethylsiloxy end groups, in the presence of a platinum catalyst.

Advantageously, the sum of the number of ethylenic groups per molecule of compound (B) and of the number of hydrogen atoms bonded to silicon atoms per molecule of compound (A) is at least 5.

It is advantageous for compound (A) to be added in an amount such that the molecular ratio of the total amount of hydrogen atoms bonded to silicon atoms in compound (A) to the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units. Thus, according to one particular mode of the invention, the composition comprises an organopolysiloxane elastomer free of polyoxyalkylene units and of polyglyceryl units.

In particular, the silicone elastomer used in the present invention is chosen from Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name).

The organopolysiloxane elastomer particles may be conveyed in the form of a gel formed from an elastomeric organopolysiloxane included in at least one hydrocarbon-based oil and/or one silicone oil. In these gels, the organopolysiloxane particles are often non-spherical particles.

Non-emulsifying elastomers are described especially in patents EP 242 219, EP 285 886 and EP 765 656 and in patent application JP-A-61-194009.

The silicone elastomer is generally in the form of a gel, a paste or a powder, but advantageously in the form of a gel in which the silicone elastomer is dispersed in a linear silicone oil (dimethicone) or cyclic silicone oil (e.g.: cyclopentasiloxane), advantageously in a linear silicone oil.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, optionally modified with optionally fluorinated aliphatic groups, or with functional groups such as hydroxyl, thiol and/or amine groups.

Mention may be made especially of the compounds having the following INCI names:

dimethicone/vinyl dimethicone crosspolymer, such as USG-105 and USG-107A from the company Shin-Etsu; DC9506 and DC9701 from the company Dow Corning;

dimethicone/vinyl dimethicone crosspolymer (and) dimethicone, such as KSG-6 and KSG-16 from the company Shin-Etsu;

dimethicone/vinyl dimethicone crosspolymer (and) cyclopentasiloxane, such as KSG-15;

cyclopentasiloxane (and) dimethicone crosspolymer, such as DC9040, DC9045 and DC5930 from the company Dow Corning;

dimethicone (and) dimethicone crosspolymer, such as DC9041 from the company Dow Corning.

dimethicone (and) dimethicone crosspolymer, such as Dow Corning EL-9240® Silicone Elastomer Blend from the company Dow Corning (mixture of polydimethylsiloxane crosslinked with hexadiene/polydimethylsiloxane (2 cSt));

$C_{4-24}$ alkyl dimethicone/divinyl dimethicone crosspolymer, such as NuLastic Silk MA from the company Alzo.

As examples of silicone elastomers dispersed in a linear silicone oil that may advantageously be used according to the invention, mention may especially be made of the following references:

dimethicone/vinyl dimethicone crosspolymer (and) dimethicone, such as KSG-6 and KSG-16 from the company Shin-Etsu;

dimethicone (and) dimethicone crosspolymer, such as DC9041 from the company Dow Corning; and dimethicone (and) dimethicone crosspolymer, such as Dow Corning EL-9240® Silicone Elastomer Blend from the company Dow Corning (mixture of polydimethylsiloxane crosslinked with hexadiene/polydimethylsiloxane (2 cSt)).

According to a preferred embodiment, the composition according to the invention comprises at least one crosslinked silicone elastomer having the INCI name "dimethicone crosspolymer" or "dimethicone (and) dimethicone crosspolymer", with, preferably, a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 by the company Dow Corning or the mixture of polydimethylsiloxane crosslinked with hexadiene/polydimethylsiloxane (2 cSt) sold under the name EL-9240® by the company Dow Corning.

According to a particularly preferred embodiment, the composition according to the invention comprises at least one crosslinked silicone elastomer having the INCI name "dimethicone (and) dimethicone crosspolymer", preferably with a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 by the company Dow Corning.

The organopolysiloxane elastomer particles may also be used in powder form: mention may be made especially of the powders sold under the names Dow Corning 9505 Powder and Dow Corning 9506 Powder by the company Dow Corning, these powders having the INCI name: dimethicone/vinyl dimethicone crosspolymer.

The organopolysiloxane powder may also be coated with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, and have the INCI name: vinyl dimethicone/methicone silsesquioxane crosspolymer.

As examples of organopolysiloxane powders coated with silsesquioxane resin that may advantageously be used according to the invention, mention may be made especially of the reference KSP-100 from the company Shin-Etsu.

As preferred lipophilic gelling agent of organopolysiloxane elastomer type, mention may be made especially of crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), and in particular Dimethicone Crosspolymer (INCI name).

The organopolysiloxane elastomer may be present in a composition of the present invention in a content of between 0.1% and 35% by weight of solids, especially between 1% and 20% and more particularly between 2% and 10% by weight relative to the total weight of the composition.

III. Semi-Crystalline Polymers

The composition according to the invention may comprise at least one semi-crystalline polymer. Preferably, the semi-crystalline polymer has an organic structure, and a melting point of greater than or equal to 30° C.

For the purposes of the invention, the term "semi-crystalline polymer" is intended to mean polymers comprising a crystallizable portion and an amorphous portion and having a first-order reversible change of phase temperature, in particular of melting point (solid-liquid transition). The crystallizable part is either a side chain (or pendent chain) or a block in the backbone.

When the crystallizable portion of the semi-crystalline polymer is a block of the polymer backbone, this crystallizable block has a chemical nature different than that of the amorphous blocks; in this case, the semi-crystalline polymer is a block copolymer, for example of the diblock, triblock or multiblock type. When the crystallizable part is a chain that is pendent on the backbone, the semi-crystalline polymer may be a homopolymer or a copolymer.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is greater than or equal to 30° C. and less than 70° C.

The semi-crystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5 or 10° C. per minute (the melting point under consideration is the point corresponding to the temperature of the most endothermic peak in the thermogram).

The semi-crystalline polymer(s) according to the invention preferably have a melting point that is higher than the temperature of the keratinous support intended to receive said composition, in particular the skin, the lips or the eyebrows.

According to the invention, the semi-crystalline polymers are advantageously soluble in the fatty phase, especially to at least 1% by weight, at a temperature that is higher than their melting point. Besides the crystallizable chains or blocks, the blocks of the polymers are amorphous.

For the purposes of the invention, the term "crystallizable chain or block" is intended to mean a chain or block which, if it were alone, would change from the amorphous state to the crystalline state reversibly, depending on whether the temperature is above or below the melting point. For the purposes of the invention, a chain is a group of atoms, which are pendent or lateral relative to the polymer backbone. A "block" is a group of atoms belonging to the backbone, this group constituting one of the repeating units of the polymer.

Preferably, the polymer backbone of the semi-crystalline polymers is soluble in the fatty phase at a temperature above their melting point.

Preferably, the crystallizable blocks or chains of the semi-crystalline polymers represent at least 30% of the total weight of each polymer and better still at least 40%. The semi-crystalline polymers containing crystallizable side chains are homopolymers or copolymers. The semi-crystalline polymers of the invention containing crystallizable blocks are block or multiblock copolymers. They may be obtained via polymerization of a monomer containing reactive double bonds (or ethylenic bonds) or via polycondensation. When the polymers of the invention are polymers containing crystallizable side chains, these side chains are advantageously in random or statistical form.

Preferably, the semi-crystalline polymers of the invention are of synthetic origin.

According to a preferred embodiment, the semi-crystalline polymer is chosen from:
  homopolymers and copolymers comprising units resulting from the polymerization of one or more monomers bearing crystallizable hydrophobic side chain(s),
  polymers bearing in the backbone at least one crystallizable block,
  polycondensates of aliphatic or aromatic or aliphatic/aromatic polyester type,
  copolymers of ethylene and propylene prepared via metallocene catalysis, and
  acrylate/silicone copolymers.

The semi-crystalline polymers that may be used in the invention may be chosen in particular from:
  block copolymers of polyolefins of controlled crystallization, whose monomers are described in EP 0 951 897,
  polycondensates, in particular of aliphatic or aromatic or aliphatic/aromatic polyester type,
  copolymers of ethylene and propylene prepared via metallocene catalysis,
  homopolymers or copolymers bearing at least one crystallizable side chain and homopolymers or copolymers bearing in the backbone at least one crystallizable block, such as those described in document U.S. Pat. No. 5,156,911, such as the ($C_{10}$-$C_{30}$)alkyl polyacrylates corresponding to the Intelimer® products from the company Landec described in the brochure Intelimer® Polymers, Landec IP22 (Rev. 4-97), for example the product Intelimer® IPA 13-1 from the company Landec, which is a polystearyl acrylate with a molecular weight of about 145 000 and a melting point of 49° C.,
  homopolymers or copolymers bearing at least one crystallizable side chain, in particular containing fluoro group(s), as described in document WO 01/19333,
  acrylate/silicone copolymers, such as copolymers of acrylic acid and of stearyl acrylate bearing polydimethylsiloxane grafts, copolymers of stearyl methacrylate bearing polydimethylsiloxane grafts, copolymers of acrylic acid and of stearyl methacrylate bearing polydimethylsiloxane grafts, copolymers of methyl methacrylate, butyl methacrylate, 2-ethylhexyl acrylate and stearyl methacrylate bearing polydimethylsiloxane grafts. Mention may be made in particular of the copolymers sold by the company Shin-Etsu under the names KP-561 (CTFA name: acrylates/dimethicone), KP-541 (CTFA name: acrylates/dimethicone and isopropyl alcohol), KP-545 (CTFA name: acrylates/dimethicone and cyclopentasiloxane),
and mixtures thereof.

Preferably, the amount of semi-crystalline polymer(s), preferably chosen from semi-crystalline polymers bearing crystallizable side chains, represents from 0.1% to 30% by weight of solids relative to the total weight of the oily phase, for example from 0.5% to 25% by weight, better still from 5% to 20% or even from 5% to 12% by weight, relative to the total weight of the oily phase.

IV. Dextrin Esters

The composition according to the invention may comprise as lipophilic gelling agent at least one dextrin ester.

In particular, the composition preferably comprises at least one preferably $C_{12}$ to $C_{24}$ and in particular $C_{14}$ to $C_{18}$ fatty acid ester of dextrin, or mixtures thereof.

Preferably, the dextrin ester is an ester of dextrin and of a $C_{12}$-$C_{18}$ and in particular $C_{14}$-$C_{18}$ fatty acid.

Preferably, the dextrin ester is chosen from dextrin myristate and/or dextrin palmitate, and mixtures thereof.

According to a particular embodiment, the dextrin ester is dextrin myristate, such as the product sold especially under the name Rheopearl MKL-2 by the company Chiba Flour Milling.

According to a preferred embodiment, the dextrin ester is dextrin palmitate. This product may be chosen, for example, from those sold under the names Rheopearl TL®, Rheopearl KL® and Rheopearl® KL2 by the company Chiba Flour Milling.

In a particularly preferred manner, the oily phase of a composition according to the invention may comprise from 0.1% to 30% by weight, preferably from 2% to 25% and preferably from 7.5% to 17% by weight of dextrin ester(s) relative to the total weight of the oily phase.

In a particularly preferred manner, the composition according to the invention may comprise between 0.1% and 10% by weight and preferably between 0.5% and 5% by weight of dextrin palmitate relative to the total weight of the oily phase. The dextrin palmitate may especially be the product sold under the names Rheopearl TL®, Rheopearl KL® or Rheopearl® KL2 by the company Chiba Flour Milling.

V. Hydrogen Bonding Polymers

As representatives of hydrogen bonding polymers that are suitable for use in the invention, mention may be made most particularly of polyamides and in particular hydrocarbon-based polyamides and silicone polyamides.

Polyamides

The oily phase of a composition according to the invention may comprise at least one polyamide chosen from hydrocarbon-based polyamides and silicone polyamides, and mixtures thereof.

Preferably, the total content of polyamide(s) is between 0.1% and 30% by weight expressed as solids, preferably between 0.1% and 20% by weight and preferably between 0.5% and 10% by weight relative to the total weight of the oily phase.

For the purposes of the invention, the term "polyamide" means a compound containing at least 2 repeating amide units, preferably at least 3 repeating amide units and better still 10 repeating amide units.

a) Hydrocarbon-Based Polyamide

The term "hydrocarbon-based polyamide" means a polyamide formed essentially of, indeed even consisting of, carbon and hydrogen atoms, and optionally of oxygen or nitrogen atoms, and not comprising any silicon or fluorine atoms. It may contain alcohol, ester, ether, carboxylic acid, amine and/or amide groups.

For the purposes of the invention, the term "functionalized chain" means an alkyl chain comprising one or more functional groups or reagents chosen especially from hydroxyl, ether, ester, oxyalkylene and polyoxyalkylene groups.

Advantageously, this polyamide of the composition according to the invention has a weight-average molecular mass of less than 100 000 g/mol especially ranging from 1000 to 100 000 g/mol, in particular less than 50 000 g/mol especially ranging from 1000 to 50 000 g/mol and more particularly ranging from 1000 to 30 000 g/mol, preferably from 2000 to 20 000 g/mol and better still from 2000 to 10 000 g/mol.

This polyamide is insoluble in water, especially at 25° C.

According to a first embodiment of the invention, the polyamide used is a polyamide of formula (I):

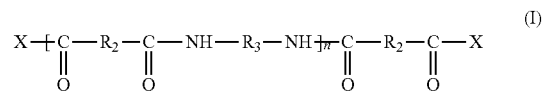

in which X represents a group —N(R$_1$)$_2$ or a group —OR$_1$ in which R$_1$ is a linear or branched C$_8$ to C$_{22}$, alkyl radical which may be identical or different, R$_2$ is a C$_{28}$-C$_{42}$ diacid dimer residue, R$_3$ is an ethylenediamine radical and n is between 2 and 5; and mixtures thereof.

According to a particular mode, the polyamide used is an amide-terminated polyamide of formula (Ia):

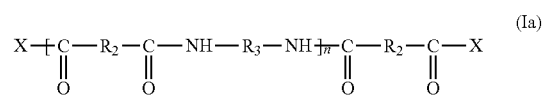

in which X represents a group —N(R$_1$)$_2$ in which R$_1$ is a linear or branched C$_8$ to C$_{22}$, alkyl radical which may be identical or different, R$_2$ is a C$_{28}$-C$_{42}$ diacid dimer residue, R$_3$ is an ethylenediamine radical and n is between 2 and 5; and mixtures thereof.

The oily phase of a composition according to the invention may also comprise, additionally in this case, at least one additional polyamide of formula (Ib):

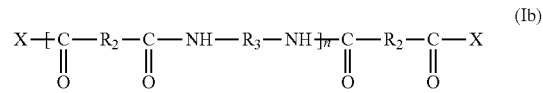

in which X represents a group —OR$_1$ in which R$_1$ is a linear or branched C$_8$ to C$_{22}$ and preferably C$_{16}$ to C$_{22}$, alkyl radical which may be identical or different, R$_2$ is a C$_{28}$-C$_{42}$ diacid dimer residue, R$_3$ is an ethylenediamine radical and n is between 2 and 5, such as the commercial products sold by the company Arizona Chemical under the names Uniclear 80 and Uniclear 100 or Uniclear 80 V, Uniclear 100 V and Uniclear 100 VG, the INCI name of which is Ethylenediamine/stearyl dimer dilinoleate copolymer.

b) Silicone Polyamide

The silicone polyamides are preferably solid at room temperature (25° C.) and atmospheric pressure (760 mmHg).

The silicone polyamides may preferentially be polymers comprising at least one unit of formula (III) or (IV):

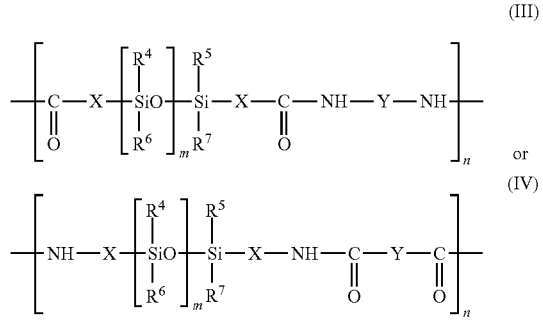

in which:

$R^4$, $R^5$, $R^6$ and $R^7$, which may be identical or different, represent a group chosen from:

saturated or unsaturated, $C_1$ to $C_{40}$ linear, branched or cyclic hydrocarbon-based groups, which may contain in their chain one or more oxygen, sulfur and/or nitrogen atoms, and which may be partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulfur and/or nitrogen atoms, the groups X, which may be identical or different, represent a linear or branched $C_1$ to $C_{30}$ alkylenediyl group, possibly containing in its chain one or more oxygen and/or nitrogen atoms, Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl and $C_1$ to $C_6$ aminoalkyl groups, or Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^8$ represents a linear or branched $C_1$ to $C_{50}$ alkyl group or a polyorganosiloxane chain, possibly comprising one or more ester, amide, urethane, thiocarbamate, urea, thiourea and/or sulfonamide groups, which may possibly be linked to another chain of the polymer, n is an integer ranging from 2 to 500 and preferably from 2 to 200, and m is an integer ranging from 1 to 1000, preferably from 1 to 700 and even better still from 6 to 200.

According to a particular mode, the silicone polyamide comprises at least one unit of formula (III) in which m ranges from 50 to 200, in particular from 75 to 150 and is preferably about 100.

More preferably, $R^4$, $R^5$, $R^6$ and $R^7$ independently represent a linear or branched $C_1$ to $C_{40}$ alkyl group, preferably a group $CH_3$, $C_2H_5$, n-$C_3H_7$ or an isopropyl group in formula (III).

As an example of silicone polymers that may be used, mention may be made of one of the silicone polyamides obtained in accordance with Examples 1 to 3 of document U.S. Pat. No. 5,981,680.

Mention may be made of the compounds sold by the company Dow Corning under the names DC 2-8179 (DP 100) and DC 2-8178 (DP 15), the INCI name of which is Nylon-611/dimethicone copolymer, i.e. Nylon-611/dimethicone copolymers. The silicone polymers and/or copolymers advantageously have a temperature of transition from the solid state to the liquid state ranging from 45° C. to 190° C. Preferably, they have a temperature of transition from the solid state to the liquid state ranging from 70 to 130° C. and better still from 80° C. to 105° C.

Preferably, the total content of polyamide(s) and/or silicone polyamide(s) is between 0.5% and 25% by weight of solids, in particular from 2% to 20% by weight and preferably between 2% and 12% by weight relative to the total weight of the oily phase.

Advantageously, the hydrogen bonding polymer is chosen from the ethylenediamine/stearyl dimer dilinoleate copolymer and Nylon-611/dimethicone copolymers.

According to an advantageous variant, a composition according to the invention comprises a lipophilic gelling agent chosen from particulate gelling agents, organopolysiloxane elastomers, semi-crystalline polymers, dextrin esters and hydrogen bonding polymers, and mixtures thereof, and in particular at least one organopolysiloxane elastomer.

Hydrophilic Gelling Agent/Lipophilic Gelling Agent System

As preferred synthetic polymeric hydrophilic gelling agents, mention may be made more particularly of 2-acrylamido-2-methylpropanesulfonic acid polymers, for instance AMPS, such as the ammonium 2-acrylamido-2-methylpropanesulfonate acid polymer sold under the trade name Hostacerin AMPS® by the company Clariant, and 2-acrylamido-2-methylpropanesulfonic acid copolymers and in particular copolymers of AMPS® and of hydroxyethyl acrylate, for instance the AMPS®/hydroxyethyl acrylate copolymer such as that used in the commercial product sold under the name Simulgel NS® by the company SEPPIC (CTFA name: Hydroxyethyl acrylate/Sodium acryloyldimethyltaurate copolymer (and) Squalane (and) Polysorbate 60), or such as the product sold under the name Sodium acrylamido-2-methylpropanesulfonate/Hydroxyethyl acrylate copolymer, such as the commercial product Sepinov EMT 10 (INCI name: Hydroxyethyl acrylate/Sodium acryloyldimethyltaurate copolymer).

As preferred lipophilic gelling agents, mention may be made of organopolysiloxane elastomers preferably chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), and in particular Dimethicone Crosspolymer (INCI name) and Dimethicone (and) Dimethicone Crosspolymer (INCI name).

According to a preferred mode, as preferred lipophilic gelling agents, mention may be made more particularly of gels of silicone elastomer dispersed in a silicone oil and/or powders of organopolysiloxane elastomer coated with silsesquioxane resin.

Thus, according to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt at 25° C., especially the following references:

dimethicone/vinyl dimethicone crosspolymer (and) dimethicone, such as KSG-6 and KSG-16 from the company Shin-Etsu;

dimethicone (and) dimethicone crosspolymer, such as DC9041 from the company Dow Corning; and dimethicone (and) dimethicone crosspolymer, such as Dow Corning EL-9240® Silicone Elastomer Blend from the company Dow Corning.

According to a particularly preferred embodiment, the composition according to the invention comprises as lipophilic gelling agent at least one crosslinked silicone elastomer having the INCI name "dimethicone (and) dimethicone crosspolymer", with, preferably, a dimethicone having a viscosity ranging from 1 to 100 cSt, in particular from 1 to 10 cSt at 25° C., such as the mixture of polydimethylsiloxane with hexadiene/polydimethylsiloxane (5 cSt) sold under the name DC 9041 by Dow Corning and the mixture of polydimethylsiloxane with hexadiene/polydimethylsiloxane (2 cSt) sold under the name EL-9240® Silicone Elastomer Blend by Dow Corning.

According to another particularly preferred mode, the composition according to the invention comprises at least one powder of organopolysiloxane elastomer coated with silsesquioxane resin, of INCI name: vinyl dimethicone/methicone silsesquioxane crosspolymer, such as the reference KSP-100 sold by the company Shin-Etsu.

As non-limiting illustrations of hydrophilic gelling agent/lipophilic gelling agent systems that are most particularly suitable for use in the invention, mention may be made especially of the polymer or copolymer system of 2-acrylamido-2-methylpropanesulfonic acid/organopolysiloxane elastomer.

Thus, a composition according to the invention may advantageously comprise as hydrophilic gelling agent/lipophilic gelling agent systems, a polymer system of 2-acrylamido-2-methylpropanesulfonic acid/organopolysiloxane elastomer(s) or copolymer of 2-acrylamido-2-methylpropanesulfonic acid and of hydroxyethyl acrylate/organopolysiloxane elastomer(s).

Preferably, a composition according to the invention may comprise as hydrophilic gelling agent/lipophilic gelling agent system, a copolymer system of 2-acrylamido-2-methylpropanesulfonic acid and of hydroxyethyl acrylate/organopolysiloxane elastomer powder.

Hydrophobic Film-Forming Polymers

As stated previously, the claimed compositions comprise at least one hydrophobic film-forming polymer especially as detailed below.

This type of polymer is particularly advantageous in so far as it makes it possible to significantly increase the staying power of the matt effect over time. As indicated previously, the performance of these polymers is advantageously increased by means of using them in a composition according to the invention.

For the purposes of the invention, the term "polymer" means a compound corresponding to the repetition of one or more units (these units being derived from compounds known as monomers). This or these unit(s) are repeated at least twice and preferably at least three times.

For the purposes of the present invention, the term "hydrophobic film-forming polymer" is intended to denote a film-forming polymer that has no affinity for water and, in this respect, does not lend itself to a formulation in the form of a solute in an aqueous medium. In particular, the term "hydrophobic polymer" means a polymer having a solubility in water at 25° C. of less than 1% by weight.

The term "film forming polymer" means a polymer that is capable of forming, by itself or in the presence of an auxiliary film-forming agent, a macroscopically continuous film on a support, especially on keratin materials, and preferably a cohesive film, and better still a film whose cohesion and mechanical properties are such that said film may be isolable and manipulable in isolation, for example when said film is prepared by pouring onto a non-stick surface, for instance a Teflon-coated or silicone-coated surface.

In particular, the hydrophobic film-forming polymer is a polymer chosen from the group comprising:

film-forming polymers that are soluble in an organic solvent medium, in particular liposoluble polymers; this means that the polymer is soluble or miscible in the organic medium and forms a single homogeneous phase when it is incorporated into the medium;

film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizer; these non-aqueous dispersions are often referred to as NADs;

film-forming polymers in the form of aqueous dispersions of polymer particles, which means that the polymer forms an insoluble phase in water, the polymer remaining stable and/or compatible once incorporated into the water, the polymer particles possibly being stabilized at their surface with at least one stabilizer. These polymer particles are often known as latices.

Hydrophobic film-forming polymers that may especially be mentioned include homopolymers and copolymers of a compound bearing an ethylenic unit, acrylic polymers and copolymers, polyurethanes, polyesters, polyureas, cellulose-based polymers such as nitrocellulose, silicone polymers such as silicone resins, silicone polyamides, polymers bearing a non-silicone organic backbone grafted with monomers containing a polysiloxane, polyamide polymers and copolymers, and polyisoprenes.

A composition according to the invention may comprise from 0.1% to 30% by weight, preferably from 0.2% to 20% by weight and even more preferentially from 0.5% to 15% by weight of hydrophobic film-forming polymer(s) relative to the total weight of the composition.

In particular, said hydrophobic film-forming polymer(s) are present totally or partially, and preferably solely, in the gelled oily phase.

As hydrophobic film-forming polymers that are most particularly suitable for use in the invention, mention may be made especially of block ethylenic polymers, vinyl polymers comprising at least one carbosiloxane dendrimer derivative and silicone resins (T resin, MQ resin).

I. Silicone Resins

According to one embodiment variant, a composition according to the invention may comprise, as hydrophobic film-forming polymer, at least one silicone resin.

More generally, the term "resin" means a compound whose structure is three-dimensional. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters "MDTQ" characterizing a type of unit.

The letter M represents the monofunctional unit of formula R1R2R3 SiO$_{1/2}$, the silicon atom being bonded to only one oxygen atom in the polymer comprising this unit.

The letter D means a difunctional unit R1R2SiO$_{2/2}$ in which the silicon atom is bonded to two oxygen atoms.

The letter T represents a trifunctional unit of formula R1SiO$_{3/2}$.

Such resins are described, for example, in the *Encyclopaedia of Polymer Science and Engineering*, vol. 15, John Wiley & Sons, New York, (1989), pp. 265-270, and U.S. Pat. Nos. 2,676,182, 3,627,851, 3,772,247, 5,248,739 or U.S. Pat. Nos. 5,082,706, 5,319,040, 5,302,685 and 4,935,484.

In the units M, D and T defined previously, R, namely R1 and R2, represents a hydrocarbon-based radical (especially alkyl) containing from 1 to 10 carbon atoms, a phenyl group, a phenylalkyl group or a hydroxyl group.

Finally, the letter Q means a tetrafunctional unit SiO$_{4/2}$ in which the silicon atom is bonded to four hydrogen atoms, which are themselves bonded to the rest of the polymer.

Various silicone resins with different properties may be obtained from these different units, the properties of these polymers varying as a function of the type of monomer (or unit), the nature and number of the radical R, the length of the polymer chain, the degree of branching and the size of the pendent chains.

As silicone resins that may be used in the compositions according to the invention, use may be made, for example, of silicone resins of MQ type, of T type or of MQT type.

MQ Resins

As examples of silicone resins of MQ type, mention may be made of the alkyl siloxysilicates of formula [(R1)$_3$SiO$_{1/2}$]$_x$(SiO$_{4/2}$)$_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of trimethyl siloxysilicate type, mention may be made of those sold under the reference SR1000 by the company General Electric, under the reference TMS 803 by the company Wacker, or under the name KF-7312J by the company Shin-Etsu or DC749 or DC593 by the company Dow Corning.

As silicone resins comprising MQ siloxysilicate units, mention may also be made of phenylalkyl siloxysilicate resins, such as phenylpropyldimethyl siloxysilicate (Silshine 151 sold by the company General Electric). The preparation of such resins is described especially in U.S. Pat. No. 5,817,302.

T Resins

Examples of silicone resins of T type that may be mentioned include the polysilsesquioxanes of formula (RSiO$_{3/2}$)$_x$ (units T) in which x is greater than 100 and such that the group R is an alkyl group containing from 1 to 10 carbon atoms, said polysilsesquioxanes also possibly comprising Si—OH end groups.

Polymethylsilsesquioxane resins that may preferably be used are those in which R represents a methyl group, for instance those sold:

by the company Wacker under the reference Resin MK, such as Belsil PMS MK: polymer comprising CH$_3$SiO$_{3/2}$ repeating units (units T), which may also comprise up to 1% by weight of (CH$_3$)$_2$SiO$_{2/2}$ units (units D) and having an average molecular weight of about 10 000 g/mol, or by the company Shin-Etsu under the reference KR-220L, which are composed of units T of formula CH$_3$SiO$_{3/2}$ and have Si—OH (silanol) end groups, under the reference KR-242A, which comprise 98% of units T and 2% of dimethyl units D and have Si—OH end groups, or alternatively under the reference KR-251 comprising 88% of units T and 12% of dimethyl units D and have Si—OH end groups.

MQT Resins

Resins comprising MQT units that are especially known are those mentioned in document U.S. Pat. No. 5,110,890.

A preferred form of resins of MQT type are MQT-propyl (also known as MQTpr) resins. Such resins that may be used in the compositions according to the invention are especially the resins described and prepared in patent application WO 2005/075 542.

The MQ-T-propyl resin preferably comprises the units:

(R1$_3$SiO$_{1/2}$)$_a$;

(ii) (R2$_2$SiO$_{2/2}$)$_b$;

(iii) (R3SiO$_{3/2}$)$_c$ and (iv) (SiO$_{4/2}$)$_d$.

with:

R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group, a being between 0.05 and 0.5, b being between 0 and 0.3, c being greater than zero, d being between 0.05 and 0.6, a+b+c+d=1, and a, b, c and d being mole fractions, on condition that more than 40 mol % of the groups R3 of the siloxane resin are propyl groups.

Preferably, the siloxane resin comprises the following units:

(i) (R1$_3$SiO$_{1/2}$)$_a$;

(iii) (R3SiO$_{3/2}$)$_c$ and (iv) (SiO$_{4/2}$)$_d$.

with:
R1 and R3 independently representing an alkyl group containing from 1 to 8 carbon atoms, R1 preferably being a methyl group and R3 preferably being a propyl group,
a being between 0.05 and 0.5 and preferably between 0.15 and 0.4,
c being greater than zero, preferably between 0.15 and 0.4,
d being between 0.05 and 0.6, preferably between 0.2 and 0.6 or alternatively between 0.2 and 0.55,
a+b+c+d=1, and a, b, c and d being mole fractions,
on condition that more than 40 mol % of the groups R3 of the siloxane resin are propyl groups.

The siloxane resins that may be used according to the invention may be obtained via a process comprising the reaction of:

A) an MQ resin comprising at least 80 mol % of units $(R1_3SiO_{1/2})_a$ and $(SiO_{4/2})_d$; with
R1 representing an alkyl group containing from 1 to 8 carbon atoms, an aryl group, a carbinol group or an amino group,
a and d being greater than zero,
the ratio a/d being between 0.5 and 1.5;
and:

B) a T-propyl resin comprising at least 80 mol % of units $(R3SiO_{3/2})_c$, with
R3 representing an alkyl group containing from 1 to 8 carbon atoms, an aryl group, a carbinol group or an amino group,
c being greater than zero,
on condition that at least 40 mol % of the groups R3 are propyl groups,
in which the mass ratio A/B is between 95/5 and 15/85 and preferably the mass ratio A/B is 30/70.

Advantageously, the A/B weight ratio is between 95/5 and 15/85. Preferably, the A/B ratio is less than or equal to 70/30. These preferred ratios have proven to allow comfortable deposits due to the absence of percolation of the rigid particles of MQ resin in the deposit.

Thus, preferably, the silicone resin is chosen from the group comprising:

a) a resin of MQ type, chosen especially from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, said polysilsesquioxanes also possibly comprising Si—OH end groups, and/or c) a resin of MQT type, especially of MQT-propyl type, which may comprise units (i) $(R1_3SiO_{1/2})_a$, $(R2_2SiO_{2/2})_b$, (iii) $(R3SiO_{3/2})_c$ and (iv) $(SiO_{4/2})_d$,
with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group, a being between 0.05 and 0.5,
b being between 0 and 0.3,
c being greater than zero,
d being between 0.05 and 0.6,
a+b+c+d=1, and a, b, c and d being mole fractions,
on condition that more than 40 mol % of the groups R3 of the siloxane resin are propyl groups.

Advantageously, a composition according to the invention may comprise, as hydrophobic film-forming polymer, at least one trimethyl siloxysilicate resin.

II. Lipodispersible Film-Forming Polymers in the Form of Non-Aqueous Dispersions of Polymer Particles, Also Known as NADs According to another embodiment variant, a composition according to the invention may comprise, as hydrophobic film-forming polymer, at least one polymer chosen from lipodispersible film-forming polymers in the form of non-aqueous dispersions of polymer particles, also known as NADs.

Non-aqueous dispersions of hydrophobic film-forming polymer that may be used include dispersions of particles of a grafted ethylenic polymer, preferably an acrylic polymer, in a liquid oily phase:

either in the form of ethylenic polymer particles dispersed in the absence of additional stabilizer at the surface of the particles, as described especially in document WO 04/055 081, or in the form of surface-stabilized particles dispersed in the liquid fatty phase. The dispersion of surface-stabilized polymer particles may be manufactured as described in document EP-A-749 747. The polymer particles may in particular be surface-stabilized by means of a stabilizer that may be a block polymer, a grafted polymer and/or a random polymer, alone or as a mixture. Dispersions of film-forming polymer in the liquid fatty phase, in the presence of stabilizers, are especially described in documents EP-A-748 746, EP-A-923 928 and EP-A-930 060.

Advantageously, dispersions of ethylenic polymer particles dispersed in the absence of additional stabilizer at the surface of said particles are used.

Examples of polymers of NAD type that may be mentioned more particularly include acrylic dispersions in isododecane, for instance Mexomer PAP® (acrylic copolymer as a dispersion in isododecane (25%) with pyrene/isoprene copolymer) sold by the company Chimex.

III. Block Ethylenic Copolymer

According to a first embodiment of the invention, the hydrophobic film-forming polymer is a block ethylenic copolymer, containing at least a first block with a glass transition temperature ($T_g$) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., said first block and said second block being connected together via a statistical intermediate segment comprising at least one of said first constituent monomers of the first block and at least one of said second constituent monomers of the second block, and said block copolymer having a polydispersity index I of greater than 2.

The block polymer used according to the invention thus comprises at least one first block and at least one second block.

The term "at least one block" is intended to mean one or more blocks.

The term "block" polymer means a polymer comprising at least two different blocks, preferably at least three different blocks.

The term "ethylenic polymer" is intended to mean a polymer obtained by polymerization of monomers comprising an ethylenic unsaturation.

The block ethylenic polymer used according to the invention is prepared exclusively from monofunctional monomers.

This means that the block ethylenic polymer used according to the present invention does not contain any multifunctional monomers, which make it possible to break the linearity of a polymer so as to obtain a branched or even crosslinked polymer, as a function of the content of multifunctional monomer. The polymer used according to the invention does not, either, contain any macromonomers (the term "macromonomer" means a monofunctional monomer containing pendent groups of polymeric nature, and preferably having a molecular mass of greater than 500 g/mol, or alternatively a polymer comprising on only one of its ends a polymerizable (or ethylenically unsaturated) end group), which are used in the preparation of a grafted polymer.

It is pointed out that, in the text hereinabove and hereinbelow, the terms "first" and "second" blocks do not in any way condition the order of said blocks in the structure of the polymer.

The first block and the second block of the polymer used in the invention may be advantageously mutually incompatible.

The term "mutually incompatible blocks" means that the mixture formed by a polymer corresponding to the first block and by a polymer corresponding to the second block is not miscible in the polymerization solvent, which is in major amount by weight, for the block polymer, at room temperature (25° C.) and atmospheric pressure ($10^5$ Pa), for a content of the mixture of said polymers of greater than or equal to 5% by weight relative to the total weight of the mixture of said polymers and of said polymerization solvent, it being understood that:

i) said polymers are present in the mixture in a content such that the respective weight ratio ranges from 10/90 to 90/10, and that ii) each of the polymers corresponding to the first and second blocks has an average (weight-average or number-average) molar mass equal to that of the block polymer±15%.

In the case of a mixture of polymerization solvents, and in the event that two or more solvents are present in identical mass proportions, said polymer mixture is immiscible in at least one of them.

Needless to say, in the case of a polymerization performed in a single solvent, this solvent is the solvent that is in major amount.

The block polymer according to the invention comprises at least a first block and at least a second block that are connected together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate segment is a block comprising at least one constituent monomer of the first block and at least one constituent monomer of the second block of the polymer allowing these blocks to be "compatibilized".

Advantageously, the intermediate segment comprising at least one constituent monomer of the first block and at least one constituent monomer of the second block of the polymer is a statistical polymer.

Preferably, the intermediate block is derived essentially from constituent monomers of the first block and of the second block.

The term "essentially" means at least 85%, preferably at least 90%, better still 95% and even better still 100%.

The block polymer according to the invention is advantageously a film-forming block ethylenic polymer.

The term "ethylenic polymer" is intended to mean a polymer obtained by polymerization of monomers comprising an ethylenic unsaturation.

The term "film-forming polymer" means a polymer that is capable of forming, by itself or in the presence of an auxiliary film-forming agent, a continuous deposit on a support, especially on keratin materials.

Preferentially, the polymer according to the invention does not comprise any silicon atoms in its backbone. The term "backbone" means the main chain of the polymer, as opposed to the pendent side chains.

Preferably, the polymer according to the invention is not water-soluble, i.e. the polymer is not soluble in water or in a mixture of water and linear or branched lower monoalcohols containing from 2 to 5 carbon atoms, for instance ethanol, isopropanol or n-propanol, without modifying the pH, at a solids content of at least 1% by weight, at room temperature (25° C.).

Preferably, the polymer according to the invention is not an elastomer.

The term "non-elastomeric polymer" means a polymer which, when it is subjected to a constraint intended to pull it (for example by 30% relative to its initial length), does not return to a length substantially identical to its initial length when the constraint ceases.

More specifically, the term "non-elastomeric polymer" denotes a polymer with an instantaneous recovery $R_i<50\%$ and a delayed recovery $R_{2h}<70\%$ after having been subjected to a 30% elongation. Preferably, $R_i$ is $<30\%$ and $R_{2h}<50\%$.

More specifically, the non-elastomeric nature of the polymer is determined according to the following protocol:

A polymer film is prepared by pouring a solution of the polymer in a Teflon-coated mould, followed by drying for 7 days in an environment conditioned at 23±5° C. and 50±10% relative humidity.

A film about 100 µm thick is thus obtained, from which are cut rectangular test specimens (for example using a punch) 15 mm wide and 80 mm long.

This sample is subjected to a tensile stress using a machine sold under the reference Zwick, under the same temperature and humidity conditions as for the drying.

The test specimens are pulled at a speed of 50 mm/min and the distance between the jaws is 50 mm, which corresponds to the initial length ($I_0$) of the test specimen.

The instantaneous recovery Ri is determined in the following manner:

the test specimen is pulled by 30% ($\varepsilon_{max}$), i.e. about 0.3 times its initial length ($I_0$), the stress is removed by imposing a return speed equal to the tensile speed, i.e. 50 mm/minute, and the residual elongation of the specimen is measured as a percentage, after returning to zero stress load ($\varepsilon_i$).

The percentage instantaneous recovery ($R_1$) is given by the following formula:

$$R_1 = ((\varepsilon_{max} - \varepsilon_i)/\varepsilon_{max}) \times 100$$

To determine the delayed recovery, the percentage residual elongation of the test specimen ($\varepsilon_{2h}$) is measured after 2 hours, 2 hours after returning to zero stress load.

The percentage delayed recovery ($R_{2h}$) is given by the following formula:

$$R_{2h} = (\varepsilon_{max} - \varepsilon_{2h})/\varepsilon_{max}) \times 100$$

Purely as a guide, a polymer according to one embodiment of the invention preferably has an instantaneous recovery $R_i$ of 10% and a delayed recovery $R_{2h}$ of 30%.

The polydispersity index of the polymer of the invention is greater than 2.

Advantageously, the block polymer used in the compositions according to the invention has a polydispersity index I of greater than 2, for example ranging from 2 to 9, preferably greater than or equal to 2.5, for example ranging from 2.5 to 8 and better still greater than or equal to 2.8, and in particular ranging from 2.8 to 6.

The polydispersity index I of the polymer is equal to the ratio of the weight-average mass Mw to the number-average mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer according to the invention is preferably less than or equal to 300 000; it ranges, for example, from 35 000 to 200 000 and better still from 45 000 to 150 000 g/mol.

The number-average mass (Mn) of the polymer according to the invention is preferably less than or equal to 70 000; it ranges, for example, from 10 000 to 60 000 and better still from 12 000 to 50 000 g/mol.

Preferably, the polydispersity index of the polymer according to the invention is greater than 2, for example ranging from 2 to 9, preferably greater than or equal to 2.5, for example ranging from 2.5 to 8, and better still greater than or equal to 2.8, and in particular ranging from 2.8 to 6.

First Block with a $T_g$ of Greater than or Equal to 40° C.

The block with a $T_g$ of greater than or equal to 40° C. has, for example, a Tg ranging from 40 to 150° C., preferably greater than or equal to 50° C., for example ranging from 50° C. to 120° C. and better still greater than or equal to 60° C., for example ranging from 60° C. to 120° C.

The glass transition temperatures indicated for the first and second blocks may be theoretical $T_g$ values determined from the theoretical $T_g$ values of the constituent monomers of each of the blocks, which may be found in a reference manual such as the Polymer Handbook, 3rd Edition, 1989, John Wiley, according to the following relationship, known as Fox's law:

$$1/T_g = \Sigma(\overline{\omega}_i/T_{g_i}), i$$

$\overline{\omega}_i$ being the mass fraction of the monomer i in the block under consideration and $T_{g_i}$ being the glass transition temperature of the homopolymer of the monomer i.

Unless otherwise indicated, the $T_g$ values indicated for the first and second blocks in the present patent application are theoretical $T_g$ values.

The difference between the glass transition temperatures of the first and second blocks is generally greater than 10° C., preferably greater than 20° C. and better still greater than 30° C.

In the present invention, the expression: "between . . . and . . . " is intended to denote a range of values for which the limits mentioned are excluded, and "from . . . to . . . " and "ranging from . . . to . . . " are intended to denote a range of values for which the limits are included.

The block with a $T_g$ of greater than or equal to 40° C. may be a homopolymer or a copolymer.

The block with a $T_g$ of greater than or equal to 40° C. may be derived totally or partially from one or more monomers which are such that the homopolymer prepared from these monomers has a glass transition temperature of greater than or equal to 40° C. This block may also be referred to as a "rigid block".

In the case where this block is a homopolymer, it is derived from monomers which are such that the homopolymers prepared from these monomers have glass transition temperatures of greater than or equal to 40° C. This first block may be a homopolymer consisting of only one type of monomer (for which the $T_g$ of the corresponding homopolymer is greater than or equal to 40° C.).

In the case where the first block is a copolymer, it may be totally or partially derived from one or more monomers, the nature and concentration of which are chosen such that the $T_g$ of the resulting copolymer is greater than or equal to 40° C.

The copolymer may comprise, for example:
monomers which are such that the homopolymers prepared from these monomers have $T_g$ values of greater than or equal to 40° C., for example a $T_g$ ranging from 40° C. to 150° C., preferably greater than or equal to 50° C., for example ranging from 50° C. to 120° C. and better still greater than or equal to 60° C., for example ranging from 60° C. to 120° C., and monomers which are such that the homopolymers prepared from these monomers have $T_g$ values of less than 40° C., chosen from monomers with a $T_g$ of between 20° C. and 40° C. and/or monomers with a $T_g$ of less than or equal to 20° C., for example a $T_g$ ranging from −100° C. to 20° C., preferably less than 15° C., in particular ranging from −80° C. to 15° C. and better still less than 10° C., for example ranging from −50° C. to 0° C., as described later.

The first monomers of which the homopolymers have a glass transition temperature of greater than or equal to 40° C. are chosen, preferably, from the following monomers, also known as the main monomers:

the methacrylates of formula $CH_2=C(CH_3)-COOR_1$, in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group, preferably a $C_8$ to $C_{12}$ cycloalkyl, such as isobornyl methacrylate, the acrylates of formula $CH_2=CH-COOR_2$, in which $R_2$ represents a $C_4$ to $C_{12}$ cycloalkyl group such as an isobornyl group or a tert-butyl group, the (meth)acrylamides of formula:

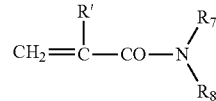

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1, 1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

The first block is advantageously obtained from at least one acrylate monomer of formula $CH_2\!\!=\!\!CH\!\!-\!\!COOR_2$ and from at least one methacrylate monomer of formula $CH_2\!\!=\!\!C(CH_3)\!\!-\!\!COOR_2$ in which $R_2$ represents a $C_4$ to $C_{12}$ cycloalkyl group, preferably a $C_8$ to $C_{12}$ cycloalkyl, such as isobornyl. The monomers and the proportions thereof are preferably chosen such that the glass transition temperature of the first block is greater than or equal to 40° C.

According to one embodiment, the first block is obtained from:
i) at least one acrylate monomer of formula $CH_2\!\!=\!\!CH\!\!-\!\!COOR_2$ in which $R_2$ represents a $C_4$ to $C_{12}$ cycloalkyl group, preferably a $C_8$ to $C_{12}$ cycloalkyl group, such as isobornyl,
ii) and at least one methacrylate monomer of formula $CH_2\!\!=\!\!C(CH_3)\!\!-\!\!COOR'_2$ in which $R'_2$ represents a $C_4$ to $C_{12}$ cycloalkyl group, preferably a $C_8$ to $C_{12}$ cycloalkyl group, such as isobornyl.

According to one embodiment, the first block is obtained from at least one acrylate monomer of formula $CH_2\!\!=\!\!CH\!\!-\!\!COOR_2$ in which $R_2$ represents a $C_8$ to $C_{12}$ cycloalkyl group, such as isobornyl, and from at least one methacrylate monomer of formula $CH_2\!\!=\!\!C(CH_3)\!\!-\!\!COOR'_2$ in which $R'_2$ represents a $C_8$ to $C_{12}$ cycloalkyl group, such as isobornyl.

Preferably, $R_2$ and $R'_2$ represent, independently or simultaneously, an isobornyl group.

Preferably, the block copolymer comprises from 50% to 80% by weight of isobornyl methacrylate/acrylate, from 10% to 30% by weight of isobutyl acrylate and from 2% to 10% by weight of acrylic acid.

The first block may be obtained exclusively from said acrylate monomer and from said methacrylate monomer.

The acrylate monomer and the methacrylate monomer are preferably in mass proportions of between 30/70 and 70/30, preferably between 40/60 and 60/40 and especially of the order of 50/50.

The proportion of the first block advantageously ranges from 20% to 90% by weight of the polymer, better still from 30% to 80% and even better still from 60% to 80%.

According to one embodiment, the first block is obtained by polymerization of isobornyl methacrylate and isobornyl acrylate.

Second Block with a Glass Transition Temperature of Less than 20° C.

The second block advantageously has a glass transition temperature $T_g$ of less than or equal to 20° C., for example, a $T_g$ ranging from −100° C. to 20° C., preferably less than or equal to 15° C., especially ranging from −80° C. to 15° C. and better still less than or equal to 10° C., for example ranging from −100° C. to 10° C., especially ranging from −30° C. to 10° C.

The second block is totally or partially derived from one or more second monomers, which are such that the homopolymer prepared from these monomers has a glass transition temperature of less than or equal to 20° C.

This block may also be referred to as a "flexible block".

The monomer with a Tg of less than or equal to 20° C. (known as the second monomer) is preferably chosen from the following monomers:

the acrylates of formula $CH_2\!\!=\!\!CHCOOR_3$, $R_3$ representing a linear or branched $C_1$ to $C_{12}$ unsubstituted alkyl group, with the exception of the tert-butyl group, in which one or more heteroatoms chosen from O, N and S are optionally intercalated, the methacrylates of formula $CH_2\!\!=\!\!C(CH_3)\!\!-\!\!COOR_4$, $R_4$ representing a linear or branched $C_6$ to $C_{12}$ unsubstituted alkyl group, in which one or more heteroatoms chosen from O, N and S are optionally intercalated, the vinyl esters of formula $R_5\!\!-\!\!CO\!\!-\!\!CH\!\!=\!\!CH_2$ in which $R_5$ represents a linear or branched $C_4$ to $C_{12}$ alkyl group, ethers of vinyl alcohol and of a $C_4$ to $C_{12}$ alcohol, N—($C_4$ to $C_{12}$)alkyl acrylamides, such as N-octylacrylamide, and mixtures thereof.

The preferred monomers with a $T_g$ of less than or equal to 20° C. are isobutyl acrylate, 2-ethylhexyl acrylate or mixtures thereof in all proportions.

Each of the first and second blocks may contain in small proportion at least one constituent monomer of the other block.

Thus, the first block may contain at least one constituent monomer of the second block, and vice versa.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from:

ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof, the methacrylates of formula $CH_2\!\!=\!\!C(CH_3)\!\!-\!\!COOR_6$, in which $R_6$ represents a linear or branched alkyl group containing from 1 to 4 carbon atoms, such as a methyl, ethyl, propyl or isobutyl group, said alkyl group being substituted with one or more substituents chosen from hydroxyl groups (for instance 2-hydroxypropyl methacrylate and 2-hydroxyethyl methacrylate) and halogen atoms (Cl, Br, I or F), such as trifluoroethyl methacrylate, the methacrylates of formula $CH_2\!\!=\!\!C(CH_3)\!\!-\!\!COOR_9$, $R_9$ representing a linear or branched $C_6$ to $C_{12}$ alkyl group in which one or more heteroatoms chosen from O, N and S are optionally intercalated, said alkyl group being substituted with one or more substituents chosen from hydroxyl groups and halogen atoms (Cl, Br, I and F), the acrylates of formula $CH_2\!\!=\!\!CHCOOR_{10}$, $R_{10}$ representing a linear or branched $C_1$ to $C_{12}$ alkyl group substituted with one or more substituents chosen from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit 5 to 10 times, for example methoxy-POE, or $R_{10}$ represents a polyoxyethylenated group comprising from 5 to 10 ethylene oxide units.

In particular, the first block may comprise as additional monomer:
(meth)acrylic acid, preferably acrylic acid,
tert-butyl acrylate,
the methacrylates of formula $CH_2=C(CH_3)-COOR_1$, in which $R_1$ represents a linear or branched unsubstituted alkyl group containing from 1 to 4 carbon atoms, such as a methyl, ethyl, propyl or isobutyl group,
the (meth)acrylamides of formula:

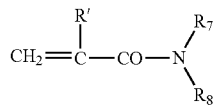

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group,
and R' denotes H or methyl. Examples of monomers that may be mentioned include N-butylacrylamide, N-tert-butylacrylamide, N-isopropylacrylamide, N,N-dimethylacrylamide and N,N-dibutylacrylamide,
and mixtures thereof.

The additional monomer may represent 0.5% to 30% by weight relative to the weight of the polymer. According to one embodiment, the polymer of the invention does not contain any additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block.

Preferably, the polymer comprises at least isobornyl acrylate and isobornyl methacrylate monomers in equivalent weight proportion in the first block, and isobutyl acrylate and acrylic acid monomers in the second block, the first block representing 70% by weight of the polymer.

Preferably, the polymer comprises at least isobornyl acrylate and isobornyl methacrylate monomers in equivalent weight proportion in the first block and isobutyl acrylate and acrylic acid monomers in the second block. Preferably, the block with a $T_g$ of greater than 40° C. represents 70% by weight of the polymer, and acrylic acid represents 5% by weight of the polymer.

According to one embodiment, the first block does not comprise any additional monomer.

According to one preferred embodiment, the second block comprises acrylic acid as additional monomer. In particular, the second block is advantageously obtained from an acrylic acid monomer and from at least one other monomer with a $T_g$ of less than or equal to 20° C.

The block copolymer may advantageously comprise more than 2% by weight of acrylic acid monomers, and in particular from 2% to 15% by weight, for example from 3% to 15% by weight, in particular from 4% to 15% by weight or even from 4% to 10% by weight of acrylic acid monomers, relative to the total weight of said copolymer.

The constituent monomers of the second block and the proportions thereof are chosen such that the glass transition temperature of the second block is less than or equal to 20° C.

Intermediate Segment

The intermediate segment (also known as the intermediate block) connects the first block and the second block of the polymer used according to the present invention. The intermediate segment results from the polymerization:

i) of the first monomer(s), and optionally of the additional monomer(s), which remain available after their polymerization to a maximum degree of conversion of 90% to form the first block, ii) and of the second monomer(s), and optionally of the additional monomer(s), added to the reaction mixture.

The formation of the second block is initiated when the first monomers no longer react or are no longer incorporated into the polymer chain either because they are all consumed or because their reactivity no longer allows them to be.

Thus, the intermediate segment comprises the first available monomers, resulting from a degree of conversion of these first monomers of less than or equal to 90%, during the introduction of the second monomer(s) during the synthesis of the polymer.

The intermediate segment of the block polymer is a statistical polymer (which may also be referred to as a statistical block). This means that it comprises a random distribution of the first monomer(s) and of the second monomer(s) and also of the additional monomer(s) optionally present.

Thus, the intermediate segment is a statistical block, as are the first block and the second block if they are not homopolymers (i.e. if they are both formed from at least two different monomers).

Process for Preparing the Copolymer

The block ethylenic copolymer according to the invention is prepared by free radical polymerization, according to the techniques that are well known for this type of polymerization.

The free radical polymerization is performed in the presence of an initiator, the nature of which is adapted, in a known manner, as a function of the desired polymerization temperature and of the polymerization solvent. In particular, the initiator may be chosen from initiators bearing a peroxide function, redox couples or other free radical polymerization initiators known to those skilled in the art.

In particular, examples of initiators bearing a peroxide function that may be mentioned include:

a. peroxyesters such as tert-butyl peroxyacetate, tert-butyl perbenzoate, tert-butyl peroxy-2-ethylhexanoate (Trigonox 21S from Akzo Nobel) or 2,5-bis(2-ethylhexanoylperoxy)-2,5-dimethylhexane (Trigonox 141 from Akzo Nobel);

b. peroxydicarbonates such as diisopropyl peroxydicarbonate;

c. peroxy ketones such as methyl ethyl ketone peroxide;

d. hydroperoxides such as aqueous hydrogen peroxide solution ($H_2O_2$) or tert-butyl hydroperoxide;

e. diacyl peroxides such as acetyl peroxide or benzoyl peroxide;

f dialkyl peroxides such as di-tert-butyl peroxide;

g. mineral peroxides such as potassium peroxodisulfate ($K_2S_2O_8$).

As initiator in the form of a redox couple, mention may be made of the potassium thiosulfate+potassium peroxodisulfate couple, for example.

According to a preferred embodiment, the initiator is chosen from organic peroxides comprising from 8 to 30 carbon atoms. Preferably, the initiator used is 2,5-bis(2-ethylhexanoylperoxy)-2,5-dimethylhexane sold under the reference Trigonox® 141 by the company Akzo Nobel.

The block copolymer used according to the invention is prepared by free radical polymerization and not by controlled or living polymerization. In particular, the polymerization of the block ethylenic copolymer is performed in the absence of control agents, and in particular in the absence of control agents conventionally used in living or controlled polymerization processes, such as nitroxides, alkoxyamines, dithioesters, dithiocarbamates, dithiocarbonates or xanthates, trithiocarbonates or copper-based catalysts, for example.

As mentioned previously, the intermediate segment is a random block, as are the first block and the second block if they are not homopolymers (i.e. if they are both formed from at least two different monomers).

The block copolymer may be prepared by free radical polymerization, and in particular by a process that consists in mixing, in the same reactor, a polymerization solvent, an initiator, at least one monomer with a glass transition temperature of greater than or equal to 40° C., and at least one monomer with a glass transition temperature of less than or equal to 20° C., according to the following sequence:
   some of the polymerization solvent and optionally some of the initiator and of the monomers for the first addition are poured into the reactor, and the mixture is heated to a reaction temperature of between 60° C. and 120° C.,
   said at least one first monomer with a $T_g$ of greater than or equal to 40° C. and optionally some of the initiator are then poured in, in a first addition, and the mixture is left to react for a time T corresponding to a maximum degree of conversion of said monomers of 90%,
   further polymerization initiator and said at least one second monomer with a glass transition temperature of less than or equal to 20° C. are then poured into the reactor, in a second addition, and the mixture is left to react for a time T' after which the degree of conversion of said monomers reaches a plateau,
   the reaction mixture is cooled to room temperature.

Preferably, the copolymer may be prepared by free radical polymerization, in particular by a process that consists in mixing, in the same reactor, a polymerization solvent, an initiator, an acrylic acid monomer, at least one monomer with a glass transition temperature of less than or equal to 20° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of steps:
   some of the polymerization solvent and optionally some of the initiator and of the monomers for the first addition are poured into the reactor, and the mixture is heated to a reaction temperature of between 60° C. and 120° C.,
   said at least one acrylate monomer of formula $CH_2=CH-COOR_2$ and said at least one methacrylate monomer of formula $CH_2=C(CH_3)-COOR'_2$, as monomers with a $T_g$ of greater than or equal to 40° C., and optionally some of the initiator, are then poured in, in a first addition, and the mixture is left to react for a time T corresponding to a maximum degree of conversion of said monomers of 90%,
   further polymerization initiator, the acrylic acid monomer and said at least one monomer with a glass transition temperature of less than or equal to 20° C. are then poured into the reactor, in a second addition, and the mixture is left to react for a time T' after which the degree of conversion of said monomers reaches a plateau,
   the reaction mixture is cooled to room temperature.

The term "polymerization solvent" is intended to mean a solvent or a mixture of solvents. In particular, as polymerization solvents that may be used, mention may be made of:
   ketones that are liquid at room temperature, such as methyl ethyl ketone, methyl isobutyl ketone, diisobutyl ketone, isophorone, cyclohexanone or acetone;
   propylene glycol ethers that are liquid at room temperature, such as propylene glycol monomethyl ether, propylene glycol monomethyl ether acetate or dipropylene glycol mono n-butyl ether;
   short-chain esters, containing from 3 to 8 carbon atoms in total, such as ethyl acetate, methyl acetate, propyl acetate, n-butyl acetate or isopentyl acetate;
   ethers that are liquid at room temperature, such as diethyl ether, dimethyl ether or dichlorodiethyl ether;
   alkanes that are liquid at room temperature, such as decane, heptane, dodecane isododecane, cyclohexane and isohexadecane;
   aromatic cyclic compounds that are liquid at room temperature, such as toluene and xylene; aldehydes that are liquid at room temperature, such as benzaldehyde and acetaldehyde, and mixtures thereof.

Conventionally, the polymerization solvent is a volatile oil with a flash point of less than 80° C. The flash point is measured in particular according to standard ISO 3679.

The polymerization solvent may be chosen in particular from ethyl acetate, butyl acetate, alcohols such as isopropanol or ethanol, and aliphatic alkanes such as isododecane, and mixtures thereof. Preferably, the polymerization solvent is a mixture of butyl acetate and isopropanol or isododecane.

According to another embodiment, the copolymer may be prepared by free radical polymerization according to a preparation process that consists in mixing, in the same reactor, a polymerization solvent, an initiator, at least one monomer with a glass transition temperature of less than or equal to 20° C. and at least one monomer with a $T_g$ of greater than or equal to 40° C., according to the following sequence of steps:
   some of the polymerization solvent and optionally some of the initiator and of the monomers for the first addition are poured into the reactor, and the mixture is heated to a reaction temperature of between 60° C. and 120° C.,
   said at least one monomer with a glass transition temperature of less than or equal to 20° C. and optionally some of the initiator are then poured in, in a first addition, and the mixture is left to react for a time T corresponding to a maximum degree of conversion of said monomers of 90%,
   further polymerization initiator and said at least one monomer with a Tg of greater than or equal to 40° C. are then poured into the reactor, in a second addition, and are left to react for a time T' after which the degree of conversion of said monomers reaches a plateau,
   the reaction mixture is cooled to room temperature.

According to a preferred embodiment, the copolymer may be prepared by free radical polymerization according to a preparation process that consists in mixing, in the same reactor, a polymerization solvent, an initiator, an acrylic acid monomer, at least one monomer with a glass transition temperature of less than or equal to 20° C., at least one monomer with a $T_g$ of greater than or equal to 40° C., and in particular, as monomers with a $T_g$ of greater than or equal to 40° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of steps:

some of the polymerization solvent and optionally some of the initiator and of the monomers for the first addition are poured into the reactor, and the mixture is heated to a reaction temperature of between 60° C. and 120° C., the acrylic acid monomer and said at least one monomer with a glass transition temperature of less than or equal to 20° C. and optionally some of the initiator are then poured in, in a first addition, and the mixture is left to react for a time T corresponding to a maximum degree of conversion of said monomers of 90%, further polymerization initiator, said at least one acrylate monomer of formula $CH_2=CH-COOR_2$ and said at least one methacrylate monomer of formula $CH_2=C(CH_3)-COOR'_2$, as monomer with a $T_g$ of greater than or equal to 40° C., are then poured into the reactor, in a second addition, and the mixture is left to react for a time T' after which the degree of conversion of said monomers reaches a plateau, the reaction mixture is cooled to room temperature.

The polymerization temperature is preferably about 90° C.

The reaction time after the second addition is preferably between 3 and 6 hours.

Preferably, the block ethylenic copolymer is present in the composition in a solids content ranging from 0.1% to 60%, better still from 0.5% to 50%, better still from 1% to 30% and even better still from 1% to 40% by weight relative to the total weight of the composition.

Distillation of the Synthesis Solvent

It is possible to perform a step of total or partial removal of said volatile oil or solvent (conventionally isododecane). This is then performed in particular by distillation, optionally under vacuum, and optional addition of non-volatile hydrocarbon-based ester oil comprising at least 16 carbon atoms and having a molar mass of less than 650 g/mol, such as octyldodecyl neopentanoate (especially 2-octyldodecyl neopentanoate).

This step is performed at elevated temperature and optionally under vacuum to distil off a maximum amount of volatile synthesis solvent, and is known to those skilled in the art.

Polyamide Silicone Block Polymer

According to another embodiment variant, a composition according to the invention comprises, as hydrophobic film-forming polymer, at least one polyamide silicone block polymer, also known as a silicone polyamide.

The silicone polyamides are preferably solid at room temperature (25° C.) and atmospheric pressure (760 mmHg).

For the purposes of the invention, the term "polymer" means a compound containing at least two repeating units, preferably at least three repeating units and better still ten repeating units.

The silicone polyamides of the composition of the invention may be polymers of the polyorganosiloxane type, for instance those described in documents U.S. Pat. Nos. 5,874,069, 5,919,441, 6,051,216 and 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

According to a first variant, the silicone polymers are polyorganosiloxanes as defined above in which the units capable of establishing hydrogen interactions are located in the polymer chain.

The silicone polymers may be more particularly polymers comprising at least one unit corresponding to the general formula I:

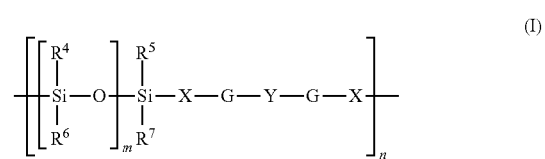

in which

R4, R5, R6 and R7, which may be identical or different, represent a group chosen from:

saturated or unsaturated, linear, branched or cyclic $C_1$ to $C_{40}$ hydrocarbon-based groups, which may contain in their chain one or more oxygen, sulfur and/or nitrogen atoms, and which may be partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulfur and/or nitrogen atoms, the groups X, which may be identical or different, represent a linear or branched $C_1$ to $C_{30}$ alkylenediyl group, possibly containing in its chain one or more oxygen and/or nitrogen atoms, Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ aminoalkyl groups, or Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and R8 represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;

the groups G, which may be identical or different, represent divalent groups chosen from:

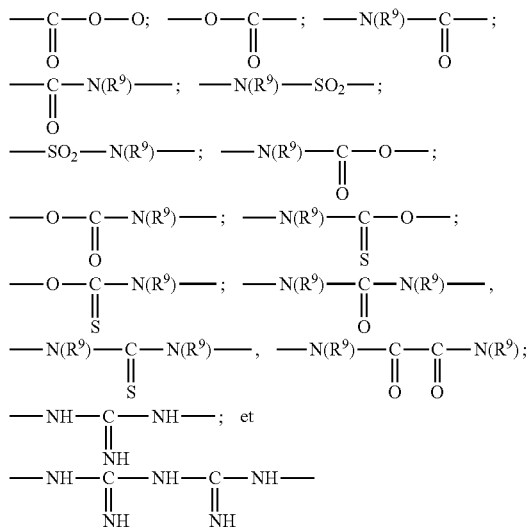

in which R9 represents a hydrogen atom or a linear or branched $C_1$ to $C_{20}$ alkyl group, on condition that at least 50% of the groups R9 of the polymer represent a hydrogen atom and that at least two of the groups G of the polymer are a group other than:

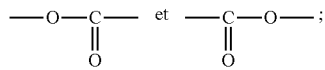

n is an integer ranging from 2 to 500 and preferably from 2 to 200, and m is an integer ranging from 1 to 1000, preferably from 1 to 700 and better still from 6 to 200.

According to the invention, 80% of the groups R4, R5, R6 and R7 of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:
  linear $C_1$ to $C_{20}$ and preferably $C_1$ to $C_{10}$ alkylene groups,
  $C_{30}$ to $C_{56}$ branched alkylene groups possibly comprising rings and unconjugated unsaturations,
  $C_5$-$C_6$ cycloalkylene groups,
  phenylene groups optionally substituted with one or more $C_1$ to $C_{40}$ alkyl groups,
  $C_1$ to $C_{20}$ alkylene groups comprising from 1 to 5 amide groups,
  $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups,
  polyorganosiloxane chains of formula:

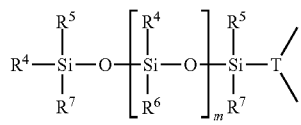

in which R4, R5, R6, R7, T and m are as defined above, and
polyorganosiloxane chains of formula:

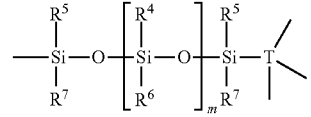

According to the second variant, the polyorganosiloxanes may be polymers comprising at least one unit corresponding to formula (II):

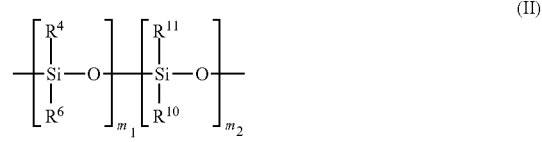

in which
R4 and R6, which may be identical or different, are as defined above for formula (I),
R10 represents a group as defined above for R4 and R6, or represents the group of formula —X-G-R12 in which X and G are as defined above for formula (I) and R12 represents a hydrogen atom or a linear, branched or cyclic, saturated or unsaturated $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups,
R11 represents a group of formula —X-G-R12 in which X, G and R12 are as defined above,
m1 is an integer ranging from 1 to 998, and
m2 is an integer ranging from 2 to 500.

According to the invention, the silicone polymer used as structuring agent may be a homopolymer, that is to say a polymer comprising several identical units, in particular units of formula (I) or of formula (II).

According to the invention, it is also possible to use a silicone polymer formed from a copolymer comprising several different units of formula (I), that is to say a polymer in which at least one of the groups R4, R5, R6, R7, X, G, Y, m and n is different in one of the units. The copolymer may also be formed from several units of formula (II), in which at least one of the groups R4, R6, R10, R11, m1 and m2 is different in at least one of the units.

It is also possible to use a polymer comprising at least one unit of formula (I) and at least one unit of formula (II), the units of formula (I) and the units of formula (II) possibly being identical to or different than each other.

According to one variant of the invention, it is also possible to use a polymer furthermore comprising at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups, and combinations thereof.

These copolymers may be block polymers or grafted polymers.

According to an advantageous embodiment of the invention, the groups capable of establishing hydrogen interactions are amide groups of formulae —C(O)NH— and —HN—C(O)—. In this case, the structuring agent may be a polymer comprising at least one unit of formula (III) or (IV):

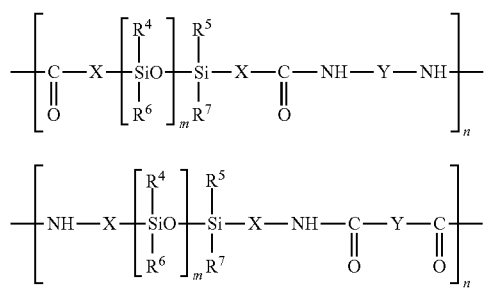

(III)

or (IV)

in which R4, R5, R6, R7, X, Y, m and n are as defined above.

Such a unit may be obtained:

either by a condensation reaction between a silicone containing α,ω-carboxylic acid ends and one or more diamines, according to the following reaction scheme:

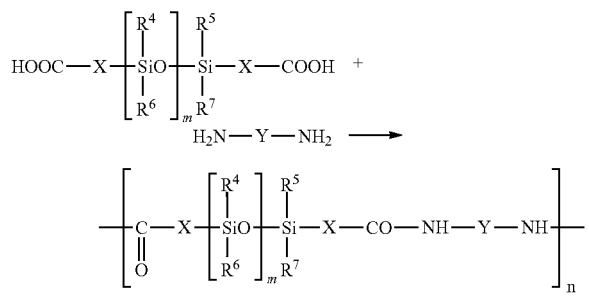

or by reaction of two molecules of α-unsaturated carboxylic acid with a diamine according to the following reaction scheme:

$$CH_2=CH-X^1-COOH+H_2N-Y-NH_2$$
$$\longrightarrow CH_2=CH-X^1-CO-NH-Y-NH-$$
$$CO-X^1-CH=CH_2$$

followed by the addition of a siloxane to the ethylenic unsaturations, according to the following scheme:

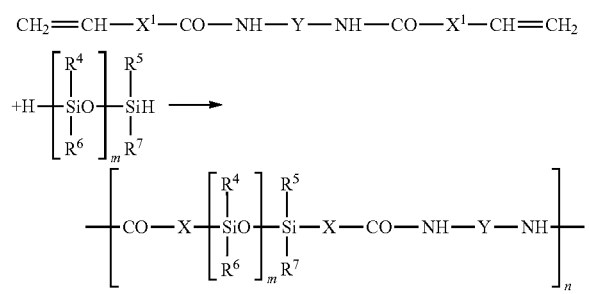

in which X1-(CH$_2$)$_2$— corresponds to X defined above and Y, R4, R5, R6, R7 and m are as defined above, or by reaction of a silicone containing α,ω-NH2 ends and a diacid of formula HOOC—Y—COOH according to the following reaction scheme:

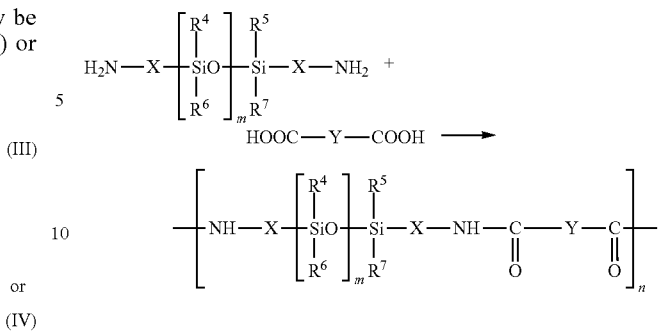

In these polyamides of formula (III) or (IV), m ranges from 1 to 700, in particular from 15 to 500 and especially from 50 to 200, and n ranges in particular from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched, or which may comprise rings and/or unsaturations, containing from 1 to 40 carbon atoms, in particular 1 to 20 carbon atoms and better still from 2 to 6 carbon atoms, in particular 6 carbon atoms.

In formulae (III) and (IV), the alkylene group representing X or Y may optionally contain in its alkylene part at least one of the following components:
one to five amide, urea, urethane or carbamate groups,
a $C_5$ or $C_6$ cycloalkyl group, and
a phenylene group optionally substituted with 1 to 3 identical or different $C_1$ to $C_3$ alkyl groups.

In formulae (III) and (IV), the alkylene groups may also be substituted with at least one component chosen from the group consisting of:
a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which R8 represents a polyorganosiloxane chain and T represents a group of formula:

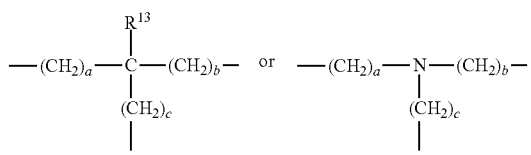

in which a, b and c are, independently, integers ranging from 1 to 10, and R13 is a hydrogen atom or a group such as those defined for R4, R5, R6 and R7.

In formulae (III) and (IV), R4, R5, R6 and R7 preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

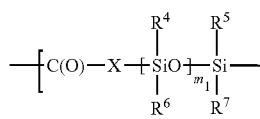 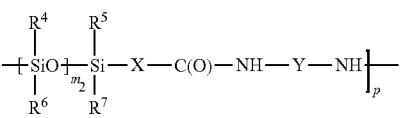

(V)

in which X, Y, n and R4 to R7 have the meanings given above, m1 and m2, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

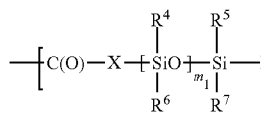 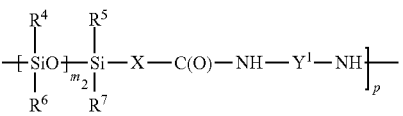

(VI)

in which R4 to R7, X, Y, m1, m2, n and p have the meanings given above and Y1 is different than Y but chosen from the groups defined for Y. As previously, the various units may be structured to form either a block copolymer, or a random copolymer or an alternating copolymer.

In this first embodiment of the invention, the structuring agent may also consist of a grafted copolymer. Thus, the polyamide containing silicone units may be grafted and optionally crosslinked with silicone chains containing amide groups. Such polymers may be synthesized with trifunctional amines.

In this case, the polymer may comprise at least one unit of formula (VII):

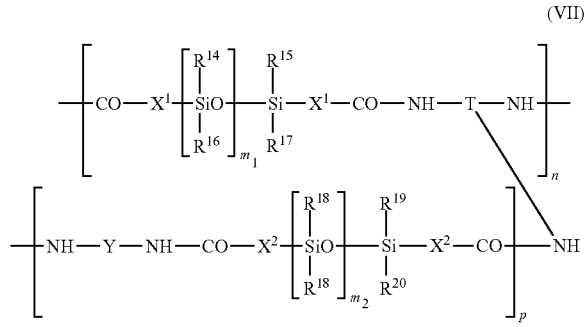

(VII)

in which X1 and X2, which are identical or different, have the meaning given for X in formula (I), n is as defined in formula (I), Y and T are as defined in formula (I), R14 to R21 are groups chosen from the same group as R4 to R7, m1 and m2 are numbers in the range from 1 to 1000, and p is an integer ranging from 2 to 500.

In formula (VII), it is preferred that:
p is in the range from 1 to 25 and better still from 1 to 7,
R14 to R21 are methyl groups, T corresponds to one of the following formulae:

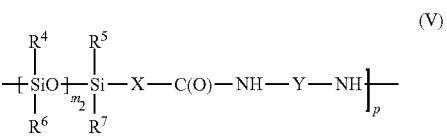

-continued

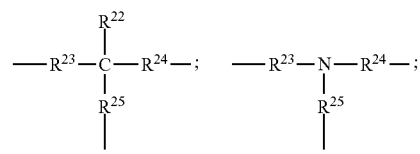

in which R22 is a hydrogen atom or a group chosen from the groups defined for R4 to R7, and R23, R24 and R25 are, independently, linear or branched alkylene groups, and more preferably correspond to the formula:

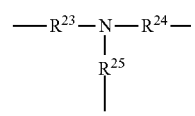

in particular with R23, R24 and R25 representing —$CH_2$—$CH_2$—, m1 and m2 are from 15 to 500 and better still from 15 to 45, X1 and X2 represent —$(CH_2)_{10}$—, and Y represents —$CH_2$—.

These polyamides containing a grafted silicone unit of formula (VII) may be copolymerized with polyamide-silicones of formula (II) to form block copolymers, alternating copolymers or random copolymers. The weight percentage of grafted silicone units (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (III) or (IV) and hydrocarbon-based polyamide units, may be used. In this case, the polyamide-silicone units may be located at the ends of the hydrocarbon-based polyamide.

According to one preferred embodiment, the silicone polyamide comprises units of formula III, preferably in which the groups R4, R5, R6 and R7 represent methyl groups, one from among X and Y represents an alkylene group of 6 carbon atoms and the other represents an alkylene group of 11 carbon atoms, n representing the degree of polymerization, DP, of the polymer. By way of example of such silicone polyamides, mention may be made of the compounds sold by the company Dow Corning under the names DC 2-8179 (DP 100) and DC 2-8178 (DP 15), the INCI name of which is Nylon-611/dimethicone copolymers.

Advantageously, the composition according to the invention comprises at least one polydimethylsiloxane block polymer of general formula (I) with an index m value of about 15.

More preferably, the composition according to the invention comprises at least one polymer comprising at least one unit of formula (III) in which m ranges from 5 to 100, in particular from 10 to 75 and even more particularly is about 15; even more preferably, R4, R5, R6 and R7 independently represent a linear or branched $C_1$ to $C_{40}$ alkyl group, preferably a group $CH_3$, $C_2H_5$, $nC_3H_7$ or isopropyl in formula (III).

According to a preferred mode, use is made of the polyamide silicone polymer sold by the company Dow Corning under the name DC 2-8179 (DP 100).

As an example of silicone polymers that may be used, mention may be made of one of the silicone polyamides obtained in accordance with Examples 1 to 3 of document U.S. Pat. No. 5,981,680.

IV. Vinyl Polymer Comprising at Least One Carbosiloxane Dendrimer-Based Unit

According to one particular embodiment, a composition used according to the invention may comprise, as hydrophobic film-forming polymer, at least one vinyl polymer comprising at least one carbosiloxane dendrimer-based unit.

The vinyl polymer used according to the invention especially has a backbone and at least one side chain, which comprises a carbosiloxane dendrimer-based unit having a carbosiloxane dendrimer structure.

Vinyl polymers comprising at least one carbosiloxane dendrimer unit as described in applications WO 03/045 337 and EP 963 751 by the company Dow Corning may be used in particular.

The term "carbosiloxane dendrimer structure" in the context of the present invention represents a molecular structure with branched groups of high molecular masses, said structure having high regularity in the radial direction starting from the bond to the backbone. Such carbosiloxane dendrimer structures are described in the form of a highly branched siloxane-silylalkylene copolymer in the laid-open Japanese patent application Kokai 9-171 154.

A vinyl polymer according to the invention may contain carbosiloxane dendrimer-based units that may be represented by the following general formula:

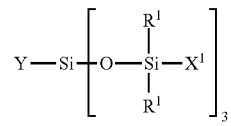

in which $R^1$ represents an aryl group or an alkyl group containing from 1 to 10 carbon atoms, and $X^i$ represents a silylalkyl group which, when i=1, is represented by the formula:

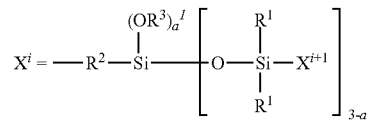

in which $R^1$ is as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 which represents the generation of said silylalkyl group, and $a^i$ is an integer from 0 to 3; Y represents an organic group that is polymerizable with the aid of radicals chosen from:

organic groups containing a methacrylic group or an acrylic group and that are represented by the formulae:

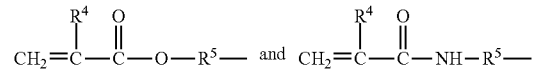

in which $R^4$ represents a hydrogen atom or an alkyl group, $R^5$ represents an alkylene group containing from 1 to 10 carbon atoms, such as a methylene group, an ethylene group, a propylene group or a butylene group, the methylene group and the propylene group being preferred; and organic groups containing a styryl group and that are represented by the formula:

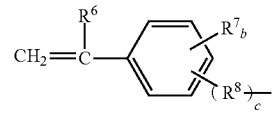

in which $R^6$ represents a hydrogen atom or an alkyl group, $R^7$ represents an alkyl group containing from 1 to 10 carbon atoms, such as a methyl group, an ethyl group, a propyl group or a butyl group, the methyl group being preferred, $R^8$ represents an alkylene group containing from 1 to 10 carbon atoms, such as a methylene group, an ethylene group, a propylene group or a butylene group, the ethylene group being preferred, b is an integer from 0 to 4, and c is 0 or 1 such that if c is 0, —$(R^8)_c$— represents a bond.

According to one embodiment, $R^1$ may represent an aryl group or an alkyl group containing from 1 to 10 carbon atoms. The alkyl group may preferably be represented by a methyl group, an ethyl group, a propyl group, a butyl group, a pentyl group, an isopropyl group, an isobutyl group, a cyclopentyl group or a cyclohexyl group. The aryl group may preferably be represented by a phenyl group and a naphthyl group. The methyl and phenyl groups are more particularly preferred, and the methyl group is preferred among all.

A vinyl polymer bearing at least one carbosiloxane dendrimer-based unit has a molecular side chain containing a carbosiloxane dendrimer structure, and may be derived from the polymerization of:

(A) from 0 to 99.9 parts by weight of a vinyl monomer; and (B) from 100 to 0.1 part by weight of a carbosiloxane dendrimer containing a radical-polymerizable organic group, represented by the general formula:

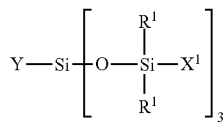

in which Y represents a radical-polymerizable organic group, $R^1$ represents an aryl group or an alkyl group containing from 1 to 10 carbon atoms, and $X^i$ represents a silylalkyl group which, when i=1, is represented by the formula:

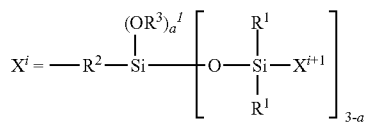

in which $R^1$ is as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 which represents the generation of said silylalkyl group, and $a^i$ is an integer from 0 to 3;

in which said radical-polymerizable organic group contained in the component (B) is chosen from:

organic groups containing a methacrylic group or an acrylic group and that are represented by the formulae:

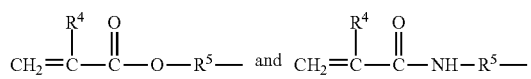

in which $R^4$ represents a hydrogen atom or an alkyl group, $R^5$ represents an alkylene group containing from 1 to 10 carbon atoms; and organic groups containing a styryl group and that are represented by the formula:

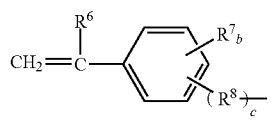

in which $R^6$ represents a hydrogen atom or an alkyl group, $R^7$ represents an alkyl group containing from 1 to 10 carbon atoms, $R^8$ represents an alkylene group containing from 1 to 10 carbon atoms, b is an integer from 0 to 4, and c is 0 or 1, such that if c is 0, $-(R^8)_c-$ represents a bond.

The monomer of vinyl type that is the component (A) in the vinyl polymer is a monomer of vinyl type that contains a radical-polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of an analogous lower alkyl; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of an analogous lower fatty acid; vinyl caproate, vinyl 2-ethylhexoate, vinyl laurate, vinyl stearate or an ester of an analogous higher fatty acid; styrene, vinyltoluene, benzyl methacrylate, phenoxyethyl methacrylate, vinylpyrrolidone or similar vinylaromatic monomers; methacrylamide, N-methylolmethacrylamide, N-methoxymethyl-methacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may also be used.

The following are examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane trioxyethylmethacrylate, tris(2-hydroxyethyl) isocyanurate dimethacrylate, tris(2-hydroxyethyl) isocyanurate trimethacrylate, polydimethylsiloxane capped with styryl groups bearing divinylbenzene groups on the two ends, or similar silicone compounds bearing unsaturated groups.

A carbosiloxane dendrimer, which is the component (B), may be represented by the following formula:

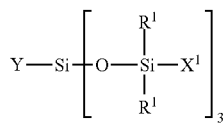

in which Y represents a radical-polymerizable organic group as defined previously.

The following are preferred examples of radical-polymerizable organic groups Y: an acryloxymethyl group, a 3-acryloxypropyl group, a methacryloxymethyl group, a 3-methacryl-oxypropyl group, a 4-vinylphenyl group, a 3-vinylphenyl group, a 4-(2-propenyl)phenyl group, a 3-(2-propenyl)phenyl group, a 2-(4-vinylphenyl)ethyl group, a 2-(3-vinylphenyl)ethyl group, a vinyl group, an allyl group, a methallyl group and a 5-hexenyl group.

R' is as defined previously.

$X^i$ represents a silylalkyl group that is represented by the following formula, when i is equal to 1:

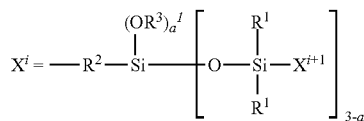

in which $R^1$ is as defined above.

$R^2$ represents an alkylene group containing from 2 to 10 carbon atoms, such as an ethylene group, a propylene group, a butylene group, a hexylene group or a similar linear alkylene group; a methylmethylene group, a methylethylene group, a 1-methylpentylene group, a 1,4-dimethylbutylene group or a similar branched alkylene group.

Ethylene, methylethylene, hexylene, 1-methylpentylene and 1,4-dimethylbutylene groups are above all preferred.

$R^3$ represents an alkyl group containing from 1 to 10 carbon atoms, such as methyl, ethyl, propyl, butyl and isopropyl groups.

$X^{i+1}$ represents a hydrogen atom, an alkyl group containing from 1 to 10 carbon atoms, an aryl group or the silylalkyl group with i=i+1.

$a^i$ is an integer from 0 to 3, and i is an integer from 1 to 10 that indicates the generation number, which represents the number of repetitions of the silylalkyl group.

For example, when the generation number is equal to 1, the carbosiloxane dendrimer may be represented by the first general formula shown below, in which Y, $R^2$ and $R^3$ are the same as defined above, $R^{12}$ represents a hydrogen atom or is identical to $R^1$; $a^1$ is identical to $a^i$. Preferably, the total average number of groups $OR^3$ in a molecule is within the range from 0 to 7.

When the generation number is equal to 2, the carbosiloxane dendrimer may be represented by the second general formula shown below, in which Y, $R^2$, $R^3$ and $R^{12}$ are the same as defined above; $a^1$ and $a^2$ represent the $a^i$ of the indicated generation. Preferably, the total average number of groups $OR^3$ in a molecule is within the range from 0 to 25.

When the generation number is equal to 3, the carbosiloxane dendrimer is represented by the third general formula shown below, in which Y, $R^2$, $R^3$ and $R^{12}$ are the same as defined above; $a^1$, $a^2$ and $a^3$ represent the $a^i$ of the indicated generation. Preferably, the total average number of groups $OR^3$ in a molecule is within the range from 0 to 79.

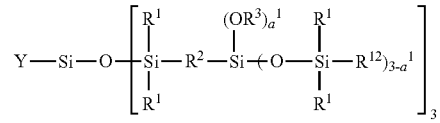 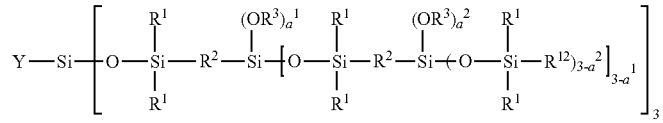

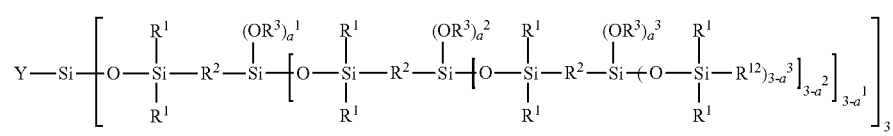

A carbosiloxane dendrimer that contains a radical-polymerizable organic group may be represented by the following mean structural formulae:

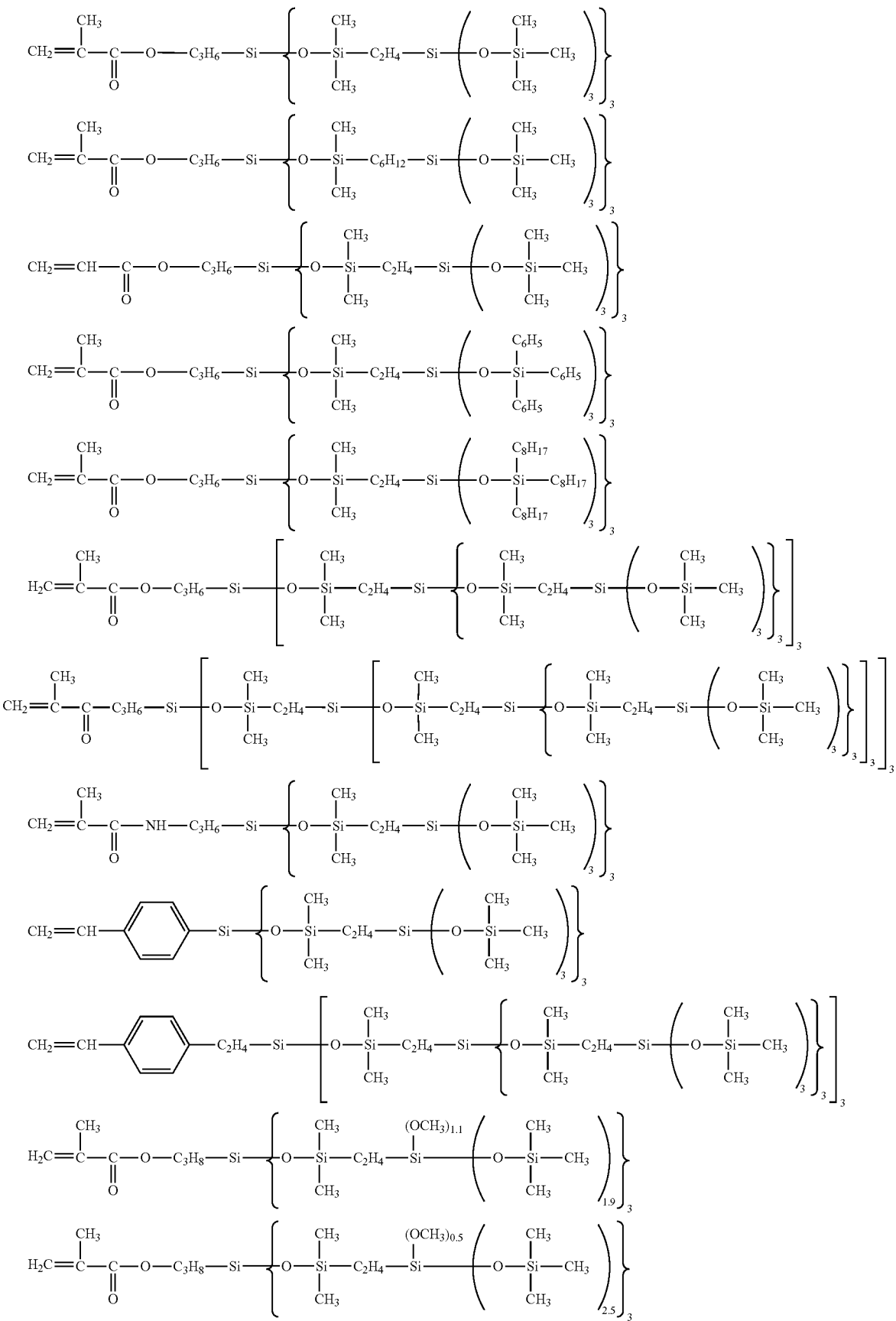

-continued

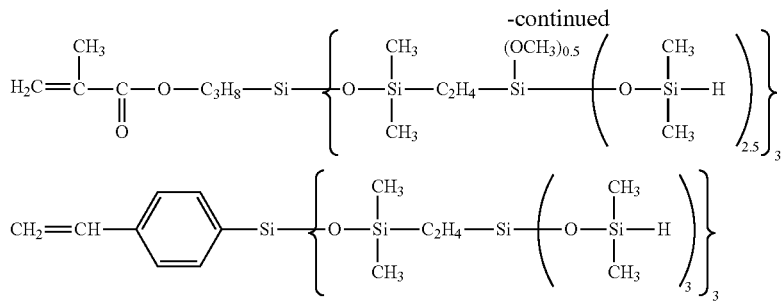

The carbosiloxane dendrimer may be manufactured according to the process for manufacturing a branched silalkylene siloxane described in Japanese patent application Hei 9-171 154.

For example, it may be produced by subjecting an organosilicon compound containing a hydrogen atom linked to a silicon atom, represented by the following general formula:

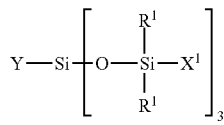

and an organosilicon compound containing an alkenyl group, to a hydrosilylation reaction.

In the above formula, the organosilicon compound may be represented by 3-methacryloxypropyltris(dimethylsiloxy)silane, 3-acryloxypropyltris- may be chosen from the polymers such that the carbosiloxane dendrimer-based unit is (dimethylsiloxy)silane, and 4-vinylphenyltris(dimethylsiloxy)silane. The organosilicon compound which contains an alkenyl group may be represented by vinyltris(trimethylsiloxy)silane, vinyltris(dimethylphenylsiloxy)silane, and 5-hexenyltris(trimethylsiloxy)silane.

The hydrosilylation reaction is performed in the presence of a chloroplatinic acid, a complex of vinylsiloxane and of platinum, or a similar transition metal catalyst.

A vinyl polymer containing at least one carbosiloxane dendrimer-based unit may be chosen from polymers such that the carbosiloxane dendrimer-based unit is a carbosiloxane dendritic structure represented by formula (I):

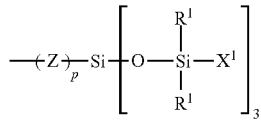

in which Z is a divalent organic group, p is 0 or 1, $R^1$ is an aryl or alkyl group of 1 to 10 carbon atoms and $X^i$ is a silylalkyl group represented by formula (II):

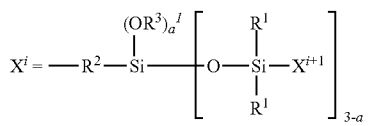

in which $R^1$ is as defined above, $R^2$ is an alkylene group containing from 1 to 10 carbon atoms, $R^3$ is an alkyl group containing from 1 to 10 carbon atoms and $X^{i+1}$ is a group chosen from the group comprising hydrogen atoms, aryl groups and alkyl groups containing up to 10 carbon atoms, and silylalkyl groups $X^i$ in which the power "i" is an integer from 1 to 10 indicating the generation of the starting silylalkyl group in each carbosiloxane dendritic structure with a value of 1 for the group $X^i$ in formula (I) and the index "a" is an integer from 0 to 3.

In a vinyl polymer bearing at least one carbosiloxane dendrimer-based unit, the polymerization ratio between the components (A) and (B), in terms of the weight ratio between (A) and (B), may be within a range from 0/100 to 99.9/0.1, or even from 0.1/99.9 to 99.9/0.1 and preferably within a range from 1/99 to 99/1. A ratio between the components (A) and (B) of 0/100 means that the compound becomes a homopolymer of component (B).

A vinyl polymer bearing at least one carbosiloxane dendrimer-based unit may be obtained by copolymerization of the components (A) and (B), or by polymerization of the component (B) alone.

The polymerization may be a free-radical polymerization or an ionic polymerization, but free-radical polymerization is preferred.

The polymerization may be performed by bringing about a reaction between the components (A) and (B) in a solution for a period of from 3 to 20 hours in the presence of a radical initiator at a temperature of from 50° C. to 150° C.

A suitable solvent for this purpose is hexane, octane, decane, cyclohexane or a similar aliphatic hydrocarbon; benzene, toluene, xylene or a similar aromatic hydrocarbon; diethyl ether, dibutyl ether, tetrahydrofuran, dioxane or similar ethers; acetone, methyl ethyl ketone, methyl isobutyl ketone, diisobutyl ketone or similar ketones; methyl acetate, ethyl acetate, butyl acetate, isobutyl acetate or similar esters; methanol, ethanol, isopropanol, butanol or similar alcohols; octamethylcyclotetrasiloxane, decamethylcyclopentasiloxane, hexamethyldisiloxane, octamethyltrisiloxane or a similar organosiloxane oligomer.

A radical initiator may be any compound known in the art for standard free-radical polymerization reactions. Specific examples of such radical initiators are 2,2'-azobis(isobutyronitrile), 2,2'-azobis(2-methylbutyronitrile), 2,2'-azobis(2,4-dimethylvaleronitrile) or similar compounds of azobis type; benzoyl peroxide, lauroyl peroxide, tert-butyl peroxybenzoate, tert-butyl peroxy-2-ethylhexanoate, or a similar organic peroxide. These radical initiators may be used alone or in a combination of two or more. The radical initiators may be used in an amount of from 0.1 to 5 parts by weight per 100 parts by weight of the components (A) and (B). A chain-transfer agent may be added. The chain-transfer agent may be 2-mercaptoethanol, butyl mercaptan, n-dodecyl mercaptan, 3-mercaptopropyltrimethoxysilane, a polydimethylsiloxane containing a mercaptopropyl group or a similar compound of mercapto type; methylene chloride, chloroform, carbon tetrachloride, butyl bromide, 3-chloropropyltrimethoxysilane or a similar halogenated compound.

In the manufacture of the polymer of vinyl type, after the polymerization, the unreacted residual vinyl monomer may be removed under conditions of heating under vacuum.

To facilitate the preparation of starting material mixture for cosmetic products, the number-average molecular mass of the vinyl polymer bearing a carbosiloxane dendrimer may be chosen within the range between 3000 and 2 000 000 and preferably between 5000 and 800 000. It may be a liquid, a gum, a paste, a solid, a powder, or any other form. The preferred forms are solutions consisting of the dilution of a dispersion or of a powder in solvents.

The vinyl polymer may be a dispersion of a polymer of vinyl type having a carbosiloxane dendrimer structure in its molecular side chain, in a liquid such as a silicone oil, an organic oil, an alcohol or water.

The silicone oil may be a dimethylpolysiloxane with the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethylcyclotrisiloxane, octamethylcyclotetrasiloxane, decamethylcyclopentasiloxane, dodecamethylcyclohexasiloxane or a similar cyclic compound. In addition to the unreactive silicone oils, modified polysiloxanes containing functional groups such as silanol groups, amino groups and polyether groups on the ends or within the molecular side chains may be used.

The organic oils may be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, camelia oil, squalane, castor oil, cottonseed oil, coconut oil, egg yolk oil, polypropylene glycol monooleate, neopentyl glycol 2-ethylhexanoate or a similar glycol ester oil; triglyceryl isostearate, the triglyceride of a fatty acid of coconut oil, or a similar oil of a polyhydric alcohol ester; polyoxyethylene lauryl ether, polyoxypropylene cetyl ether or a similar polyoxyalkylene ether.

The alcohol may be any type that is suitable for use in combination with a cosmetic product starting material. For example, it may be methanol, ethanol, butanol, isopropanol or similar lower alcohols.

A solution or a dispersion of the alcohol should have a viscosity within the range from 10 to $10^9$ mPa at 25° C. To improve the sensory use properties in a cosmetic product, the viscosity should be within the range from 100 to $5\times10^8$ mPa·s.

The solutions and dispersions may be readily prepared by mixing a vinyl polymer bearing at least one carbosiloxane dendrimer-based unit with a silicone oil, an organic oil, an alcohol or water. The liquids may be present in the step of polymerization of a polymer of vinyl type having at least one carbosiloxane dendrimer-based unit. In this case, the unreacted residual vinyl monomer should be completely removed by heat treatment of the solution or dispersion under atmospheric pressure or reduced pressure.

In the case of a dispersion, the dispersity of the polymer of vinyl type may be improved by adding a surfactant.

Such an agent may be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, beef tallow-trimethylammonium hydroxide, coconut oil-trimethylammonium hydroxide, or a similar cationic surfactant; a polyoxyalkylene alkyl ether, a polyoxyalkylenealkylphenol, a polyoxyalkylene alkyl ester, the sorbitol ester of polyoxyalkylene, polyethylene glycol, polypropylene glycol, an ethylene oxide additive of diethylene glycol trimethylnonanol, and nonionic surfactants of polyester type, and also mixtures.

In addition, the solvents and dispersions may be combined with iron oxide suitable for use with cosmetic products, or a similar pigment, and also zinc oxide, titanium oxide, silicon oxide, mica, talc or similar mineral oxides in powder form. In the dispersion, a mean particle diameter of the polymer of vinyl type may be within a range of between 0.001 and 100 microns and preferably between 0.01 and 50 microns. The reason for this is that, outside the recommended range, a cosmetic product mixed with the emulsion will not have a nice enough feel on the skin or to the touch, or sufficient spreading properties or a pleasant feel.

A vinyl polymer contained in the dispersion or the solution may have a concentration in the range between 0.1% and 95% by weight and preferably between 5% and 85% by weight. However, to facilitate the handling and the preparation of the mixture, the range should preferably be between 10% and 75% by weight.

According to one preferred mode, a vinyl polymer that is suitable for use in the invention may be one of the polymers described in the examples of patent application EP 0 963 751.

According to one preferred embodiment, a vinyl polymer grafted with a carbosiloxane dendrimer may be the product of polymerization of:

(A) from 0.1 to 99 parts by weight of one or more acrylate or methacrylate monomers; and (B) from 100 to 0.1 part by weight of an acrylate or methacrylate monomer of a tris[tri(trimethylsiloxy)silylethyldimethylsiloxy]silylpropyl carbosiloxane dendrimer.

According to one embodiment, a vinyl polymer bearing at least one carbosilaxane dendrimer-based unit may comprise a tris[tri(trimethylsiloxy)silylethyl-dimethylsiloxy]silylpropyl carbosiloxane dendrimer-based unit corresponding to one of the formulae:

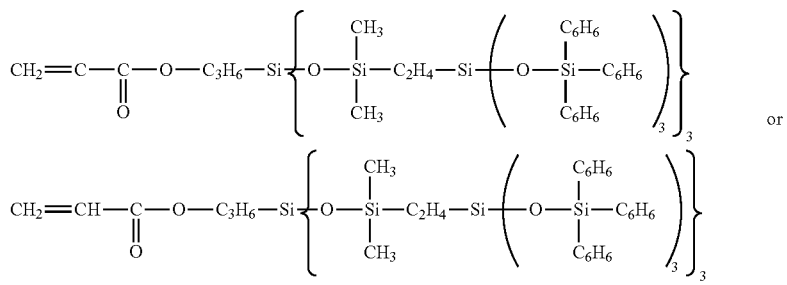

According to one preferred mode, a vinyl polymer bearing at least one carbosiloxane dendrimer-based unit used in the invention comprises at least one butyl acrylate monomer.

According to one embodiment, a vinyl polymer may also comprise at least one fluoro organic group. A fluorinated vinyl polymer may be one of the polymers described in the examples of patent application WO 03/045 337.

According to one preferred embodiment, a vinyl polymer grafted in the sense of the present invention may be conveyed in an oil or a mixture of oils, which is/are preferably volatile, chosen in particular from silicone oils and hydrocarbon-based oils, and mixtures thereof.

According to one particular embodiment, a silicone oil that is suitable for use in the invention may be cyclopentasiloxane.

According to another particular embodiment, a hydrocarbon-based oil that is suitable for use in the invention may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning. The polymers sold under the names FA 4002 ID (TIB 4-202) and FA 4001 CM (TIB 4-230) by the company Dow Corning will preferably be used.

Preferably, the vinyl polymer grafted with at least one carbosiloxane dendrimer-based unit that may be used in a composition of the invention is an acrylate/polytrimethyl siloxymethacrylate copolymer, especially the product sold in isododecane under the name Dow Corning FA 4002 ID Silicone Acrylate by the company Dow Corning.

V. Silicone Acrylate Copolymers

According to one particular embodiment, a composition used according to the invention may comprise, as hydrophobic film-forming polymer, at least one copolymer comprising carboxylate groups and polydimethylsiloxane groups.

In the present application, the term "copolymer comprising carboxylate groups and polydimethylsiloxane groups" means a copolymer obtained from (a) one or more carboxylic (acid or ester) monomers, and (b) one or more polydimethylsiloxane (PDMS) chains.

In the present application, the term "carboxylic monomer" means both carboxylic acid monomers and carboxylic acid ester monomers. Thus, the monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to one preferred embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof.

Thus, according to one particular embodiment of the invention, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

In the present application, the term "polydimethylsiloxanes" (also known as organopolysiloxanes and abbreviated as PDMS) denotes, in accordance with what is generally accepted, any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond comprising trimethyl radicals directly linked via a carbon atom to said silicon atoms. The PDMS chains that may be used to obtain the copolymer used according to the invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The polymerizable radical group may especially be an acrylic or methacrylic group, in particular a group $CH_2$=$CR_1$—CO—O—$R_2$, in which $R_1$ represents a hydrogen or a methyl group and $R_2$ represents —$CH_2$—, —$(CH_2)_n$— with n=3, 5, 8 or 10, —$CH_2$—$CH(CH_3)$—$CH_2$—, —$CH_2$—$CH_2$—O—$CH_2$—$CH_2$—, —$CH_2$—$CH_2$—O—$CH_2$—$CH_2$—$CH(CH_3)$—$CH_2$—, —$CH_2$—$CH_2$—O—$CH_2$ $CH_2$—O—$CH_2$—$CH_2$—$CH_2$—.

The copolymers used in the composition of the invention are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer, as described, for example, in documents U.S. Pat. Nos. 5,061,481 and 5,219,560.

The copolymers obtained generally have a molecular weight ranging from about 3000 to 200 000 and preferably from about 5000 to 100 000.

The copolymer used in the composition of the invention may be in its native form or in dispersed form in a solvent such as lower alcohols containing from 2 to 8 carbon atoms, for instance isopropyl alcohol, or oils, for instance volatile silicone oils (for example cyclopentasiloxane).

As copolymers that may be used in the composition of the invention, mention may be made, for example, of copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. As copolymers that may be used in the composition of the invention, mention may be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). According to one preferred embodiment of the invention, KP561 is preferably used; this copolymer is not dispersed in a solvent, but is in waxy form, its melting point being about 30° C.

Mention may also be made of the grafted copolymer of polyacrylic acid and dimethylpolysiloxane dissolved in isododecane, sold by the company Shin-Etsu under the name KP-550.

Aqueous Phase

The aqueous phase of a composition according to the invention comprises water and optionally a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

Among the water-soluble solvents that may be used in the composition in accordance with the invention, mention may be made especially of lower monoalcohols containing from 1 to 5 carbon atoms such as ethanol and isopropanol, glycols containing from 2 to 8 carbon atoms such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in the composition in a content ranging from 5% to 95%, better still from 30% to 80% by weight and preferably from 40% to 75% by weight relative to the total weight of said composition.

According to another embodiment variant, the aqueous phase of a composition according to the invention may comprise at least one $C_2$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at room temperature.

A polyol suitable for the invention can be a compound of saturated or unsaturated and linear, branched or cyclic alkyl type carrying, on the alkyl chain, at least two —OH functional groups, in particular at least three —OH functional groups and more particularly at least four —OH functional groups.

The polyols advantageously suitable for the formulation of a composition according to the present invention are those exhibiting in particular from 2 to 32 carbon atoms and preferably from 3 to 16 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols such as glycerol oligomers, for instance diglycerol, and polyethylene glycols, and mixtures thereof.

According to a preferred embodiment of the invention, said polyol is chosen from ethylene glycol, pentaerythritol, trimethylolpropane, propylene glycol, glycerol, polyglycerols, polyethylene glycols and mixtures thereof.

According to a particular mode, the composition of the invention may comprise at least propylene glycol.

According to another particular mode, the composition of the invention may comprise at least glycerol.

Oily Phase

For the purposes of the invention, an oily phase comprises at least one oil.

The term "oil" means any fatty substance that is in liquid form at room temperature and atmospheric pressure.

An oily phase that is suitable for preparing the compositions, especially cosmetic compositions according to the invention, may comprise hydrocarbon-based oils, silicone oils, fluoro oils or non-fluoro oils, or mixtures thereof.

The oils may be volatile or non-volatile.

They may be of animal, plant, mineral or synthetic origin. According to one embodiment variant, oils of silicone origin are preferred.

For the purposes of the present invention, the term "non-volatile oil" means an oil with a vapour pressure of less than 0.13 Pa.

For the purposes of the present invention, the term "silicone oil" means an oil comprising at least one silicon atom, and in particular at least one Si—O group.

The term 'fluoro oil' means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

For the purposes of the invention, the term "volatile oil" means any oil that is capable of evaporating on contact with the skin in less than one hour, at room temperature and atmospheric pressure. The volatile oil is a volatile cosmetic compound, which is liquid at room temperature, especially having a nonzero vapour pressure, at room temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Volatile Oils

The volatile oils may be hydrocarbon-based oils or silicone oils.

Among the volatile hydrocarbon-based oils containing from 8 to 16 carbon atoms, mention may be made especially of branched $C_8$-$C_{16}$ alkanes, such as $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, such as isohexyl neopentanoate, and mixtures thereof. Preferably, the volatile hydrocarbon-based oil is chosen from volatile hydrocarbon-based oils containing from 8 to 16 carbon atoms, and mixtures thereof, in particular from isododecane, isodecane and isohexadecane, and is especially isohexadecane.

Mention may also be made of volatile linear alkanes comprising from 8 to 16 carbon atoms, in particular from 10 to 15 carbon atoms and more particularly from 11 to 13 carbon atoms, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, mixtures of n-undecane ($C_{11}$) and of n-tridecane ($C_{13}$) obtained in Examples 1 and 2 of patent application WO 2008/155 059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane and dodecamethylcyclohexasiloxane.

Non-Volatile Oils

The non-volatile oils may be chosen especially from non-volatile hydrocarbon-based, fluoro and/or silicone oils.

Non-volatile hydrocarbon-based oils that may especially be mentioned include:
- hydrocarbon-based oils of animal origin,
- hydrocarbon-based oils of plant origin, synthetic ethers containing from 10 to 40 carbon atoms, such as dicapryl ether,
- synthetic esters, such as the oils of formula $R_1COOR_2$, in which $R_1$ represents a linear or branched fatty acid residue comprising from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from fatty acid alcohol esters, for instance cetostearyl octanoate, isopropyl alcohol esters such as isopropyl myristate or isopropyl palmitate, ethyl palmitate, 2-ethylhexyl palmitate, isopropyl stearate, octyl stearate, hydroxylated esters, such as isostearyl lactate or octyl hydroxystearate, alkyl or polyalkyl ricinoleates, hexyl laurate, neopentanoic acid esters, such as isodecyl neopentanoate or isotridecyl neopentanoate, and isononanoic acid esters, such as isononyl isononanoate or isotridecyl isononanoate,
- polyol esters and pentaerythritol esters, such as dipentaerythrityl tetrahydroxy stearate/tetraisostearate,
- fatty alcohols that are liquid at room temperature, with a branched and/or unsaturated carbon-based chain containing from 12 to 26 carbon atoms, for instance 2-octyldodecanol, isostearyl alcohol and oleyl alcohol,
- $C_{12}$-$C_{22}$ higher fatty acids, such as oleic acid, linoleic acid, linolenic acid, and mixtures thereof,
- non-phenyl silicone oils, for instance caprylyl methicone, and
- phenyl silicone oils, for instance phenyl trimethicones, phenyl dimethicones, phenyltrimethylsiloxydiphenylsiloxanes, diphenyl dimethicones, diphenylmethyldiphenyltri siloxanes and 2-phenylethyl trimethylsiloxysilicates, dimethicones or phenyl trimethicone with a viscosity of less than or equal to 100 cSt, and trimethylpentaphenyl-trisiloxane, and mixtures thereof; and also mixtures of these various oils.

Preferably, a composition according to the invention comprises volatile and/or non-volatile silicone oils. Such silicone oils are particularly appreciated when the lipophilic gelling agent is an organopolysiloxane elastomer.

A composition according to the invention may comprise from 5% to 95% by weight, better still from 5% to 40% by weight and preferably from 7% to 35% by weight of oil(s) relative to the total weight of said composition.

As mentioned above, the gelled oily phase according to the invention may have a threshold stress of greater than 1.5 Pa and preferably greater than 10 Pa.

The gelled oily phase according to the invention may have a threshold stress of lower than 10 000 Pa preferably lower than 5 000 Pa.

This threshold stress value reflects a gel-type texture of this oily phase.

Dyestuffs

A composition according to the invention may also comprise at least one particulate or non-particulate, water-soluble or water-insoluble dyestuff, preferably in a proportion of at least 0.01% by weight relative to the total weight of the composition.

For obvious reasons, this amount is liable to vary significantly with regard to the intensity of the desired colour effect and of the colour intensity afforded by the dyestuffs under consideration, and its adjustment clearly falls within the competence of a person skilled in the art.

A composition according to the invention may comprise from 0.01% to 25% by weight, especially from 0.1% to 25% by weight, in particular from 1% to 20% by weight and preferably from 5% to 15% by weight of dyestuffs relative to the total weight of said composition.

As stated above, the dyestuffs that are suitable for use in the invention may be water-soluble, but may also be liposoluble.

For the purposes of the invention, the term "water-soluble dyestuff" means any natural or synthetic, generally organic compound, which is soluble in an aqueous phase or water-miscible solvents and which is capable of imparting colour.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanine (beetroot), carmine, copper chlorophylline, methylene blue, anthocyanins (enocianin, black carrot, hibiscus and elder), caramel and riboflavin.

The water-soluble dyes are, for example, beetroot juice and caramel.

For the purposes of the invention, the term "liposoluble dyestuff" means any natural or synthetic, generally organic compound, which is soluble in an oily phase or in solvents that are miscible with a fatty substance, and which is capable of imparting colour.

As liposoluble dyes that are suitable for use in the invention, mention may be made especially of synthetic or natural liposoluble dyes, for instance DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

The colouring particulate materials may be present in a proportion of from 0.01% to 25% by weight, especially from 0.1% to 25% by weight, in particular from 1% to 20% by weight and preferably from 5% to 15% by weight relative to the total weight of said composition containing them.

They may especially be pigments, nacres and/or particles with metallic tints.

The term "pigments" should be understood as meaning white or coloured, mineral or organic particles that are insoluble in an aqueous solution, which are intended to colour and/or opacify the composition containing them.

A composition according to the invention may comprise from 0.01% to 25% by weight, especially from 0.1% to 25% by weight, in particular from 1% to 25% by weight and preferably from 5% to 15% by weight of pigments relative to the total weight of said composition.

Preferably, when the composition according to the invention is a makeup composition, it may comprise at least 5% and preferentially at least 10% by weight of pigments, relative to the total weight of said composition.

The pigments may be white or coloured, and mineral and/or organic.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment consisting of silica microspheres containing yellow iron oxide.

Advantageously, the pigments in accordance with the invention are iron oxides and/or titanium dioxides.

The term "nacres" should be understood as meaning iridescent or non-iridescent coloured particles of any shape, especially produced by certain molluscs in their shell or alternatively synthesized, which have a colour effect via optical interference.

A composition according to the invention may comprise from 0% to 15% and in particular from 1% to 8% by weight of nacres relative to the total weight of said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the commercially available nacres that may be mentioned are the nacres Timica, Flamenco and Duochrome (on mica base) sold by the company Engelhard, the Timiron nacres sold by the company Merck, the Prestige nacres on mica base sold by the company Eckart and the Sunshine nacres on synthetic mica base sold by the company Sun Chemical.

The nacres may more particularly have a yellow, pink, red, bronze, orange, brown and/or coppery colour or tint.

Advantageously, the nacres in accordance with the invention are micas coated with titanium dioxide or with iron oxide, and also bismuth oxychloride.

For the purposes of the present invention, the term "particles with a metallic tint" means any compound whose nature, size, structure and surface finish allow it to reflect the incident light, especially in a non-iridescent manner.

The particles with a metallic tint that may be used in the invention are in particular chosen from:
particles of at least one metal and/or of at least one metal derivative,
particles comprising a monomaterial or multimaterial, organic or mineral substrate, at least partially coated with at least one layer with a metallic tint comprising at least one metal and/or at least one metal derivative, and
mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" denotes compounds derived from metals, especially oxides, fluorides, chlorides and sulfides.

Illustrations of these particles that may be mentioned include aluminium particles, such as those sold under the names Starbrite 1200 EAC® by the company Siberline and Metalure® by the company Eckart and glass particles coated with a metallic layer, especially those described in documents JP-A-09188830, JP-A-10158450, JP-A-10158541, JP-A-07258460 and JP-A-05017710.

Hydrophobic Treatment of the Dyestuffs

The pulverulent dyestuffs as described previously may be totally or partially surface-treated, with a hydrophobic agent, to make them more compatible with the oily phase of the composition of the invention, especially so that they have good wettability with oils. Thus, these treated pigments are well dispersed in the oily phase.

Hydrophobic-treated pigments are described especially in document EP-A-1 086 683.

The hydrophobic-treatment agent may be chosen from silicones such as methicones, dimethicones and perfluoroalkylsilanes; fatty acids, such as stearic acid; metal soaps, such as aluminium dimyristate, the aluminium salt of hydrogenated tallow glutamate; perfluoroalkyl phosphates, polyhexafluoropropylene oxides; perfluoropolyethers; amino acids; N-acylamino acids or salts thereof; lecithin, isopropyl triisostearyl titanate, isostearyl sebacate, and mixtures thereof.

The term "alkyl" mentioned in the compounds cited above especially denotes an alkyl group containing from 1 to 30 carbon atoms and preferably containing from 5 to 16 carbon atoms.

Polar Additive(S)

Advantageously, a composition according to the invention may also comprise one or more polar additive(s), especially when it contains pigments.

According to the present invention, the use of such a polar additive facilitates the homogenization of the dispersion in the presence of pigments.

The polar additive may be chosen from compounds considered as good hydrogen bond donors or acceptors, for instance fatty alcohols, fatty acids, diols and esters, and mixtures thereof.

According to one embodiment, the polar additives of the invention may be polar oils, for instance:
hydrocarbon-based plant oils with a high content of triglycerides consisting of fatty ($C_8$ to $C_{24}$) acid esters of glycerol in which the fatty acids may have varied chain lengths, these chains possibly being linear or branched, and saturated or unsaturated; these oils are in particular wheatgerm oil, corn oil, sunflower oil, shea oil, castor oil, sweet almond oil, macadamia oil, apricot oil, soybean oil, rapeseed oil, cottonseed oil, alfalfa oil, poppy seed oil, pumpkin seed oil, sesame seed oil, marrow oil, avocado oil, hazelnut oil, grapeseed oil, blackcurrant seed oil, evening primrose oil, millet oil, barley oil, quinoa oil, olive oil, rye oil, safflower oil, candlenut oil, passion flower oil and musk rose oil; or caprylic/capric acid triglycerides such as those sold by the company Stearineries Dubois or those sold under the names Miglyol 810, 812 and 818 by the company Dynamit Nobel;

synthetic oils of formula $R_5COOR_6$ in which $R_5$ represents a linear or branched higher fatty acid residue comprising from 7 to 40 carbon atoms and $R_6$ represents a branched hydrocarbon-based chain containing from 3 to 40 carbon atoms, for instance purcellin oil (cetostearyl octanoate), isononyl isononanoate or $C_{12}$ to $C_{15}$ alkyl benzoate;

synthetic esters and ethers such as isopropyl myristate, 2-ethylhexyl palmitate, alcohol or polyalcohol octanoates, decanoates or ricinoleates, hydroxylated esters such as isostearyl lactate, diisostearyl malate; and pentaerythritol esters;

fatty acids containing from 12 to 22 carbon atoms, for instance oleic acid, linoleic acid or linolenic acid; and mixtures thereof.

According to another embodiment, the polar additives of the invention may be amphiphilic compounds.

The amphiphilic compound(s) that may be used in the composition of the invention comprise a lipophilic part linked to a polar part, the lipophilic part possibly comprising a carbon-based chain containing at least 8 carbon atoms, especially from 18 to 32 carbon atoms and better still from 18 to 28 carbon atoms. Preferably, the polar part of this or these amphiphilic compound(s) is the residue of a compound chosen from alcohols and poly alcohols containing from 1 to 12 hydroxyl groups, polyoxyalkylenes comprising at least two oxyalkylene units and containing from 0 to 20 oxypropylene units and/or from 0 to 20 oxyethylene units.

In particular, the amphiphilic compound is an ester chosen from glyceryl, sorbitan or methylglucose hydroxystearates, oleates or isostearates, or alternatively branched $C_{12}$ to $C_{26}$ fatty alcohols such as octyldodecanol, and mixtures thereof. Among these esters, monoesters and mixtures of monoesters and diesters are particularly preferred.

The amphiphilic compounds may also be silicone-based. These amphiphilic silicones comprise a silicone part that is compatible with the highly silicone medium of the compositions of the invention, and a hydrophilic part that may be, for example, the residue of a compound chosen from alcohols and polyols, containing from 1 to 12 hydroxyl groups, polyoxyalkylenes comprising at least two oxyalkylene units and containing from 0 to 20 oxypropylene units and/or from 0 to 20 oxyethylene units. This hydrophilic part thus has affinity for the hydrophilic particles and promotes their dispersion in the silicone medium.

The polar additives of the invention may be agents for screening out UV-B and/or UV-A rays, the total amount of screening agents possibly being between 0.01% and 10% by weight relative to the total weight of the composition.

A composition according to the invention may comprise from 0.01% to 10% by weight, especially from 0.05% to 5% by weight and in particular from 0.05% to 1% by weight of polar additive(s).

Fillers

Advantageously, a composition according to the invention may also comprise one or more fillers conventionally used in care and/or makeup compositions.

These fillers are colourless or white solid particles of any form, which are in a form that is insoluble and dispersed in the medium of the composition.

These fillers, of mineral or organic, natural or synthetic nature, give the composition containing them softness and give the makeup result a matt effect and uniformity. In addition, these fillers advantageously make it possible to combat various attacking factors such as sebum or sweat.

As illustrations of these fillers, mention may be made of talc, mica, silica, kaolin, poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie), acrylic acid copolymers, silicone resin microbeads (for example Tospearls® from Toshiba), polyorganosiloxane elastomer particles, precipitated calcium carbonate, magnesium carbonate, magnesium hydrogen carbonate, hydroxyapatite, barium sulfate, aluminium oxides, polyurethane powders, composite fillers, hollow silica microspheres, and glass or ceramic microcapsules. Use may also be made of particles which are in the form of hollow sphere portions, as described in patent applications JP-2003 128 788 and JP-2000 191 789.

In particular, such fillers may be present in a composition according to the invention in a content of between 0.01% and 25% by weight, especially between 0.1% and 20% by weight and in particular between 1% and 10% by weight relative to the total weight of the composition.

According to one embodiment of the invention, a composition may comprise at least solid particles such as pigments and/or fillers.

Advantageously, a composition according to the invention may comprise from 0.01% to 25% by weight, especially from 0.1% to 25% by weight, in particular from 1% to 20% by weight and preferably from 5% to 15% by weight of solid particles relative to the total weight of the composition.

Dispersant

Advantageously, a composition according to the invention may also comprise a dispersant.

Such a dispersant may be a surfactant, an oligomer, a polymer or a mixture of several thereof.

According to one particular embodiment, a dispersant in accordance with the invention is a surfactant.

Active Agent

A composition according to the invention may comprise at least one moisturizer (also known as a humectant), in particular for a care application.

Preferably, the moisturizer is glycerol.

The moisturizer(s) may be present in the composition in a content ranging from 0.1% to 15% by weight, especially from 0.5% to 10% by weight or even from 1% to 6% by weight relative to the total weight of said composition.

As other active agents that may be used in the composition of the invention, examples that may be mentioned include vitamins and sunscreens, and mixtures thereof.

Preferably, a composition according to the invention comprises at least one active agent.

It is a matter of routine operations for a person skilled in the art to adjust the nature and the amount of the additives present in the compositions in accordance with the invention such that the desired cosmetic properties thereof are not thereby affected.

According to one embodiment, a composition of the invention may advantageously be in the form of a composition for caring for the skin and/or keratin fibres, the body or the face, in particular the face.

According to another embodiment, a composition of the invention may advantageously be in the form of a composition for making up the skin and/or keratin fibres, the body or the face, in particular the face.

Thus, according to a sub-mode of this embodiment, a composition of the invention may advantageously be in the form of a makeup base composition.

A composition of the invention may advantageously be in the form of a foundation.

According to another sub-mode of this embodiment, a composition of the invention may advantageously be in the form of a composition for making up the skin and especially the face. It may thus be an eyeshadow or a face powder.

According to yet another sub-mode of this embodiment, a composition of the invention may advantageously be in the form of a lip product, especially a lipstick.

According to yet another sub-mode of this embodiment, a composition of the invention may be in the form of a product for the eyelashes, in particular a mascara.

According to yet another sub-mode of this embodiment, a composition of the invention may advantageously be in the form of a product for the eyebrows, in particular an eyebrow pencil.

Such compositions are especially prepared according to the general knowledge of a person skilled in the art.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

The invention is illustrated in greater detail by the examples and figures presented below. Unless otherwise mentioned, the amounts indicated are expressed as mass percentages.

Methodology for the Oscillating Dynamic Rheology Measurements

These are harmonic-regime rheology measurements for measuring the elastic modulus.

The measurements are taken using a Haake RS600 rheometer on a product at rest, at 25° C. with a plate-plate rotor Ø 60 mm and a 2 mm gap.

The harmonic-regime measurements make it possible to characterize the viscoelastic properties of the products. The technique consists in subjecting a material to a stress which varies sinusoidally over time and in measuring the response of the material to this stress. In a range in which the behaviour is linear viscoelastic behaviour (zone in which the strain is proportional to the stress), the stress ($\tau$) and the strain ($\gamma$) are two sinusoidal functions of time which are written in the following manner:

$$\tau(t) = \tau_0 \sin(\omega t)$$

$$\gamma(t) = \gamma_0 \sin(\omega t + \delta)$$

in which:

$\tau_0$ represents the maximum amplitude of the stress (Pa);
$\gamma_0$ represents the maximum amplitude of the strain (–);
$\omega = 2\Pi N$ represents the angular frequency (rad·s$^{-1}$) with N representing the frequency (Hz); and
$\delta$ represents the phase shift of the stress relative to the strain (rad).

Thus, the two functions have the same angular frequency, but they are shifted by an angle $\delta$. Depending on the phase shift $\delta$ between $\tau(t)$ and $\gamma(t)$, the behaviour of the system may be apprehended:

if $\delta = 0$, the material is purely elastic;
if $\delta = \Pi/2$, the material is purely viscous (Newtonian fluid); and
if $0 < \delta < \Pi/2$, the material is viscoelastic.

In general, the stress and the strain are written in complex form:

$$\tau^*(t) = \tau_0 e^{i\omega t}$$

$$\gamma^*(t) = \gamma_0 e^{(i\omega t + \delta)}$$

A complex stiffness modulus, representing the overall resistance of the material to the strain, whether it is of elastic or viscous origin, is then defined by:

$$G^* = \tau^*/\gamma^* = G' + iG''$$

in which:

G' is the storage modulus or elastic modulus, which characterizes the energy stored and totally restituted during a cycle, $G' = (\tau_0/\gamma_0) \cos \delta$; and G" is the loss modulus or viscous modulus, which characterizes the energy dissipated by internal friction during a cycle, $G'' = (\tau_0/\gamma_0) \sin \delta$.

The parameter retained is the mean stiffness modulus G* recorded at the plateau measured at a frequency of 1 Hz.

EXAMPLES

Example 1: Care Compositions

Care formulations in accordance with the invention are prepared as described below.

The components of phase A are weighed out in a beaker and stirred with a Rayneri blender, at room temperature.

The components of phase B are weighed out and added to phase A and stirred vigorously with a Rayneri blender, at room temperature.

The walls and base of the beaker are scraped using a spatula and the mixture is left to homogenize with vigorous stirring at room temperature until the mixture becomes completely homogeneous.

A white bi-gel composition is formed.

The formulation is prepared using the weight proportions described below. The percentages are given on a weight basis relative to the total weight of the composition.

| Phase | Compounds | Formula 1 Outside the invention | Formula 2 According to the invention | Formula 3 According to the invention | Formula 4 According to the invention |
|---|---|---|---|---|---|
| Phase A | Microbiologically clean deionized water | qs 100 | qs 100 | qs 100 | qs 100 |
| | Glycerol (Concerine CD 99.5 Nat) | 6.6% | 6.1% | 6.1% | 6.1% |
| | Phenoxyethanol (Neolone PH 100 Preservative sold by the company Dow Chemical) | 1.0% | 0.9% | 0.9% | 0.9% |
| | Sodium acrylamido-2-methylpropanesulfonate/hydroxyethyl acrylate copolymer in powder form | 3.0% | 2.8% | 2.8% | 2.8% |

| Phase | Compounds | Formula 1 Outside the invention | Formula 2 According to the invention | Formula 3 According to the invention | Formula 4 According to the invention |
|---|---|---|---|---|---|
| | (Sepinov ® EMT 10 sold by the company SEPPIC) | | | | |
| Phase B | Mixture of polydimethylsiloxane crosslinked with hexadiene and polydimethylsiloxane 5 cSt (Dow Corning EL-9240 ® silicone elastomer blend sold by the company Dow Corning) | 17.5% | 16.3% | 16.3% | 16.3% |
| | Crosslinked polydimethylsiloxane 5 cSt (Xiameter PMX-200 Silicone Fluid 5CS sold by the company Dow Corning) | 10.0% | 9.3% | 9.3% | 9.3% |
| | Trimethyl siloxysilicate resin | / | 6.9% | / | / |
| | Copolymer of butyl acrylate containing dendritic silicone side chains, diluted to 40% in isododecane (Dow Corning ® FA 4002 ID Silicone Acrylate sold by the company Dow Corning) | / | / | 17.2% | / |
| | Acrylic acid/isobutyl acrylate/isobornyl acrylate copolymer diluted to 50% in isododecane (Mexomer PAS sold by the company Chimex) | / | / | / | 13.7% |

Protocol for Evaluating the Technical Effect of the Compositions

In order to evaluate the staying power of the matt effect of the compositions, an in vitro gloss test was performed.

To do this, a 25 µm deposit of each formula is produced on a contrast card.

Using a Byk glossmeter (angle 60°), several gloss measurements are taken at T=0 and then at T=24 hours.

The results clearly demonstrate that compositions 2, 3 and 4 show much greater staying power of the matt effect than the control composition 1. Thus, the presence of hydrophobic film-forming polymer in a gel-gel composition makes it possible to ensure much greater staying power over time of the matt effect.

In other words, the compositions according to the invention significantly improve the staying power of the matt effect after 24 hours.

Example 2: Foundation Composition According to the Invention

A foundation formulation in accordance with the invention is prepared as described below.

The components of phase A are weighed out and stirred with a Rayneri blender, at room temperature.

The components of phase B are weighed out and stirred with a Rayneri blender, at room temperature.

The components of phase B are added to phase A and stirred vigorously with a Rayneri blender, at room temperature.

The walls and base of the beaker are scraped using a spatula and the mixture is left to homogenize with vigorous stirring at room temperature until completely homogeneous.

A Gel-Gel Composition Forms.

The formulation is prepared using the weight proportions described below. The percentages are given on a weight basis relative to the total weight of the composition.

| Phase | Compounds | Formula 5 According to the invention | Formula 6 According to the invention |
|---|---|---|---|
| Phase A | Microbiologically clean deionized water | qs 100 | qs 100 |
| | Glycerol (Concerine CD 99.5 Nat) | 3.0 | 0.3 |
| | 1,3-Butylene glycol | 3.0 | / |
| | Branched polydimethylsiloxane bearing triglycerol and PDMS groups (KF-6100 sold by the company Shin-Etsu) | 0.6 | 0.6 |
| | Hydroxyethyl acrylate/sodium acryloyldimethyltaurate copolymer (Sepinov ® EMT 10 sold by the company SEPPIC) | 1.8 | 1.8 |
| Phase B | Mixture of polydimethylsiloxane crosslinked with hexadiene and polydimethylsiloxane 5 cSt (Dow Corning EL-9240 ® silicone elastomer blend sold by the company Dow Corning) | 2.5 | 2.5 |
| | Trimethyl siloxysilicate resin | 5.9 | 5.9 |
| | Cyclohexadimethylsiloxane 8 cSt (Xiameter PMX-0246 cyclohexasiloxane sold by the company Dow Corning) | 5 | 13 |
| | Isohexadecane | 8 | / |
| | Silica gel treated with hexamethyldisiloxane (VM-2270 Aerogel Fine Particles sold by the company Dow Corning) | 0.4 | 0.4 |
| | Crosslinked polymethyl methacrylate (PMMA) hemispheres (Sepimat H 10 sold by the company SEPPIC) | 2.1 | 2.1 |
| | Titanium oxide (NAI-TAO-77891 sold by the company Miyoshi Kasei) | 9.4 | 9.4 |
| | Iron oxides (NAI-C33-9001-10, NAI-C33-7001-10 and NAI-C33-8001-10 sold by the company Miyoshi Kasei) | 2.4 | 2.4 |

Protocol for Evaluating the Technical Effect of the Compositions

The compositions were tested in vivo in an instrumental evaluation under standard conditions, over 3 hours at room temperature, in order to test their resistance to sebum, and under extreme conditions (30 minutes at 37° C., 60% RH) to test their resistance to sweat.

Compared with a multi-phase composition not containing any hydrophobic film-forming polymers, the compositions according to the invention show better resistance to sebum and to sweat.

Example 3: Eyebrow Makeup Composition

An eyebrow makeup formulation in accordance with the invention is prepared as described below.

The components of phase A are weighed out and stirred with a Rayneri blender, at room temperature.

The components of phase B are weighed out and stirred with a Rayneri blender, at room temperature.

The components of phase B are added to phase A and stirred vigorously with a Rayneri blender, at room temperature.

The walls and base of the beaker are scraped using a spatula and the mixture is left to homogenize with vigorous stirring at room temperature until completely homogeneous.

A gel-gel composition forms.

The formulation is prepared using the weight proportions described below. The percentages are given on a weight basis relative to the total weight of the composition.

| Phase | Compounds | Formula 7 According to the invention |
|---|---|---|
| Phase A | Microbiologically clean deionized water | qs 100 |
| | Glycerol (Concerine CD 99.5 Nat) | 4.5 |
| | Sodium acrylamido-2-methylpropanesulfonate/hydroxyethyl acrylate copolymer in powder form (Sepinov ® EMT 10 sold by the company SEPPIC) | 1.6 |
| | Branched polydimethylsiloxane bearing triglycerol and PDMS groups (KF-6100 sold by the company Shin-Etsu) | 0.6 |
| | Preserving agent | 0.9 |
| Phase B | Trimethyl siloxysilicate resin | 5.3 |
| | Cyclohexadimethylsiloxane 8 cSt (Xiameter PMX-0246 cyclohexasiloxane sold by the company Dow Corning) | 10.7 |
| | Mixture of polydimethylsiloxane crosslinked with hexadiene and polydimethylsiloxane 5 cSt (Dow Corning EL-9240 ® silicone elastomer blend sold by the company Dow Corning) | 2.5 |
| | Dodecamethylpentasiloxane, PDMS 2 cSt (DM-Fluid-2cs sold by the company Shin-Etsu) | 7.2 |
| | Silica gel treated with hexamethyldisiloxane (without loose powder) (VM-2270 Aerogel Fine Particles sold by the company Dow Corning) | 0.3 |
| | Ethylene glycol dimethacrylate/lauryl methacrylate copolymer (Polytrap ® 6603 Adsorber) | 2.3 |
| | Crosslinked polymethyl methacrylate (PMMA) hemispheres (Sepimat H 10 sold by the company SEPPIC) | 4.5 |
| | Titanium oxide (NAI-TAO-77891 sold by the company Miyoshi Kasei) | 2.6 |
| | Iron oxides (NAI-C33-9001-10, NAI-C33-7001-10 and NAI-C33-8001-10 sold by the company Miyoshi Kasei) | 7.4 |

The composition makes it possible to give the eyebrows freshness and lightness. It affords a good pay-off, i.e. a good deposit on the eyebrows, and allows them to be redrawn naturally.

The staying power over time of the makeup result is very good, as is its comfort in the course of the day.

The invention claimed is:

1. Gel-gel type composition, different from an emulsion, for making up and/or caring for the skin, comprising:
    at least one aqueous phase gelled with at least one hydrophilic gelling agent which is a copolymer of 2-acrylamido-2-methylpropanesulfonic acid and of hydroxyethyl acrylate; and
    at least one oily phase gelled with at least one lipophilic gelling agent chosen from organopolysiloxane elastomers;
    said phases forming therein a macroscopically homogeneous mixture;
    said composition also comprising at least one hydrophobic film-forming polymer chosen from block ethylenic polymers, vinyl polymers comprising at least one carbosiloxane dendrimer derivative and silicone resins.

2. Composition according to claim 1, comprising from 0.1% to 30% by weight of hydrophobic film-forming polymer(s) relative to the total weight of the composition.

3. Composition according to claim 1, in which said hydrophobic film-forming polymer(s) are present totally or partially in the gelled oily phase.

4. Composition according to claim 1, in which the hydrophobic film-forming polymer is a trimethyl siloxysilicate resin.

5. Composition according to claim 1, comprising, as lipophilic gelling agent, at least one crosslinked silicone elastomer of MCI name Dimethicone (and) Dimethicone Crosspolymer.

6. Composition according to claim 1, containing the aqueous and oily phases in an aqueous phase/oily phase weight ratio of from 95/5 to 5/95.

7. Composition according to claim 1, also comprising at least solid particles.

8. Composition according to claim 1, comprising pigments in combination with a polar additive.

9. Composition according to claim 1, also comprising volatile and/or non-volatile silicone oils.

10. Composition according to claim 1, also comprising at least one moisturizer.

11. Composition according to claim 1, in the form of a composition for making up the skin, the body or the face.

12. Process for preparing a gel-gel type composition, different from an emulsion, for making up and/or caring for the skin, comprising at least one step of mixing:
    an aqueous phase gelled with at least one hydrophilic gelling agent which is a copolymer of 2-acrylamido-2-methylpropanesulfonic acid and of hydroxyethyl acrylate; and
    at least one oily phase gelled with at least one lipophilic gelling agent chosen from organopolysiloxane elastomers;
    under conditions suitable for obtaining a macroscopically homogeneous mixture;
    said composition also comprising at least one hydrophobic film-forming polymer chosen from block ethylenic polymers, vinyl polymers comprising at least one carbosiloxane dendrimer derivative and silicone resins.

13. Process according to claim 12, comprising a step of mixing at least three or even more gelled phases.

14. Process according to either of claims 12 and 13, in which the mixing is performed at room temperature.

15. Cosmetic process for making up and/or caring for the skin, comprising at least one step which consists in applying to said skin a composition as defined according to claim 1.

16. Cosmetic process for making up and/or caring for the skin, comprising at least the application to said skin of a macroscopically homogeneous gel-gel type composition, different from an emulsion, obtained by extemporaneous mixing, before application or at the time of application to said skin, of at least one aqueous phase gelled with at least one hydrophilic gelling agent which is a copolymer of 2-acrylamido-2-methylpropanesulfonic acid and of hydroxyethyl acrylate, and at least one oily phase gelled with at least one lipophilic gelling agent chosen from organopolysiloxane elastomers; and said composition also comprising at least one hydrophobic film-forming polymer chosen from block ethylenic polymers, vinyl polymers comprising at least one carbosiloxane dendrimer derivative and silicone resins.

17. Composition according to claim 1, wherein the composition is in a form of a creamy gel.

18. Composition according to claim 1, wherein said silicone resin is chosen from T resin, MQ resin, and mixtures thereof.

19. Composition according to claim 1, wherein the gelled aqueous phase and the gelled oily phase interpenetrate to form a stable, consistent product.

20. Composition according to claim 1, wherein a ratio of a viscosity of the gelled at least one aqueous phase to a viscosity of the gelled at least one oily phase, measured at 25° C. and 100 $s^{-1}$, ranges from 0.2 to 3.

* * * * *